US012637646B2

(12) United States Patent
Shahhosseini et al.

(10) Patent No.: US 12,637,646 B2
(45) Date of Patent: May 26, 2026

(54) DNA ORIGAMI CELL SENSING PLATFORM

(71) Applicant: Ohio State Innovation Foundation, Columbus, OH (US)

(72) Inventors: Melika Shahhosseini, Columbus, OH (US); Carlos Castro, Columbus, OH (US); Jonathan Song, Columbus, OH (US); Ehsan Akbari, Columbus, OH (US); Peter Beshay, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 514 days.

(21) Appl. No.: 18/154,110

(22) Filed: Jan. 13, 2023

(65) Prior Publication Data

US 2024/0018455 A1 Jan. 18, 2024

Related U.S. Application Data

(60) Provisional application No. 63/305,778, filed on Feb. 2, 2022, provisional application No. 63/266,849, filed on Jan. 17, 2022.

(51) Int. Cl.
*C12M 1/00* (2006.01)
*C12M 1/12* (2006.01)
*C12M 3/06* (2006.01)
*G01N 1/00* (2006.01)

(52) U.S. Cl.
CPC ............ *C12M 23/16* (2013.01); *C12M 25/14* (2013.01)

(58) Field of Classification Search
CPC .............................. C12M 23/20; C12M 23/14
See application file for complete search history.

(56) References Cited

U.S. PATENT DOCUMENTS

2020/0025757 A1    1/2020  Gopinath et al.
2021/0071124 A1    3/2021  Lowe, Jr. et al.
2022/0212192 A1*   7/2022  Konry .............. B01L 3/502738
2025/0129361 A1*   4/2025  Soh ...................... C12Q 1/6874

OTHER PUBLICATIONS

International Search Report and Written Opinion, PCT/US2023/061817, mailed Jul. 27, 2023.
Akbari, Ehsan, et al., "Engineering Cell Surface Function with DNA Origami," Adv. Mater., vol. 29, No. 46 (2017) (9 pages).

* cited by examiner

*Primary Examiner* — Nathan A Bowers
(74) *Attorney, Agent, or Firm* — Pabst Patent Group LLP

(57) ABSTRACT

Disclosed herein a robust approach to monitor cell interactions with its surrounding environment in real-time in a physiologically relevant 3-D microenvironment, holding great promise for enhancing future studies of detecting and monitoring cell processes and responses to instructive cues and therapeutic agents. A microfluidic cell culture system is provided that involves a cell sensor in a 3D culture scaffold and one or more microfluidic channels fluidly connected to the 3D culture matrix. The cell sensor involves a planar nucleic acid nanostructure having a top surface and a bottom surface, a plurality sensor molecule attached to the top surface to detect at least two target molecules, and one or more membrane anchoring moieties attached to the bottom surface.

15 Claims, 26 Drawing Sheets
Specification includes a Sequence Listing.

DNA ORIGAMI CELL SENSING PLATFORM

REFERENCE TO RELATED APPLICATIONS

This application claims benefit of U.S. Provisional Application No. 63/266,849, filed Jan. 17, 2022, and U.S. Provisional Application No. 63/305,778, filed Feb. 2, 2022, which are hereby incorporated herein by reference in their entireties.

SEQUENCE LISTING

This application contains a sequence listing filed in ST.26 format entitled "321501-1450 Sequence Listing" created on Dec. 14, 2022. The content of the sequence listing is incorporated herein in its entirety.

BACKGROUND OF THE INVENTION

The interactions of cells with signaling molecules in their local microenvironment maintain cells' proliferation, spatial organization, function, and fate and control disease progression such as metabolic disorders, and cancer. Understanding real-time cell interaction with extracellular ligands in a 3-D microenvironment can guide in detecting and monitoring cell processes and developing effective therapeutic agents.

SUMMARY OF THE INVENTION

Disclosed herein is a cell sensor with a planar nucleic acid nanostructure having a top surface and a bottom surface, a plurality sensor molecule attached to the top surface to detect at least two target molecules, and one or more membrane anchoring moieties attached to the bottom surface. In some embodiments, the membrane anchoring moiety has a hydrophobic anchor, such as a cholesterol.

In some embodiments, the sensor molecule is a double stranded oligonucleotide having a first strand that binds the target molecule and a second strand attached to the top surface, wherein the first strand has a quencher fluorophore and the second strand has a donor fluorophore that is quenched by the quencher fluorophore in the absence of a target molecule, wherein binding of the first strand to the target molecule displaces the quencher fluorophore from the donor fluorophore.

In some embodiments, the cell sensor has a first sensor molecule that binds a first target molecule and a second sensor molecule that binds a second target molecule, wherein the first and second sensor molecules have donor fluorophores that emit at different wavelengths, and wherein the first and second sensor molecules are present on the top surface at a ratio of 1:1.

In some embodiments, the cell sensor has a first sensor molecule that binds a first target molecule, a second sensor molecule that binds a second target molecule, and a third sensor molecule that binds a third target molecule, wherein the first, second, and third sensor molecules have donor fluorophores that emit at different wavelengths, and wherein the first, second, and third sensor molecules are present on the top surface at a ratio of 1:1:1.

In some embodiments, the cell sensor has a first sensor molecule that binds a first target molecule, a second sensor molecule that binds a second target molecule, a third sensor molecule that binds a third target molecule, and a fourth sensor molecule that binds a fourth target molecule, wherein the first, second, third, and fourth sensor molecules have donor fluorophores that emit at different wavelengths, and wherein the first, second, third, and fourth sensor molecules are present on the top surface at a ratio of 1:1:1:1.

In some embodiments, the planar nucleic acid nanostructure is a rationally designed DNA origami nanostructure. For example, in some embodiments, the DNA origami nanostructure has a top layer, a bottom layer, and optionally at least one middle layer, wherein the top layer and the bottom layer each comprise 10 or more double-stranded DNA (dsDNA) helices linearly aligned into a planar sheet. In some embodiments, the middle layer is not contiguous and comprises voids.

Also disclosed herein is a cell sensing platform wherein a cell sensor disclosed herein is integrated into the membrane of a cell. The cell can be any cell, but in particular embodiments, the cell is a cancer cell.

Also disclosed herein is a cell culture system wherein a cell disclosed herein is in a microfluidic culture system, wherein the microfluidic culture system comprises a 3D culture scaffold and one or more microfluidic channels fluidly connected to the 3D culture.

Also disclosed herein is a method for culturing cells, providing a microfluidic device comprising 3D culture scaffold, at least one inlet and at least one outlet fluidly connected to the 3D culture scaffold; seeding cells in the 3D culture scaffold; exposing the seeded cells to a flow of culture media for a period of time, and monitoring the cells for sensor binding. In some embodiments, the method further involves adding one or more target molecules to the culture media. In some embodiments, the cells are monitored for sensor binding by fluorescence microscopy.

The details of one or more embodiments of the invention are set forth in the accompanying drawings and the description below. Other features, objects, and advantages of the invention will be apparent from the description and drawings, and from the claims.

BRIEF DESCRIPTION OF FIGURES

FIG. 1A is an isometric view illustrating the structure design and locations of the top and bottom overhangs. FIG. 1B (Bottom) is a gel analysis confirming CSP structural stability after 4 h in cell culture conditions (37° C.) compared to CSP in storage buffer (left to right, 1 kb DNA ladder, the 7249 M13mp18 scaffold starting material, CSP in storage buffer, CSP in RPMI supplemented with 1 mM MgCl$_2$, CSP in RPMI supplemented with 1 mM MgCl$_2$ and 2% FBS, CSP in RPMI supplemented with 1 mM MgCl$_2$ and 8% FBS, CSP in 1×PBS, CSP in 1×PBS supplemented with 1 mM MgCl$_2$ and 2% FBS, CSP in 1×PBS supplemented with 1 mM MgCl$_2$ and 8% FBS, 1 kb DNA ladder).

FIG. 2A contains schematics of the detection of ssDNA targets on the cell membrane. CSP is incorporated into the cell membrane. The addition of DNA targets, results in the displacement of QO and high fluorescent signal. FIG. 2B contains fluorescent and DIC images representing controls and steps taken to detect target oligos on the cell membrane. I) CH12-LX cells functionalized with non-QO labeled CSP (control). II) CH12-LX cells functionalized with QO labeled CSP. III) sample in (II) after the addition of target A. IV) Sample in (II) after the addition of target B. V) Sample in (II) after the addition of both targets. VI) Sample in (I) after the addition of both targets (control). FIG. 2C shows the mean fluorescence intensity attributed to the CSP bound to the surface of 100-300 single cells was quantified based on three independent experiments for each condition. The data are expressed as mean fluorescent intensity normalized relative to the average of the mean fluorescence intensity quantified for condition I and II. FIG. 2D shows detection of target A on the membrane in real-time. DIC and fluorescent images show the increase of Cy3 signal during 10 min. FIG. 2E shows the fluorescence intensity attributed to the CSP bound to the surface of the middle cell was quantified for each time point around the membrane (DIC images were edited to remove excess background noise).

FIG. 3A contains schematic images of the microfluidic platform used for the detection. Left) Top view of the channel featuring localized region of mixture of cells and the collagen gel and the channels that will be used to apply the flow of targets. Each target channel has independent input and outlet ports, allowing the control of flow in both channels. Middle) Close-up view of boxed area in Left showing apertures that allow the connection of the target channels with cell channel. Right) Close-up view of boxed area in middle showing cells functionalized with CSP in collagen gel seeded into the middle channel of EPC. FIG. 3B contains confocal images representing cells functionalized with CSP in collagen gel seeded into the middle channel of EPC. Left) Bright field image showing cells seeded into the middle channel and one aperture connecting the middle channel to the top channel. Using confocal microscopy, the formation of collagen fibers, successful binding of CSP to the cells (red and yellow channels) and incorporation of cells into the collagen matrix is shown. FIG. 3C contains fluorescent and DIC images representing the detection of target A on the cell membrane in the collagen matrix. I: DC before the addition of target A. II: DC after the flow of target A into the collagen channel. Box plot represents the mean fluorescence intensity of 50 cells in the collagen matrix, before and after the flow of target in 5 different EPC. FIG. 3D shows detection of target A on the surface of DC in the collagen matrix in real-time. DIC and fluorescent images show the increase of Cy3 signal during 10 min (left). The average of Cy3 signal on the membrane of seven cells, seeded into three different EPC over 10 minutes. The fluorescent signal is normalized based on the average signal of all the cells at time 0 and 10 min, and the rate of photobleaching.

FIG. 11A contains representative images of functionalized CH12.LX cells with CSP or cholesterol conjugated oligonucleotide and DCs with CSP in the tissue model at time 0, 1 and 4 hours. FIG. 11B is a bar plot showing average of cell's mean fluorescent intensity normalized relative to the average of the mean fluorescence intensity at time 0 for each timepoint (CH12.LX functionalized with CCO, CH12.LX functionalized with CSP, DCs functionalized with CSP in the tissue model, scale bar: 10 um).

FIG. 12A contains representative images of functionalized CH12.LX cells with CSP, folded with only Cy3 quencher oligo, and incubated with different concentrations of DNA target. FIG. 12B is a bar plot shows average of cell's mean fluorescent intensity in Cy3 channel normalized relative to the average of the mean fluorescence intensity in Cy5 channel for each condition.

DETAILED DESCRIPTION

Figure 1A:
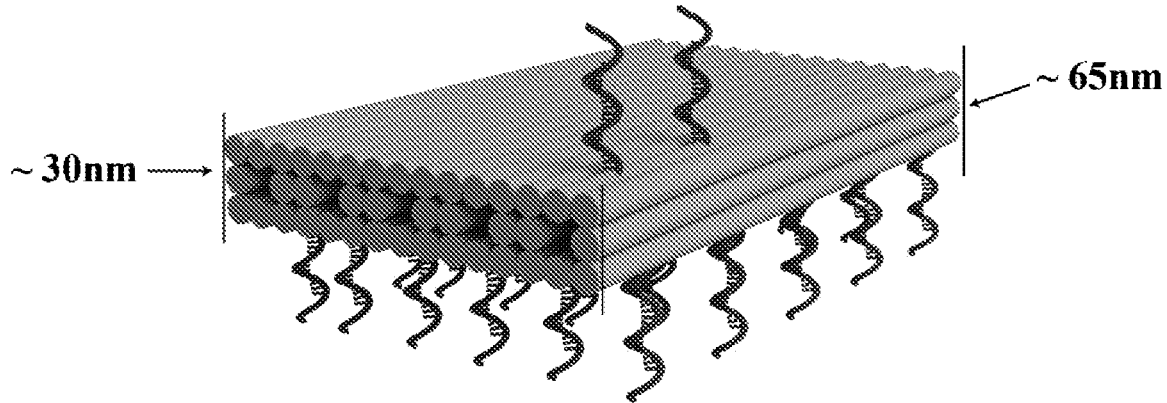
FIGS. 1A to 1 E show design and characterization of a DNA origami Cell Sensing Platform (CSP).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

DNA Origami Cell Sensing Platform (CSP)

Disclosed herein is a DNA origami Cell Sensing Platform (CSP) comprising a planar nucleic acid nanostructure having a top surface and a bottom surface. In some embodiments, membrane anchoring moieties are attached to the bottom surface in order to incorporate the CSP one the extracellular side of cell membranes. In some embodiments, one or more different sensor molecules are attached to the top surface to detect one or more target molecules interacting with the cell.

Planar Nucleic Acid Nanostructures

A "nucleic acid nanostructure," as used herein, refers to nucleic acids that form (e.g., self-assemble) two-dimensional (2D) or three-dimensional (3D) shapes (e.g., reviewed in W. M. Shih, C. Lin, Curr. Opin. Struct. Biol. 20, 276 (2010), incorporated by reference herein). Nanostructures may be formed using any nucleic acid folding or hybridization methodology. One such methodology is DNA origami (see, e.g., Rothmund, P. W. K. Nature 440 (7082): 297-302 (2006), incorporated by reference herein). In a DNA origami approach, a nanostructure is produced by the folding of a longer "scaffold" nucleic acid strand through its hybridization to a plurality of shorter "staple" oligonucleotides, each of which hybridize to two or more non-contiguous regions within the scaffold strand. In some embodiments, a staple strand may be 15 to 100 nucleotides in length. In some embodiments, a staple strand is 25 to 50 nucleotides in length.

Other methods for assembling nucleic acid nanostructures are known in the art, any one of which may be used herein. Such methods are described by, for example, Bellot G. et al., Nature Methods, 8: 192-194 (2011); Liedl T. et al, Nature Nanotechnology, 5: 520-524 (2010); Shih W. M. et al, Curr. Opin. Struct. Biol., 20: 276-282 (2010); Ke Y. et al, J. Am. Chem. Soc, 131: 15903-08 (2009); Dietz H. et al, Science, 325: 725-30 (2009); Hogberg B. et al, J. Am. Chem. Soc, 131: 9154-55 (2009); Douglas S. M. et al, Nature, 459: 414-418 (2009); Jungmann R. et al, J. Am. Chem. Soc, 130: 10062-63 (2008); Shih W. M., Nature Materials, 7: 98-100 (2008); and Shih W. M., Nature, All: 618-21 (2004), each of which is incorporated herein by reference in its entirety.

The nanostructure may have a void volume (e.g., it may be partially or wholly hollow). In some embodiments, the void volume may be at least 25%, at least 50%, at least 75%, at least 85%, at least 90%, or more of the volume of the nanostructure. Thus, in some embodiments, nucleic acid nanostructures do not comprise a solid core.

Nucleic acid nanostructures may be made of, or comprise, DNA, RNA, modified DNA, modified RNA, PNA, LNA or a combination thereof.

In some embodiments, nucleic acid nanostructures are rationally designed. A nucleic acid nanostructure is herein considered to be "rationally designed" if nucleic acids that form the nanostructure are selected based on pre-determined, predictable nucleotide base pairing interactions that direct nucleic acid hybridization. For example, nucleic acid nanostructures may be designed prior to their synthesis, and their size, shape, complexity, and modification may be prescribed and controlled using certain select nucleotides (e.g., oligonucleotides) in the synthesis process. The location of each nucleic acid in the structure may be known and provided for before synthesizing a nanostructure of a particular shape. The fundamental principle for designing, for example, self-assembled nucleic acid nanostructures is that sequence complementarity in nucleic acid strands is selected such that, by pairing up complementary segments, the nucleic acid strands self-organize into a predefined nanostructure under appropriate physical conditions. Thus, in some embodiments, nucleic acid nanostructures are self-assembling. Similarly, handles and anti-handle nucleic acids (e.g., those linked to agents or targeting molecules) may be rationally designed to attach specifically to an interior or exterior surface of a nanostructure, in some embodiments, without intercalation or hybridization with nucleic acids forming the body of the nanostructure.

As used herein, the terms "nucleic acid" and/or "oligonucleotide" may refer to at least two nucleotides covalently linked together. A nucleic acid of the present disclosure may generally contain phosphodiester bonds, although in some cases, nucleic acid analogs are included that may have other backbones, comprising, for example, phosphoramide (Beaucage et al., Tetrahedron 49(10):1925 (1993) and references therein; Letsinger, J. Org. Chem. (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. Nucleic acid may have a homogenous backbone (e.g., entirely phosphodiester or entirely phosphorothioate) or a heterogeneous (or chimeric) backbone. Phosphorothioate backbone modifications render a nucleic acid less susceptible to nucleases and thus more stable (as compared to a native phosphodiester backbone nucleic acid) under certain conditions. Other linkages that may provide more stability to a nucleic acid include without limitation phosphorodithioate linkages, methylphosphonate linkages, methylphosphorothioate linkages, boranophosphonate linkages, peptide linkages, alkyl linkages, dephospho type linkages, and the like. Thus, in some instances, nucleic acids have non-naturally occurring backbones. Modifications of the ribose-phosphate backbone may be done, for example, to facilitate the addition of labels, or to increase the stability and half-life of such molecules in physiological environments.

Nucleic acids may be single-stranded (ss) or double-stranded (ds), as specified, or may contain portions of both single-stranded and double-stranded sequence (e.g., are partially double-stranded). Nucleic acids may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, and isoguanine. As used herein, the term "nucleoside" includes nucleotides as well as nucleoside and nucleotide analogs, and modified nucleosides such as amino modified nucleosides. In addition, "nucleoside" includes non-naturally occurring analog structures. Thus, for example, the individual units of a peptide nucleic acid, each containing a base, are referred to herein as a nucleoside.

Nucleic acids include DNA such as B-form DNA, D-form DNA and L-form DNA and RNA, as well as various modifications thereof. Modifications include base modifications, sugar modifications, and backbone modifications. Non-limiting examples of these are provided below.

Non-limiting examples of DNA variants that may be used as provided herein are L-DNA (the backbone enantiomer of DNA, known in the literature), peptide nucleic acids (PNA) bisPNA clamp, a pseudocomplementary PNA, a locked nucleic acid (LNA), or co-nucleic acids of the above such as DNA-LNA co-nucleic acids. It is to be understood that nucleic acids used as provided herein may be homogeneous or heterogeneous in nature. As an example, they may be completely DNA in nature or they may comprise DNA and non-DNA (e.g., LNA) monomers or sequences. Thus, any combination of nucleic acid elements may be used. The nucleic acid modification may render the nucleic acid more stable and/or less susceptible to degradation under certain conditions. For example, in some instances, the nucleic acids are nuclease-resistant.

Methods of synthesizing nucleic acids (e.g., ssDNA or dsDNA, or ssRNA or dsRNA) are known in the art and are described, for example, in U.S. Pat. Nos. 5,143,854 and 5,445,934, herein incorporated in their entirety.

Nucleic acids may be synthesized in vitro. Methods for synthesizing nucleic acids, including automated nucleic acid synthesis, are also known in the art. Nucleic acids having modified backbones, such as backbones comprising phosphorothioate linkages, and including those comprising chimeric modified backbones may be synthesized using automated techniques employing either phosphoramidate or H-phosphonate chemistries. (F. E. Eckstein, "Oligonucleotides and Analogues—A Practical Approach" IRL Press, Oxford, U K, 1991, and M. D. Matteucci and M. H. Caruthers, Tetrahedron Lett. 21, 719 (1980)) Aryl- and alkyl-phosphonate linkages can be made, e.g., as described in U.S. Pat. No. 4,469,863; and alkylphosphotriester linkages (in which the charged oxygen moiety is alkylated), e.g., as described in U.S. Pat. No. 5,023,243 and European Patent No. 092,574, can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165; Crooke S T et al. (1996) Annu Rev Pharmacol Toxicol 36:107-129; and Hunziker J et al. (1995) Mod Synth Methods 7:331-417.

Nucleic acids may additionally or alternatively comprise modifications in their sugars. For example, a β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, arabinose, 2'-F-arabinose, 2'-O—(C1-C6)alkyl-ribose, preferably 2'-O—(C1-C6)alkyl-ribose is 2'-O-methylribose, 2'-O—(C2-C6)alkenyl-ribose, 2'-[O—(C1-C6)alkyl-O —(C1-C6)alkyl]-ribose, 2'—NH2-2'-deoxyribose, β-D-xylo-furanose, α-arabinofuranose, 2,4-dideoxy-β-D-erythro-hexo-pyranose, and carbocyclic (described, for example, in Froehler J (1992) Am Chem Soc 114:8320) and/or open-chain sugar analogs (described, for example, in Vandendriessche et al. (1993) Tetrahedron 49:7223) and/or bicyclosugar analogs (described, for example, in Tarkov M et al. (1993) Helv Chim Acta 76:481).

Nucleic acids may comprise modifications in their bases. Modified bases include modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1, 2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'-β-D-2'-deoxyribofuranosyl)-2(1H)-pyridone, and its Watson-Crick complement dP, the purine analog, is 2-amino-8-(1'-β-D-1'-deoxyribofuranosyl)-imidazo[1,2-a]-1,3,5-triazin-4(8H)-one.

In some embodiments, the DNA origami planar structure is organized into one or more layers. Therefore, in some embodiments, the DNA origami planar structure has a top layer and a bottom layer. For example, in some embodiments, the DNA origami planar structure has three layers, a top, middle, and bottom layer. In some embodiments, the middle layer(s) is not contiguous, i.e. has gaps within the layer.

In some embodiments, the top and/or bottom layers of the planar nucleic acid nanostructure involves 10 or more double-stranded DNA (dsDNA) helices linearly aligned into a planar sheet. For example, in some embodiments, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 61, 62, 64, 65, 66, 67, 68, 69, 70, 71, 72, 73, 74, 75, 76, 77. 78, 79, 80, 81, 82, 83, 84, 85, 86, 87, 88, 89, 90, 91, 92, 93, 94, 95, 96, 97, 98, 99, or 100 dsDNA are linearly aligned to form the planar sheet. Each dsDNA is approximately 2 nm in diameter. Therefore, in some embodiments, the planar structure is at about 5 to 200 nm in width, including about 10 to 100 nm in width.

In some embodiments, the planar structure has 1, 2, 3, 4, 5, 6, 7, 8, 9, 10, 11, 12, 13, 14, 15, 16, 17, 18, 19, or 20 layers. Therefore, in some embodiments, the planar structure is 2 to 100 nm thick (from top to bottom), including 2 to 20 nm or 2 to 50 nm thick, such as 2, 3, 4, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nm thick.

In some embodiments, each dsDNA helix in the planar sheet is at least about 30 to 1000 nucleotides in length, such as 30 to 500 base-pairs in length, including 30, 35, 40, 45, 60, 70, 80, 90, 100, 110, 120, 130, 140, 150, 160, 170, 180, 190, 200, 300, 400, 500, 600, 700, 800, 900, or 1000 base-pairs in length. In some embodiments, the planar structure is at about 20 to 330 nm in length, such as 20 to 170 nm in length, including 20, 25, 30, 35, 40, 45, 60, 70, 80, 90, 100, 110, 120, 130, 140, 150, 160, 170, 180, 190, 200, 210, 220, 230, 240, 250, 260, 270, 280, 290, 300, 310, 320, 330 nm in length.

In some embodiments, the planar structure is rod-shaped, i.e. longer than it is wide. In some embodiments, the planar structure is a rectangle or square shape, i.e. having the same or similar widths and lengths.

Sensors and Targeting Molecules

In some embodiments, the sensors and targeting molecules attached to the top surface are single stranded DNA (ssDNA) or RNA oligonucleotides. For example, in some embodiments, the oligonucleotides have nucleic acid sequences configured to bind a nucleic acid target. For example, the oligonucleotides may be an siRNA, shRNA, microRNA, ctDNA, antagomir, or antisense that binds a target nucleic acid molecule. In some embodiments, the oligonucleotides are DNA or RNA aptamer molecules that bind a target molecule, such as a protein or small molecule. Suitable aptamers are readily commercially available from vendors, such as example Aptagen, LLC.

The disclosed CSP technology can be used to detect any target molecule interacting with the cell. This includes molecules in the extracellular environment, molecules on other cells, or combinations thereof. For example, the target molecule can be growth factors, cytokines, immune modulators, ions, neurotransmitters, hormones, or antibodies. The target molecule can be an extracellular matrix (ECM) protein, such as a collagen, elastin, fibronectin, or laminin. For example, a CSP sensors that target extracellular growth factors can be used to study the activation and recruitment of mesenchymal stem cells by platelet-derived growth factor (PDGF).

The target molecule can be a cell surface protein, glycoprotein, such as a receptor, transporter, channel, cell-adhesion protein, or enzyme. For example, a CSP sensors that target cell surface proteins can be used to detect leukemia cells mixed with normal human bone marrow aspirates. The target molecule can be a glycoform as well. Using modified DNA aptamers functionalized with cyclooctyne, a CSP sensor can label protein glycoforms on live cells to study post-translational modification in the context of their protein scaffold In addition, a CSP sensors that target cell surface proteins can be used to target a cell to a tissue in a subject. For example, in some embodiments the cell is an immunotherapy cell, such as a TIL or CAR-T cell.

In some embodiments, the target molecule is a toxin or pathogen. For example, a CSP with toxin or pathogen sensors can be used to target E. coli bacteria, Influenza A H1N1, HIV, Enterotoxin B or study the stimulation of T lymphocyte by Superantigens.

In some embodiments, the target molecule is a drug, such as a small molecule or biologic. For example, a CSP with drug targeting sensors can be used to study drug interactions. Also, a CSP with adenine compound (such as ATP) sensor can be used to sense the extracellular chemical transmission of dynamic events on the surface of brain astrocytes.

In some embodiments, the target molecule is an ion, such a hydrogen ion. For example, a CSP with an ion sensor can be used to study ion concentrations, such as pH. CSP can be used to measure the activity and location of chloride channels and transporters and to maps the spatiotemporal changes in pH.

On some embodiments, the sensor is used to measure forces. A CSP with the force sensor can be used to measure intercellular adhesion forces, an important factor in tissue development and homeostasis.

In some embodiments binding of the sensor to a target molecule can be detected based on fluorescence resonance energy transfer (FRET) and/or involve a fluorophore/quencher pair. FRET is phenomenon known in the art wherein excitation of one fluorescent dye is transferred to another without emission of a photon. A FRET pair consists of a donor fluorophore and an acceptor (quencher) fluorophore. The fluorescence emission spectrum of the donor and the fluorescence absorption spectrum of the acceptor must overlap, and the two molecules must be in close proximity. Examples of donor fluorophores include 6-carboxyfluorescein (FAM), tetrachloro-6-carboxyfluorescein (TET), 2'-chloro-7'-phenyl-1,4-dichloro-6-carboxyfluorescein (VIC), Cy3, Alexa Fluor 555 Dye, EBFP2, ECFP, mTFP1, Alexa Fluor 488 and the like. Examples of acceptors include Cy3, Cy5, mEGFP, EYFP and mVenus and quenchers include tetra-methylcarboxyrhodamine (TAMRA) 4-(4-di methylaminophenylazo) benzoic acid ("DABCYL" or a DABCYL analog), Black Hole Black Hole Quencher®-1, Black Hole Quencher®-2, 3' Iowa Black® FQ, Iowa Black® RQ and the like. The skilled artisan will appreciate that FRET and fluorescence quenching allow for monitoring of binding of sensors to target molecules over time, providing continuous information regarding the time course of binding reactions.

Therefore, in some embodiments, the sensor comprises two oligonucleotide strands. The first strand can comprise a fluorescent donor molecule and be attached to the top surface of the nucleic acid nanostructure. The second strand can comprise a quencher and bind the target molecule. When the second strand binds the target molecule, it can be displaced and stop quenching the donor molecule on the first strand.

The fluorescent donor molecule can be embedded into the DNA nanodevice. In this configuration, the quencher molecule is bound to the device through an unlabeled DNA oligo. When the second strand binds the target molecule, it can be displaced and stop quenching the donor molecule in the device.

It is also possible to have both molecules attached to the device though one DNA oligo. In this configuration, the strand can comprise a fluorescent donor molecule and is also attached to in "intermediate DNA oligo". The third DNA oligo is modified with quencher oligo and is bound to the nanodevice thorough the intermediate oligo. In the initial configuration, the quencher and fluorescent molecule are apart from each other. When target bind to the third molecule, quencher and fluorescent molecule will be in the proximity and quenching will happen (off signal)

Membrane Anchoring Moieties

In some embodiments, the membrane-anchoring moiety is a hydrophobic anchor, such as a lipid, fatty acid, sterol, carbon nanotube, polypeptide, protein or amino acid. For example, in some embodiments, the membrane-anchoring moiety comprises a cholesterol or modified cholesterol. Cholesterol is hydrophobic, and when conjugated to oligonucleotides, can facilitate anchoring into cell membranes.

Other lipophilic moieties capable of anchoring an oligonucleotide in the lipid bi-layer membrane of a cell can also be used. In some embodiments, the membrane-anchoring moiety comprises palmitate, tocopherol, thiol, or a biotin group. In some others, the membrane-anchoring moiety is membrane-associated proteins or receptor ligands such as ephrin ligands, epidermal growth factor receptor ligand, cell adhesion peptides, e.g. RGDs.

Cells

The disclosed CSP can be incorporated into the membrane of any cell of interest. In some embodiments, said cells are selected from the group consisting of stem cells, stem cell-derived cells, cells differentiated from stem cells, and primary cells. Cells of the human body include Keratinizing Epithelial Cells, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet Stratified Barrier Epithelial Cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining bladder and urinary ducts), Exocrine Secretory Epithelial Cells, Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion), Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (HCl secretion), Pancreatic acinar cell (bicarbonate and digestive enzyme secretion), Paneth cell of small intestine (lysozyme secretion), Type II pneumocyte of lung (surfactant secretion), Clara cell of lung, Hormone Secreting Cells, Anterior pituitary cell secreting growth hormone, Anterior pituitary cell secreting follicle-stimulating hormone, Anterior pituitary cell secreting luteinizing hormone, Anterior pituitary cell secreting prolactin, Anterior pituitary cell secreting adrenocorticotropic hormone, Anterior pituitary cell secreting thyroid-stimulating hormone, Intermediate pituitary cell secreting melanocyte-stimulating hormone, Posterior pituitary cell secreting oxytocin, Posterior pituitary cell secreting vasopressin, Gut and respiratory tract cell secreting serotonin, Gut and respiratory tract cell secreting endorphin, Gut and respiratory tract cell secreting somatostatin, Gut and respiratory tract cell secreting gastrin, Gut and respiratory tract cell secreting secretin, Gut and respiratory tract cell secreting cholecystokinin, Gut and respiratory tract cell secreting insulin, Gut and respiratory tract cell secreting glucagon, Gut and respiratory tract cell secreting bombesin, Thyroid gland cell secreting thyroid hormone, Thyroid gland cell secreting calcitonin, Parathyroid gland cell secreting parathyroid hormone, Parathyroid gland oxyphil cell, Adrenal gland cell secreting epinephrine, Adrenal gland cell secreting norepinephrine, Adrenal gland cell secreting steroid hormones, Leydig cell of testes secreting testosterone, Theca interna cell of ovarian follicle secreting estrogen, Corpus *luteum* cell of ruptured ovarian follicle secreting progesterone, Kidney juxtaglomerular apparatus cell (renin secretion), Macula *densa* cell of kidney, Peripolar cell of kidney, Mesangial cell of kidney, Epithelial Absorptive Cells (Gut, Exocrine Glands and Urogenital Tract), Intestinal brush border cell (with microvilli), Exocrine gland striated duct cell, Gall bladder epithelial cell, Kidney proximal tubule brush border cell, Kidney distal tubule cell, Ductulus efferens nonciliated cell, Epididymal principal cell, Epididymal basal cell, Metabolism and Storage Cells, Hepatocyte (liver cell), White fat cell, Brown fat cell, Liver lipocyte, Barrier Function Cells (Lung, Gut, Exocrine Glands and Urogenital Tract), Type I pneumocyte (lining air space of lung), Pancreatic duct cell (centroacinar cell), Nonstriated duct cell (of sweat gland, salivary gland, mammary gland, etc.), Kidney glomerulus parietal cell, Kidney glomerulus podocyte, Loop of Henle thin segment cell (in kidney), Kidney collecting duct cell, Duct cell (of seminal vesicle, prostate gland, etc.), Epithelial Cells Lining Closed Internal Body Cavities, Blood vessel and lymphatic vascular endothelial fenestrated cell, Blood vessel and lymphatic vascular endothelial continuous cell, Blood vessel and lymphatic vascular endothelial splenic cell, Synovial cell (lining joint cavities, hyaluronic acid secretion), Serosal cell (lining peritoneal, pleural, and pericardial cavities), Squamous cell (lining perilymphatic space of ear), Squamous cell (lining endolymphatic space of ear), Columnar cell of endolymphatic sac with microvilli (lining endolymphatic space of ear), Columnar cell of endolymphatic sac without microvilli (lining endolymphatic space of ear), Dark cell (lining endolymphatic space of ear), Vestibular membrane cell (lining endolymphatic space of ear), Stria vascularis basal cell (lining endolymphatic space of ear), Stria vascularis marginal cell (lining endolymphatic space of ear), Cell of Claudius (lining endolymphatic space of ear), Cell of Boettcher (lining endolymphatic space of ear), Choroid plexus cell (cerebrospinal fluid secretion), Pia-arachnoid squamous cell, Pigmented ciliary epithelium cell of eye, Nonpigmented ciliary epithelium cell of eye, Corneal endothelial cell, Ciliated Cells with Propulsive Function, Respiratory tract ciliated cell, Oviduct ciliated cell (in female), Uterine endometrial ciliated cell (in female), Rete testis cilated cell (in male), Ductulus efferens ciliated cell (in male), Ciliated ependymal cell of central nervous system (lining brain cavities), Extracellular Matrix Secretion Cells, Ameloblast epithelial cell (tooth enamel secretion), Planum semilunatum epithelial cell of vestibular apparatus of ear (proteoglycan secretion), Organ of *Corti* interdental epithelial cell (secreting tectorial membrane covering hair cells), Loose connective tissue fibroblasts, Corneal fibroblasts, Tendon fibroblasts, Bone marrow reticular tissue fibroblasts, Other (nonepithelial) fibroblasts, Blood capillary pericyte, Nucleus pulposus cell of intervertebral disc, Cementoblast/cementocyte (tooth root bonelike cementum secretion), Odontoblast/odontocyte (tooth dentin secretion), Hyaline cartilage chondrocyte, Fibrocartilage chondrocyte, Elastic cartilage chondrocyte, Osteoblast/osteocyte, Osteoprogenitor cell (stem cell of osteoblasts), Hyalocyte of vitreous body of eye, Stellate cell of perilymphatic space of ear, Contractile Cells, Red skeletal muscle cell (slow), White skeletal muscle cell (fast), Intermediate skeletal muscle cell, Muscle spindle—nuclear bag cell, Muscle spindle—nuclear chain cell, Satellite cell (stem cell), Ordinary heart muscle cell, Nodal heart muscle cell, Purkinje fiber cell, Smooth muscle cell (various types), Myoepithelial cell of iris, Myoepithelial cell of exocrine glands, Blood and Immune System Cells, Erythrocyte (red blood cell), Megakaryocyte, Monocyte, Connective tissue macrophage (various types), Epidermal Langerhans cell, Osteoclast (in bone), Dendritic cell (in lymphoid tissues), Microglial cell (in central nervous system), Neutrophil, Eosinophil, Basophil, Mast cell, Helper T lymphocyte cell, Suppressor T lymphocyte cell, Killer T lymphocyte cell, IgM B lymphocyte cell, IgG B lymphocyte cell, IgA B lymphocyte cell, IgE B lymphocyte cell, Killer cell, Stem cells and committed progenitors for the blood and immune system (various types), Sensory Transducer Cells, Photoreceptor rod cell of eye, Photoreceptor blue-sensitive cone cell of eye, Photoreceptor green-sensitive cone cell of eye, Photoreceptor red-sensitive cone cell of eye, Auditory inner hair cell of organ of *Corti*, Auditory outer hair cell of organ of *Corti*, Type I hair cell of vestibular apparatus of ear (acceleration and gravity), Type II hair cell of vestibular apparatus of ear (acceleration and gravity), Type I taste bud cell, Olfactory neuron, Basal cell of olfactory epithelium (stem cell for olfactory neurons), Type I carotid body cell (blood pH sensor), Type II carotid body cell (blood pH sensor), Merkel cell of epidermis (touch sensor), Touch-sensitive primary sensory neurons (various types), Cold-sensitive primary sensory neurons, Heat-sensitive primary sensory neurons, Pain-sensitive primary sensory neurons (various types), Proprioceptive primary sensory neurons (various types), Autonomic Neuron Cells, Cholinergic neural cell (various types), Adrenergic neural cell (various types), Peptidergic neural cell (various types), Sense Organ and Peripheral Neuron Supporting Cells, Inner pillar cell of organ of *Corti*, Outer pillar cell of organ of *Corti*, Inner phalangeal cell of organ of *Corti*, Outer phalangeal cell of organ of *Corti*, Border cell of organ of *Corti*, Hensen cell of organ of *Corti*, Vestibular apparatus supporting cell, Type I taste bud supporting cell, Olfactory epithelium supporting cell, Schwann cell, Satellite cell (encapsulating peripheral nerve cell bodies), Enteric glial cell, Central Nervous System Neurons and Glial Cells, Neuron cell (large variety of types, still poorly classified), Astrocyte glial cell (various types), Oligodendrocyte glial cell, Lens Cells, Anterior lens epithelial cell, Crystallin-containing lens fiber cell, Pigment Cells, Melanocyte, Retinal pigmented epithelial cell, Germ Cells, Oogonium/oocyte, Spermatocyte, Spermatogonium cell (stem cell for spermatocyte), Nurse Cells, Ovarian follicle cell, Sertoli cell (in testis), and Thymus epithelial cell.

In some embodiments, the cell is a cancer cell. For example, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

Microfluidic Device

The cells with incorporated CSPs disclosed herein can be used in any culture system configured to observe the cells and sensor activation, such as fluorescence detection. For example, the cells can be cultured in a microfluidic device or chip.

For example, the microfluidic device can have a surface defining one or more microfluidic channels, wherein the surface extends beyond the one or more microfluidic channels; a three dimensional scaffold that is spatially separated from the one or more microfluidic channels. In some embodiments, the one or more microfluidic channels comprises a first microfluidic channel on a first side of the three dimensional scaffold and a second microfluidic channel on an opposite second side of the three dimensional scaffold.

In some embodiments, in embodiments having two different microfluidic channels on opposite sides of the microfluidic device, by establishing fluid flows in the two microfluidic channels that differ in their respective pressures and/or the concentrations of one or more fluid constituents (e.g., target molecule, a pharmaceutical compound, biochemical factor, etc.), a pressure and/or concentration gradient may be established across the 3D scaffolds. In certain embodiments, the two microfluidic channels may have separate or common inlets, but merge downstream the 3D scaffold to share a common outlet. As a result, the pressures in the two channels are substantially equalized, such that a pressure gradient across the 3D scaffold is avoided, as is desired for some applications. At the same time, a controlled concentration gradient can be established across the 3D scaffolds by injecting fluids of different compositions at the inlets upstream of the scaffolds.

In some embodiments, the microfluidic device may have non-uniformly treated and/or patterned interior surfaces. Surface treatment and/or patterning include chemical and/or topographical surface modifications. Chemical modifications, in turn, include treatments and/or coatings with inorganic substances as well as with organic substances (such as, e.g., antibodies or proteins). Non-uniform surface treatment implies that one or more portions of, but less than the entire, surface is treated, or that different portions are treated in different ways.

The microfluidic devices as described herein may be used for culturing and observing cells in a controlled microenvironment. Applications include, for example, cell migration, proliferation, and differentiation studies (e.g., angiogenesis investigation), and the analysis of biophysical and biochemical factor influence on cell function (including, e.g., drug safety and efficacy testing). Commercial applications of the devices described herein include, but are not limited to, evaluating cancer therapies, quantifying cancer cell migration, testing pharmaceuticals, and individualizing an anticancer treatment to a specific patient's tumor type.

The three dimensional scaffolds may include or consist essentially of a gel matrix, which may comprise a gel or gel-like material such as, e.g., collagen, fibronectin, hyaluronan, a hydrogel (such as, e.g., polyethylene glycol hydrogel), a peptide gel, or gel-like proteins or protein mixtures secreted by animal cells (e.g., Matrigel™) as well as inter-penetrating network hydrogels. Non-limiting examples of polymers that can be used to construct the disclosed microfluidic devices include polystyrene, polydimethylsiloxane, polycarbonate, poly(methyl methacrylate), cyclic olefin copolymer, polyethylene, polyethylene terephthalate, polyurethane, polycaprolactone, polylactic acid, polyglycolic acid, or poly(lactic-co-glycolic acid). In some embodiments, different types of polymers are used for different components or portions of the polymer structure. The polymer structure may be substantially optically transparent (e.g., have a transmission in the visible range of more than 70%, preferably more than 90%, and more preferably more than 95%).

Also disclosed herein a method of culturing cells that involves: providing a microfluidic device comprising 3D culture scaffold, at least one inlet and at least one outlet fluidly connected to the 3D culture scaffold; seeding cells in the 3D culture scaffold; exposing the seeded cells to a flow of culture media for a period of time (e.g. 4, 7, 10, 12, 20, 24, 30, 36 or more days), and monitoring the cells for sensor binding. In some embodiments, the method further involves adding one or more target molecules to the culture media.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Abstract

The interactions of cells with signaling molecules present in their local microenvironment maintain cell proliferation, differentiation, and spatial organization, and mediate progression of diseases such as metabolic disorders and cancer. Real-time monitoring of the interactions between cells and their extracellular ligands in a 3-D microenvironment can inform detection and understanding of cell processes and development of effective therapeutic agents. DNA-origami technology allows for the design and fabrication of biocompatible and 3-D functional nanodevices via molecular self-assembly for various applications including molecular sensing. Here, a robust method to monitor live cell interactions with molecules in their surrounding environment in a 3-D tissue model using a microfluidic device is reported. A DNA origami Cell Sensing Platform (CSP) was used to detect two specific nucleic acid sequences on the membrane of B cells and dendritic cells. Real-time detection of biomolecules with the DNA sensing platform on the surface of dendritic cells was further demonstrated in a 3-D microfluidic tissue model. These results establish the integration of live cells with membranes engineered with DNA nanodevices into microfluidic chips as a highly capable biosensor approach to investigate subcellular interactions in physiologically relevant 3-D environments under controlled biomolecular transport.

Introduction

Living cells interact with a myriad of extracellular signaling molecules, such as nucleic acids, growth factors, and cytokines. For instance, antigen-presenting dendritic cells (DC) are activated by cytokines in the local environment, leading to their secretion of pro-inflammatory cytokines, activation of T-cells, and regulation of immune response and homeostasis (Blanco, P. et al, Cytokine Growth Factor Rev. 2008, 19:41). DCs also respond to extracellular microRNAs (miRNAs) and tumor-secreted DNA, to modulate immune responses in cancer and other diseases (Liang, H. et al, ExRNA 2019, 1:9; Ranganathan, P. et al, J. Immunol. 2017, 198:2500; Kang, T. H. et al, J. Immunother. Cancer 2019, 7:260). Yet, understanding of interactions between cells and extracellular ligands, especially in native 3-D tissue environments, remains incomplete. Many cellular responses to external cues occur rapidly and are contingent on the spatial context of the signals (e.g., molecular gradients) within the local milieu. Therefore, improvements in cell-based biosensor technologies with dynamic subcellular readouts and improved spatiotemporal resolution are needed to improve understanding of cell interactions with extracellular signaling molecules in their microenvironment. Thus, the goal of this work was to develop a robust approach to monitor cell interactions with the surrounding environment in real-time in a physiologically relevant 3-D microenvironment, which would enhance studies focused on understanding cell biology and developing effective therapeutics.

Many of the conventional molecular biochemistry assays to characterize cell interactions, such as flow cytometry, enzyme-linked immunosorbent assay (ELISA), immunostaining, and polymerase chain reaction (PCR), focus on measuring the presence of specific molecular markers that are indicative of a cell response (e.g. membrane receptors, mRNA, or activated signaling molecules). However, they require staining, washing, and manipulation before imaging and only provide end-point results. These methods are further constrained by requiring the measurement of many cells as opposed to single cell analysis. They also, do not provide a direct indication of the extracellular ligand that leads to cell activation (only measure cell response), and hence, fail to monitor interactions at the cell-surface in real-time. More recent studies have engineered cell surfaces with synthetic probes (Laughlin, S. T. et al, Science (80-.). 2008, 320:664; Amaral, A. J. R. et al, Acta Biomater. 2019, 90:21), labeled proteins (Giepmans, B. N. G. et al, Science. 2006, 312:217), or fluorescent DNA constructs (Zhao, W. et al, Nat. Nanotechnol. 2011, 6:524). These advances have allowed for improved capabilities for measurements at the single cell level (Lun, X. K. et al, Mol. Cell. Proteomics 2020, 19:744), but they still are only capable of understanding cell interactions with a single target molecule and cannot monitor the interaction of cell membranes with multiple biomolecules.

Cell interactions are highly affected by their microenvironments, including the physical and biochemical properties of the surrounding extracellular matrix (ECM) (Muncie, J. M. et al, Curr. Top. Dev. Biol. 2018, 130:1; Beshay, P. E. et al, Adv. NanoBiomed Res. 2022, 2:2100056). Living systems are complex and difficult to control and interrogate efficiently at cellular length scales making it difficult to study detailed mechanisms efficiently in animal models. 3-D tissue models are useful surrogates for animal models that recapitulate key aspects of living tissues while enabling control over the environment with simpler measurement readouts; hence these are useful systems to study underlying mechanisms of cell response in physiologically relevant microenvironment. Although prior work has demonstrated that engineered cells with sensing capabilities can be monitored in live animal models (Laughlin, S. T. et al, Science. 2008, 320:664; Zhao, W. et al, Nat. Nanotechnol. 2011, 6:524), they have not yet been widely deployed in reconstituted 3-D tissue models, which provide simpler measurement readouts and control over the microenvironment composition. The incorporation of cells engineered with molecular detection capabilities into 3-D tissue models would enable novel insights into the spatiotemporal effects of soluble signals and intercellular communication, including mechanisms that mediate disease progression.

Structural DNA nanotechnology (Seeman, N. C. J. Theor. Biol. 1982, 99:237) has emerged as a versatile approach to make biocompatible nanodevices with precise structure that can be functionalized with a large range of molecules, making them attractive for biological applications, including engineering cell membranes (Huo, S. et al, Adv. Sci. 2019, 6:1900043). The molecular self-assembly process known as DNA-origami (Rothemund, P. W. K. Nature 2006, 440:297) allows for programming complex nanoscale geometry (Castro, C. E. et al, Nat. Methods 2011, 8:221; Douglaset S. M. al, Nature 2009, 459:414), tunable mechanical and dynamic properties (Marras, A. E. et al, Proc. Natl. Acad. Sci. U.S.A 2015, 112:713; Zhou, L. et al, ACS Nano 2014, 8:27; Hudoba, M. W. et al, ACS Nano 2017, 11:6566), and the incorporation of one or many molecules with nanometer precision (Akbari, E. et al, Adv. Mater. 2017: 29; Le, J. V. et al, ACS Nano 2016, 10, 7073; Ding, B. et al, J. Am. Chem. Soc. 2010, 132, 3248; Chhabra, R. et al, J. Am. Chem. Soc. 2007, 129:10304; Maune, H. T.et al, Nat. Nanotechnol. 2010, 5:61; Bui, H. et al, Nano Lett. 2010, 10:3367). DNA origami nanodevices have been recently used in applications including drug delivery (Douglas, S. M. et al, Science 2012:335, 831; Zhang, Q. et al, ACS Nano 2014, 8:6633; Zhao, Y.-X. et al, ACS Nano 2012, 6:8684; Halley, P. D. et al, Small 2016, 12:308), ion and molecular transport (Langecker, M. et al, Science. 2012, 338:932; Burns, J. R. et al, Nat. Nanotechnol. 2016, 11:15), imaging (Jungmann, R. et al, Nat. Methods 2014, 11:313), as well as molecular sensing, manipulation, and measurement (Le, J. V. et al, ACS Nano 2016, 10, 7073; Wang, D. et al, Anal. Chem. 2014, 86:1932; Nickels, P. C. et al, Science. 2016, 354:305). In addition, 3-D DNA nanodevices were successfully incorporated into the cell membranes to control adhesion between two living cells (Akbari, E. et al, Adv. Mater. 2017: 29), and facilitate cell-cell communication (Li, et al, J. Am. Chem. Soc. 2019, 141:18013), and other advanced functions like membrane sculpting (Franquelim, H. G. et al, Nat. Commun. 2018, 9:811) or cargo transport (Rubio-Sánchez, R. et al, Nano Lett. 2021, 21:2800) have been demonstrated on synthetic membranes. While these nanodevices have been used in a variety of biological assays including cell culture (Halley, P. D. et al, Small 2016, 12:308), cell spheroids (Wang, Y. et al, Adv. Mater. 2021, 33:2008457), and animal models (Zhang, Q. et al, ACS Nano 2014, 8:6633), they have not been implemented into 3-D ECM model systems, which are ideal for probing biological mechanisms in native tissue environments.

Here, a method was established to sense multiple biomolecules on the membrane of living cells in a 3D tissue model. a DNA origami Cell Sensing Platform (CSP) capable of detecting the presence of two specific molecules was designed. A focus was placed on detecting nucleic acid sequences on the surfaces of both CH12-LX B cells (suspension) and MutuDC 1949 dendritic cells (adherent) with fluorescence-based reporting both in cell culture and in 3-D collagen matrices. Using microfluidics to control the ECM structure formation and the localized transport of target molecules, it was shown how multifunctional DNA origami devices can be used to probe the temporal interactions of cells and their local environment with subcellular resolution in a tissue model system.

Living cells interact with a myriad of extracellular signaling molecules, such as nucleic acids, growth factors, and cytokines. For instance, antigen-presenting dendritic cells (DC) are activated by cytokines in the local environment, leading to their secretion of pro-inflammatory cytokines, activation of T-cells, and regulation of immune response and homeostasis (Blanco, P. et al, Cytokine Growth Factor Rev. 2008, 19:41). DCs also respond to extracellular microRNAs (miRNAs) and tumor-secreted DNA, to modulate immune responses in cancer and other diseases (Liang, H. et al, ExRNA 2019, 1:9; Ranganathan, P. et al, J. Immunol. 2017, 198:2500; Kang, T. H. et al, J. Immunother. Cancer 2019, 7:260). Yet, understanding of interactions between cells and extracellular ligands, especially in native 3-D tissue environments, remains incomplete. Many cellular responses to external cues occur rapidly and are contingent on the spatial context of the signals (e.g., molecular gradients) within the local milieu. Therefore, improvements in cell-based biosensor technologies with dynamic subcellular readouts and improved spatiotemporal resolution are needed to improve understanding of cell interactions with extracellular signaling molecules in their microenvironment. Thus, the goal of this work is to develop a robust approach to monitor cell interactions with the surrounding environment in real-time in a physiologically relevant 3-D microenvironment, which would enhance studies focused on understanding cell biology and developing effective therapeutics.

Many of the conventional molecular biochemistry assays to characterize cell interactions, such as flow cytometry, enzyme-linked immunosorbent assay (ELISA), immunostaining, and polymerase chain reaction (PCR), focus on measuring the presence of specific molecular markers that are indicative of a cell response (e.g. membrane receptors, mRNA, or activated signaling molecules). However, they require staining, washing, and manipulation before imaging and only provide end-point results. These methods are further constrained by requiring the measurement of many cells as opposed to single cell analysis. They also, do not provide a direct indication of the extracellular ligand that leads to cell activation (only measure cell response), and hence, fail to monitor interactions at the cell-surface in real-time. More recent studies have engineered cell surfaces with synthetic probes (Laughlin, S. T. et al, Science. 2008, 320:664; Amaral, A. J. R. et al, Acta Biomater. 2019, labeled proteins (Giepmans, B. N. G. et al, Science. 2006, 312:217), or fluorescent DNA constructs (Zhao, W. et al, Nat. Nanotechnol. 2011, 6:524). These advances have allowed for improved capabilities for measurements at the single cell level (Lun, X. K. et al, Mol. Cell. Proteomics 2020, 19:744), but they still are only capable of understanding cell interactions with a single target molecule and cannot monitor the interaction of cell membranes with multiple biomolecules.

Cell interactions are highly affected by their microenvironments, including the physical and biochemical properties of the surrounding extracellular matrix (ECM) (Muncie, J. M. et al, Curr. Top. Dev. Biol. 2018, 130:1; Beshay, P. E. et al, Adv. NanoBiomed Res. 2022, 2:2100056). Living systems are complex and difficult to control and interrogate efficiently at cellular length scales making it difficult to study detailed mechanisms efficiently in animal models. 3-D tissue models are useful surrogates for animal models that recapitulate key aspects of living tissues while enabling control over the environment with simpler measurement readouts; hence these are useful systems to study underlying mechanisms of cell response in physiologically relevant microenvironment. Although prior work has demonstrated that engineered cells with sensing capabilities can be monitored in live animal models (Laughlin, S. T. et al, Science. 2008, 320:664; Zhao, W. et al, Nat. Nanotechnol. 2011, 6:524), they have not yet been widely deployed in reconstituted 3-D tissue models, which provide simpler measurement readouts and control over the microenvironment composition. The incorporation of cells engineered with molecular detection capabilities into 3-D tissue models would enable novel insights into the spatiotemporal effects of soluble signals and intercellular communication, including mechanisms that mediate disease progression.

Structural DNA nanotechnology (Seeman, N. C. J. Theor. Biol. 1982, 99:237) has emerged as a versatile approach to make biocompatible nanodevices with precise structure that can be functionalized with a large range of molecules, making them attractive for biological applications, including engineering cell membranes (Huo, S. et al, Adv. Sci. 2019, 6:1900043). The molecular self-assembly process known as DNA-origami (Rothemund, P. W. K. Nature 2006, 440:297) allows for programming complex nanoscale geometry (Castro, C. E. et al, Nat. Methods 2011, 8:221; Douglaset S. M. al, Nature 2009, 459:414), tunable mechanical and dynamic properties (Marras, A. E. et al, Proc. Natl. Acad. Sci. U.S.A 2015, 112:713; Zhou, L. et al, ACS Nano 2014, 8:27; Hudoba, M. W. et al, ACS Nano 2017, 11:6566), and the incorporation of one or many molecules with nanometer precision (Akbari, E. et al, Adv. Mater. 2017:29; Le, J. V. et al, ACS Nano 2016, 10, 7073; Ding, B. et al, J. Am. Chem. Soc. 2010, 132:3248; Chhabra, R. et al, J. Am. Chem. Soc. 2007, 129:10304; Maune, H. T.et al, Nat. Nanotechnol. 2010, 5:61; Bui, H. et al, Nano Lett. 2010, 10:3367). DNA origami nanodevices have been recently used in applications including drug delivery (Douglas, S. M. et al, Science 2012:335, 831; Zhang, Q. et al, ACS Nano 2014, 8:6633; Zhao, Y.-X. et al, ACS Nano 2012, 6:8684; Halley, P. D. et al, Small 2016, 12:308), ion and molecular transport (Langecker, M. et al, Science. 2012, 338:932; Burns, J. R. et al, Nat. Nanotechnol. 2016, 11:15), imaging (Jungmann, R. et al, Nat. Methods 2014, 11:313), as well as molecular sensing, manipulation, and measurement (Le, J. V. et al, ACS Nano 2016, 10, 7073; Wang, D. et al, Anal. Chem. 2014, 86:1932; Nickels, P. C. et al, Science. 2016, 354:305). In addition, 3-D DNA nanodevices were successfully incorporated into the cell membranes to control adhesion between two living cells (Akbari, E. et al, Adv. Mater. 2017: 29), and facilitate cell-cell communication (Li, et al, J. Am. Chem. Soc. 2019, 141:18013), and other advanced functions like membrane sculpting (Franquelim, H. G. et al, Nat. Commun. 2018, 9:811) or cargo transport (Rubio-Sanchez, R. et al, Nano Lett. 2021, 21:2800) have been demonstrated on synthetic membranes. While these nanodevices have been used in a variety of biological assays including cell culture (Halley, P. D. et al, Small 2016, 12:308; Schüller, V. J. et al, ACS Nano 2011, 5:9696), cell spheroids (Wang, Y. et al, Adv. Mater. 2021, 33:2008457), and animal models (Zhang, Q. et al, ACS Nano 2014, 8:6633), they have not been implemented into 3-D ECM model systems, which are ideal for probing biological mechanisms in native tissue environments.

Here, a method is established to sense multiple biomolecules on the membrane of living cells in a 3D tissue model. a DNA origami Cell Sensing Platform (CSP) capable of detecting the presence of two specific molecules was designed. A focus was placed on detecting nucleic acid sequences on the surfaces of both CH12-LX B cells (suspension) and MutuDC 1949 dendritic cells (adherent) with fluorescence-based reporting both in cell culture and in 3-D collagen matrices. Using microfluidics to control the ECM structure formation and the localized transport of target molecules, we show how multifunctional DNA origami devices can be used to probe the temporal interactions of cells and their local environment with subcellular resolution in a tissue model system.

Results

A Stable DNA Origami Device Detects Multiple Targets

Figure 1B:
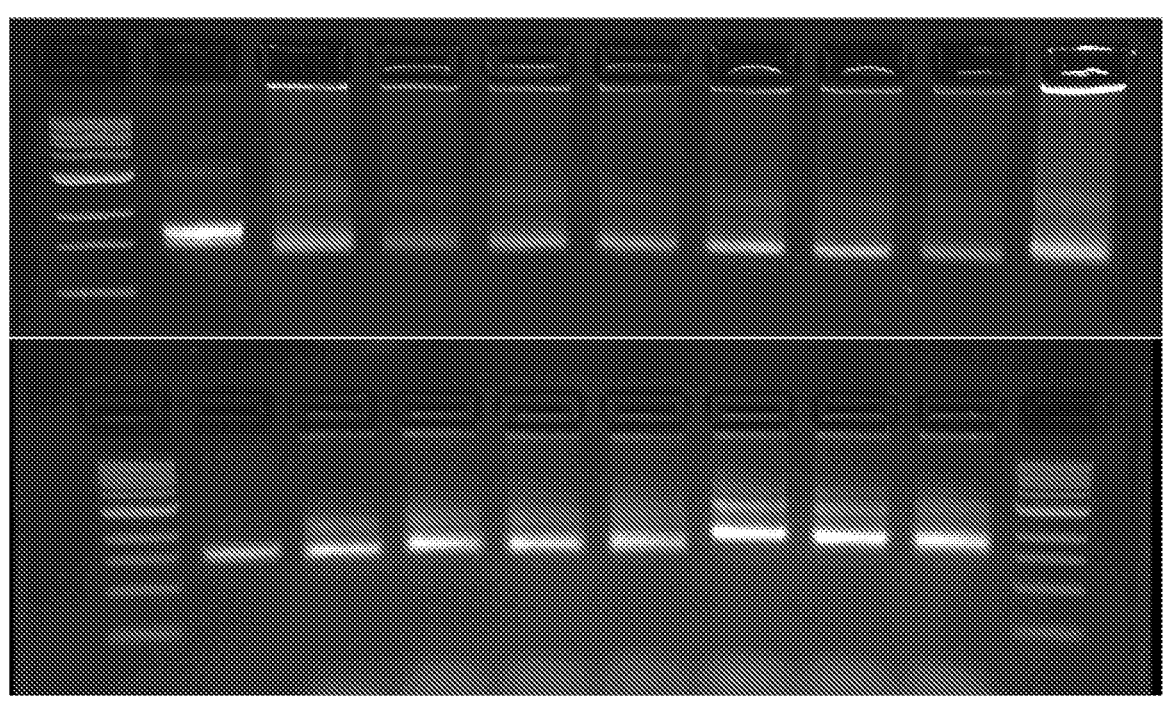
FIG. 1B (Top) is a gel analysis confirming the structure folding using 4 hours isothermal annealing protocol (left to right, 1 kb DNA ladder (L), the 7249 M13mp18 scaffold starting material, and folded CSP form 60 (left) to 40 degrees (right)).
Figure 1C:
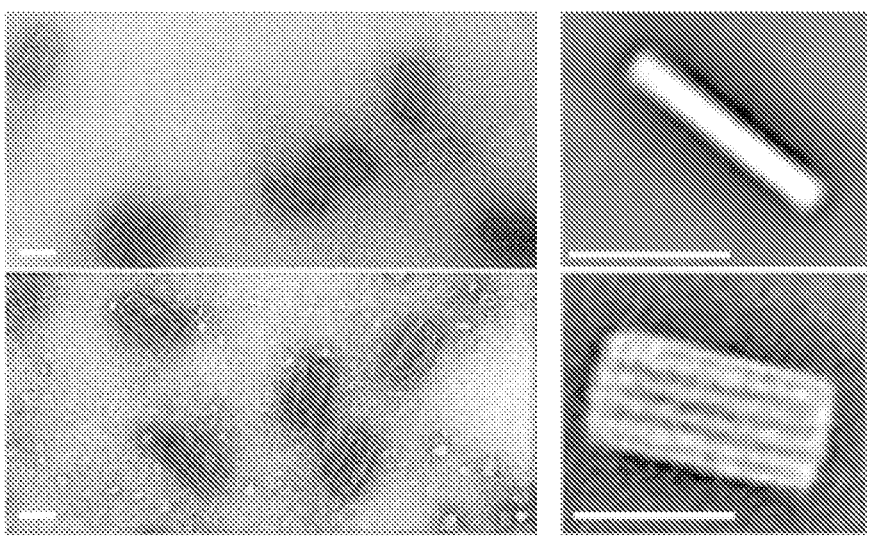
FIG. 1C shows TEM images confirming the structure is preserved after incubation under cell culture conditions for 4 h in storage buffer (top left) and RPMI supplemented with 2% FBS and 1 mM Mg$^2$+(bottom left). Image averages of CSP in storage buffer using ImageJ are shown in the right. (Scale bar: 50 nm) FIG. 1D contains 2D schematics of CSP from the top with DNA detection modules on C3 and C4 locations. Before the introduction of DNA targets, quenching oligo is bound to the respective top overhangs, placing the quencher in the proximity of fluorophore, leading to a low fluorescent signal. After the addition of DNA targets, the quenching oligo is displaced with the target oligo, resulting in a high fluorescent signal (shown in FIG. 1E, dashed lines).
Figure 1D:
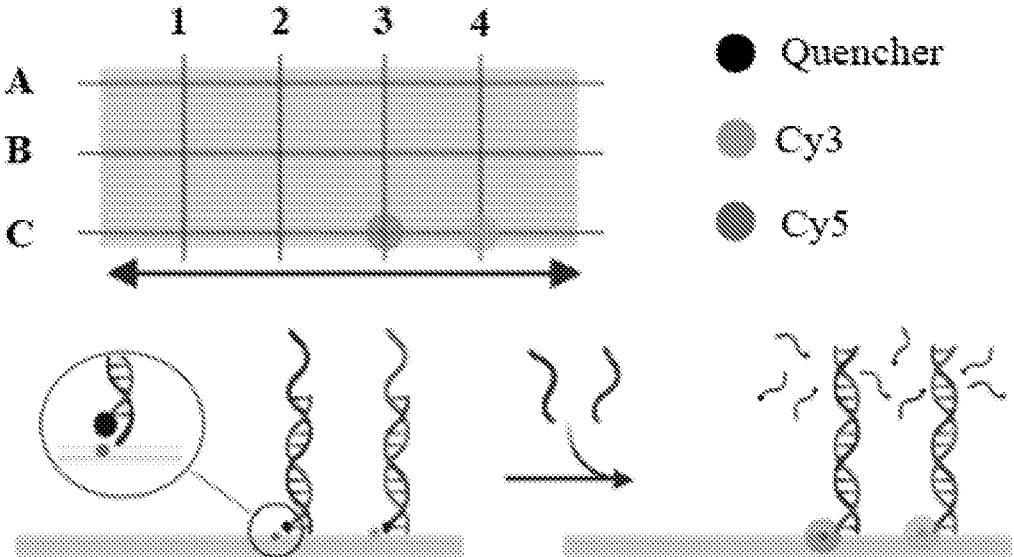
FIG. 1E contains fluorometer data showing the fluorescent signal of CSP folded with quenching oligo (dark solid lines), folded without the quenching oligo (light solid line) and ones with quenching oligo after the addition of target oligo (dashed lines).
Figure 6:
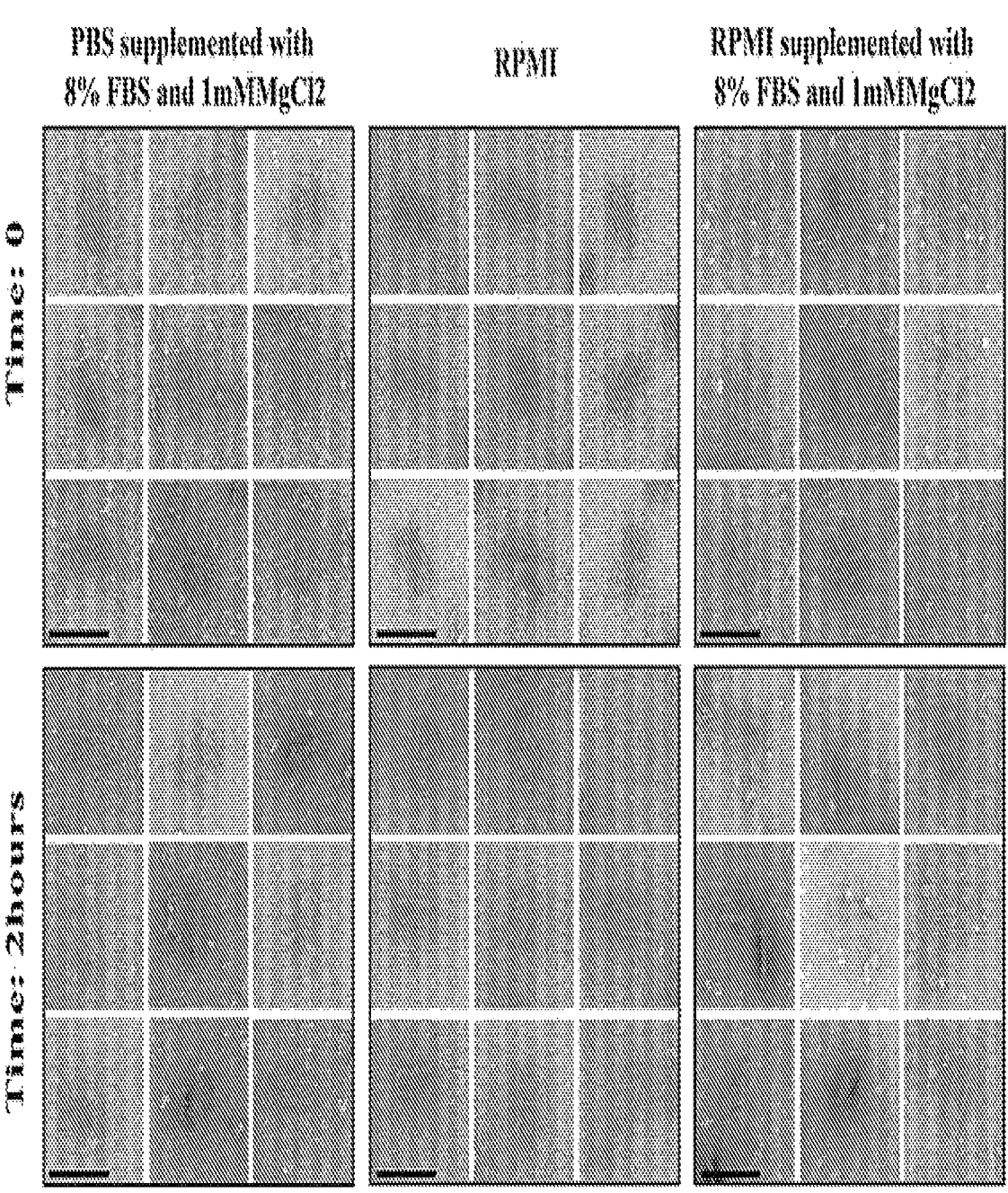
FIG. 6 shows the stability analysis of CSP under difference cell culture media conditions using TEM. The nanostructures were incubated in each corresponding cell culture media at 37° C. for 4 hours and then gel purified (Scale bar: 100 nm).
Figure 7:
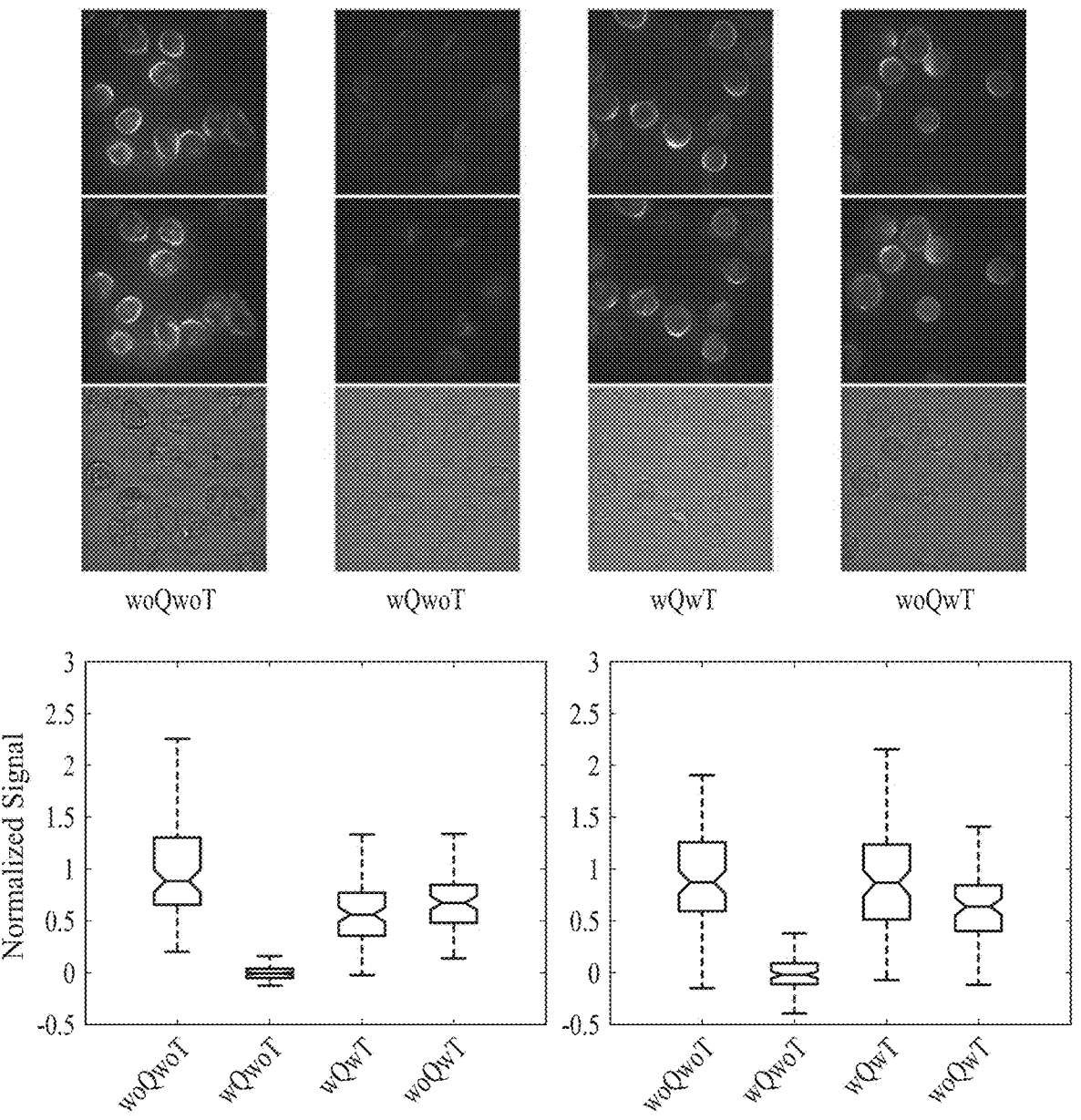
FIG. 7 shows detection of ssDNA targets on dendritic cells in suspension. Top) Fluorescent and DIC images representing controls and steps taken to detect target oligos on the cell membrane. woQwoT) Dendritic cells functionalized with non-QO labeled CSP (control). wQwoT) Dendritic cells functionalized with QO labeled CSP. wQwT) wQwoT samples after the addition of both ssDNA targets. woQwT) woQwoT samples after the addition of both targets (control). Bottom) The mean fluorescence intensity attributed to the CSP bound to the surface of 80-100 single cells was quantified based on two independent experiments for each condition. The data are expressed as mean fluorescent intensity normalized relative to the average of the mean fluorescence intensity quantified for woQwoT and wQwoT conditions.
Figure 10:
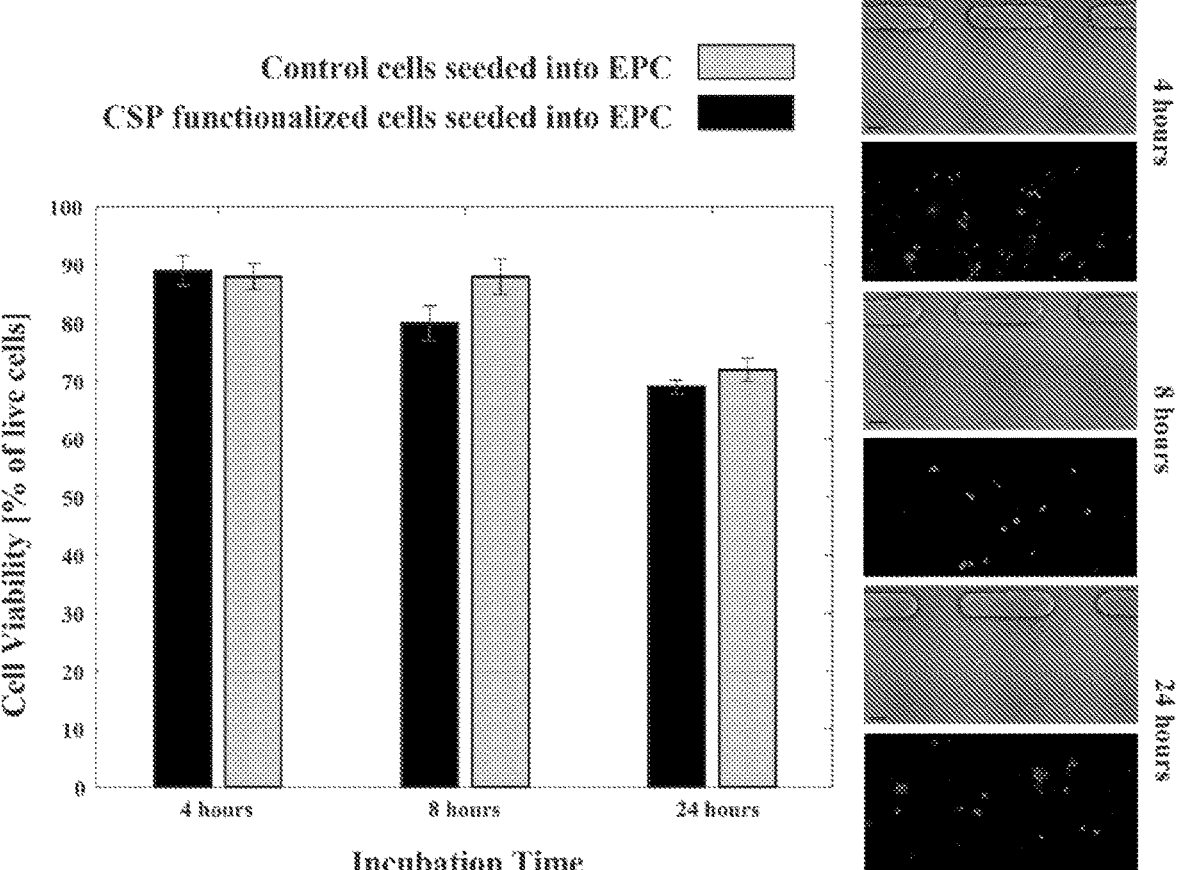
FIG. 10 shows dendritic cells viability when functionalized with CSP nanodevices and seeded into the EPC device. Left) Quantitative analysis of viability rate of DCs, functionalized with non-labeled CSP nanodevices and incubated for 4 to 24 hours in the collagen matrix, compared with control cells incubated in the same condition. Right) Confocal images of DCs depicting the live and dead cells in the microfluidic device after 4, 8 and 24 hours. [Live cells; all cells] Scale bars are 50 μm. The cell viability values are presented as the mean±the standard error of the mean for each experimental test condition tested in 2 separate microfluidic devices as replicates.

The CSP structure was designed using the DNA design software caDNAno (Douglas, S. M. et al, Nucleic Acids Res. 2009, 37:5001). The structure consists of 40 double-stranded DNA (dsDNA) helices organized into three layers with gaps in the middle layer (FIG. 1A), inspired by a prior nanorod design that exhibited efficient folding and robust stability in cell culture media (Halley, P. D. et al, Small 2016, 12:308). The full caDNAno design and corresponding oligonucleotide sequences are provided in FIG. 4 and Table 1. The CSP design allows for the selective incorporation of up to 30 single-stranded DNA (ssDNA) overhangs on the membrane-facing side (bottom overhangs) and up to 12 overhangs on the membrane-opposing side (top overhangs) (FIGS. 1A and 1D). To ensure proper molecular self-assembly and optimize the ion concentration and isothermal annealing temperature (Sobczak, J.-P. J. et al, Science 2012, 338:1458), CSP was subjected to thermal annealing by rapid heating to 65° C. followed by slow cooling to 4° C. over 2.5 d in different $MgCl_2$ concentrations (10 to 24 mM). Gel electrophoresis confirmed folding of CSP in a wide range of 14 to 24 mM $MgCl_2$ (FIG. 6A). 18 mM was chosen for subsequent folding. Self-assembled nanostructures were then folded at various isothermal annealing temperatures in 18 mM $MgCl_2$ over 4 hours and subjected to agarose gel electrophoresis. Gel electrophoresis revealed the successful folding of CSP over the annealing temperature range of 42 to 59° C. (FIG. 6B). 52° C. was chosen for subsequent folding with isothermal annealing. To ensure that the structural integrity is preserved in cell culture media, the stability of CSP was tested in RPMI 1640 cell culture medium supplemented with 2% FBS and 1 mM $MgCl_2$ after 4 hours incubation in 37° C. via agarose gel electrophoresis. FIG. 1B shows that CSP nanostructures remained intact under each cell culture media conditions compared to the control structures in storage buffer, 1× FOB solution (5 mM Tris, 5 mM NaCl, 1 mM EDTA) supplemented with 10 mM $MgCl_2$. The slight differences in the migration speed is likely due to the different buffer conditions. Leading bands were excised and visualized using transmission electron microscopy (TEM) to confirm that CSP preserved its structural integrity in cell culture media (FIGS. 10 and 7).

The CSP enables incorporation of up to 12 top overhangs (FIG. 1D) which could potentially allow for 12 distinct detection sites for various biomolecular targets. Here, to enable the detection of two distinct DNA target strands, two overhangs with unique sequences were incorporated at locations 3C and 4C onto the CSP. Two Quencher-labeled oligonucleotides (QO) complementary to each of the top overhangs were designed to provide a 5-base pair toehold for the binding of target oligos (FIG. 1D). Moreover, one Cy3-labeled oligonucleotide and one Cy5-labeled oligonucleotide were incorporated into the CSP platform to create the two-channel internally labeled CSP. The Cy3 and Cy5 oligonucleotides were incorporated so that the Cy3 molecule is proximal to the quencher at the 4C overhang location, and the Cy5 is proximal to the quencher at the 3C overhang location (FIG. 1D). Thus, the Cy3 and Cy5 are quenched in the initial configuration, and hence emit a low fluorescent signal (Cy3 dark green and Cy5 dark red in FIG. 1E). The addition of the target DNA strands causes the QO strands to be removed via toehold mediated strand displacement (Yurke, B. et al, Nature 2000, 406:605) (FIG. 1D). After target A (DNA target corresponding to Cy3 channel) displaces the QO, the Cy3 molecule emits higher fluorescent signal as is shown with the dashed green spectra in FIG. 1E.

Figure 1E:
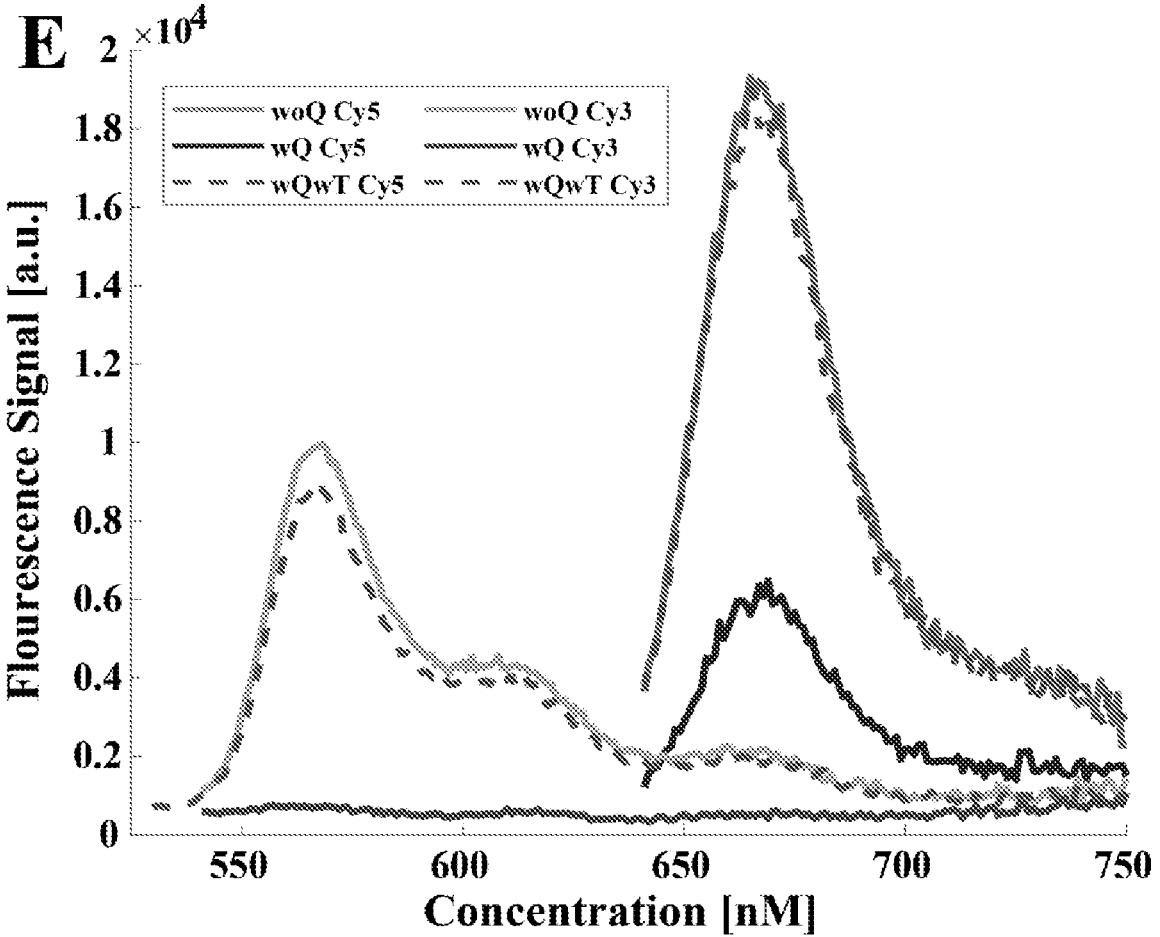

The Cy3 fluorescent signal of the CSP folded without the quenching oligo was also shown as a control to display the maximum fluorescent signal (light green spectra in FIG. 1E). The design principles are the same for the Cy5-labeled oligo and 3C overhang. The Cy5 fluorescent signal is low before the addition of target B (DNA target corresponding to Cy5 channel) as shown with solid dark red spectra in FIG. 1E. Incubation of target B with the CSP causes strand displacement and an increase in the Cy5 fluorescent signal (dashed red spectra in FIG. 1E). The light red spectra in FIG. 1E shows the Cy5 signal from the CSP folded without QO, as the control showing essentially all quencher strands are displaced.

CSP Detects DNA Targets on the Cell Membrane

Figure 2A:
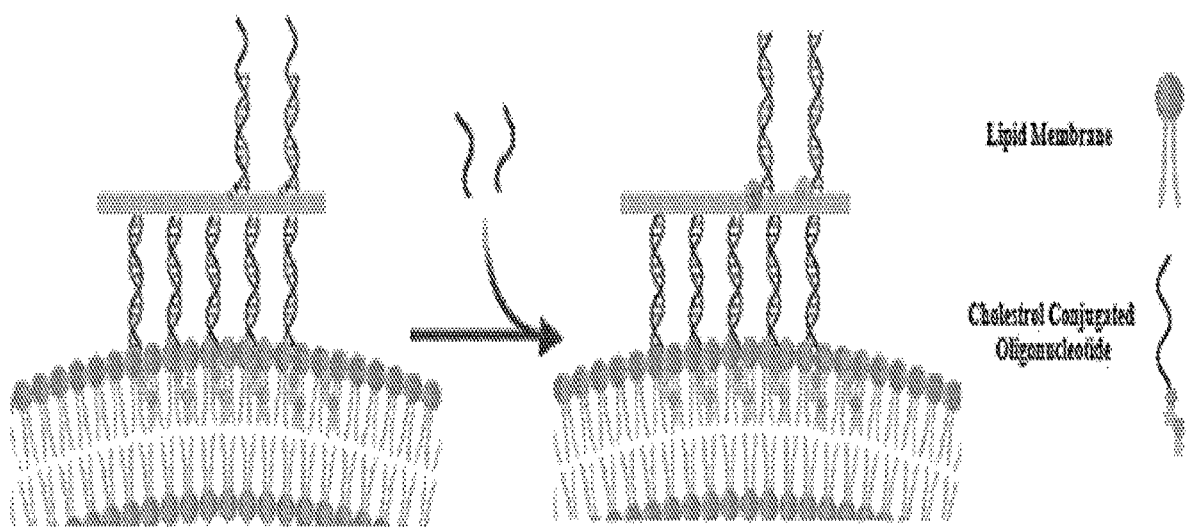
FIGS. 2A to 2E show detection of ssDNA targets on CH12-LX suspension cells.
Figure 2B:
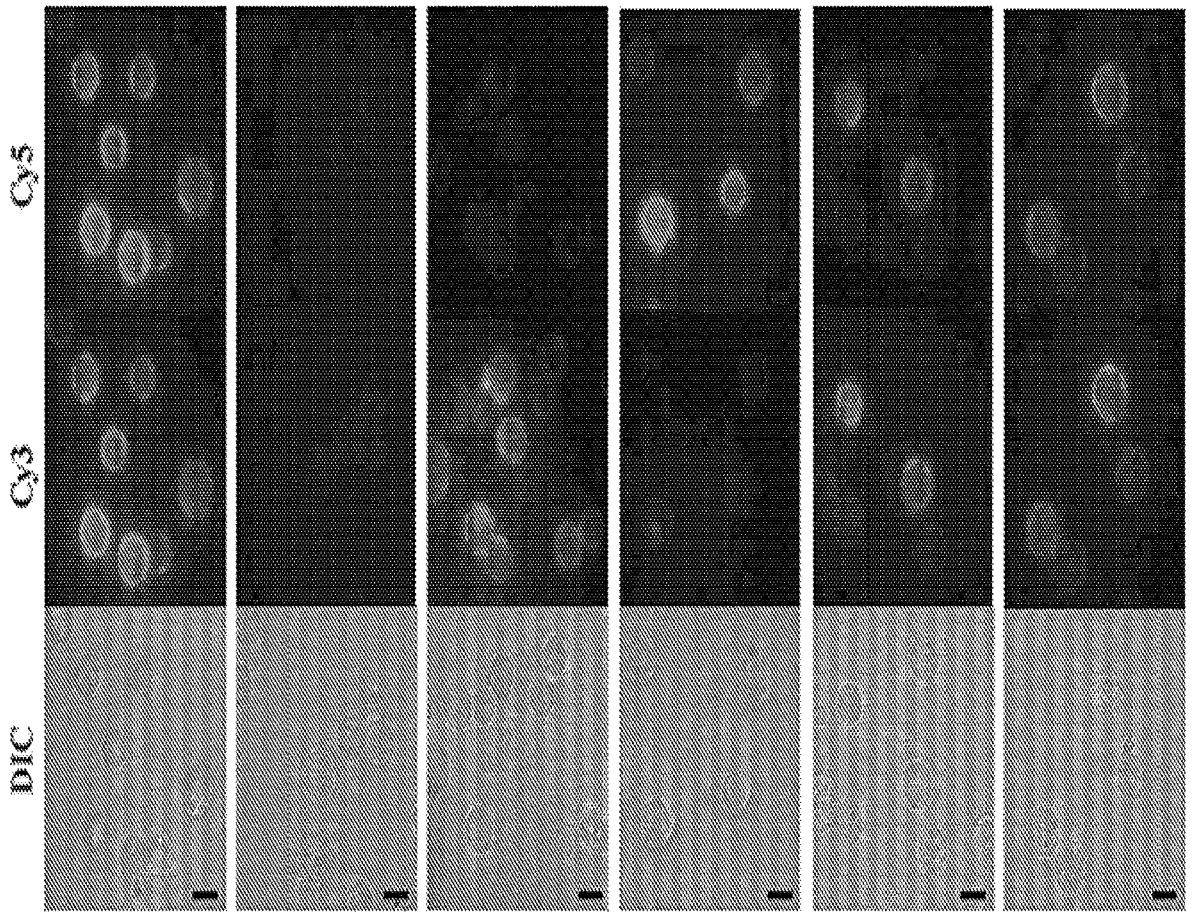

To detect DNA targets on the membrane of living cells, the CSP was incorporated onto the extracellular side of cell membranes using cholesterol-conjugated-oligonucleotides based on a previously published method (Akbari, E. et al, Adv. Mater. 2017: 29) (FIGS. 2A and 7). The functionalized cells with CSP were immobilized on a glass chamber and either imaged directly using epifluorescence microscopy or imaged after introducing 1 µM target nucleic acid strands into solution and incubating for 15 min at 37° C. Representative fluorescent images in FIG. 2B show: I) cells functionalized with non-QO labeled CSP, II) cells functionalized with QO labeled CSP, Ill) cells with QO labeled CSP after incubation with target A, IV) cells with QO labeled CSP after incubation with target B, V) cells in with QO labeled CSP after incubation with both DNA targets, and VI) cells functionalized with non-QO labeled CSP after incubation with both DNA targets.

Figure 2C:
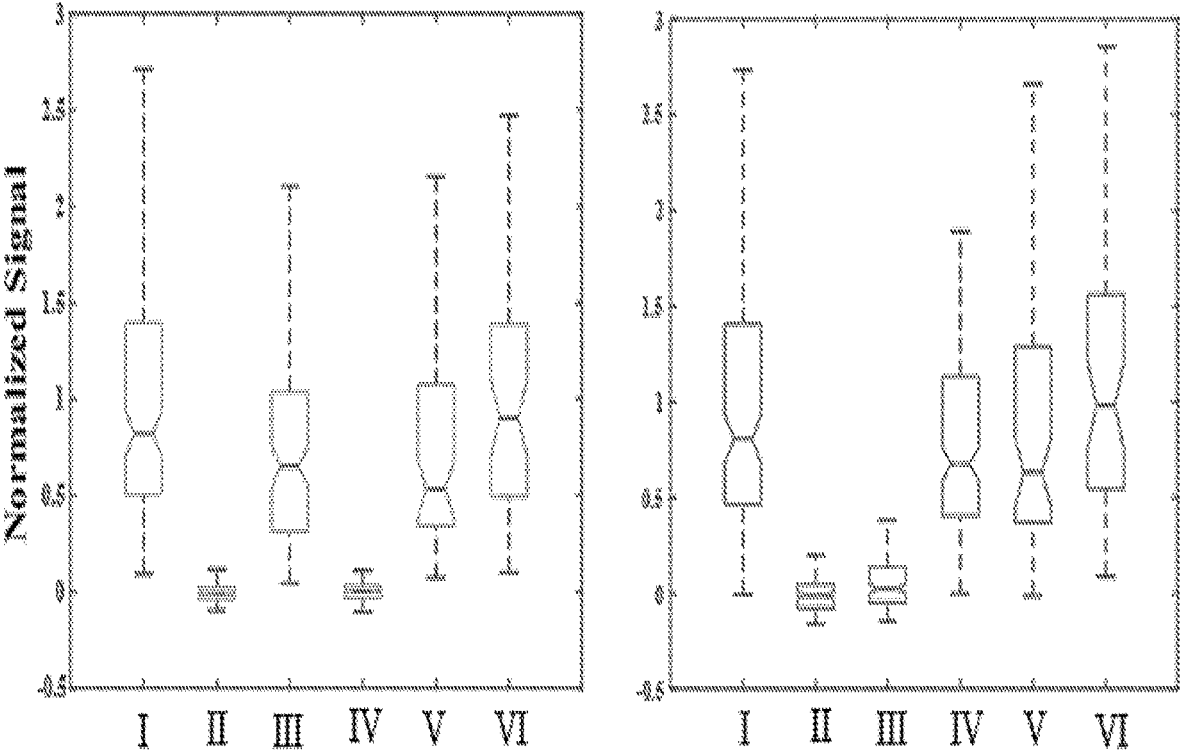

The fluorescence intensity attributed to CSP on the surface of cells was measured using a custom MATLAB code and parameterized in terms of the mean fluorescence intensity around the perimeter of individual cells (Akbari, E. et al, Adv. Mater. 2017: 29). The mean fluorescence intensity for individual cells was normalized with respect to the overall average of the mean fluorescence intensity under conditions I (i.e., cells functionalized with non-QO labeled CSP) and II (i.e., cells functionalized with QO labeled CSP) as the maximum and minimum, respectively. Based on the results in FIG. 2C the mean fluorescence intensity from the CSP increased robustly after the addition of the respective DNA targets A and B compared to condition II (cells functionalized with QO labeled CSP). The overall average of the mean fluorescence intensity of the cells incubated with target A (condition III, Cy3 plot) has a similar average intensity to cells functionalized with non-QO labeled CSP (condition I). Similarly, the average from the cells functionalized with QO labeled CSP and incubated with target B (condition IV, Cy5 plot) is as high as the average in cells functionalized with non-QO labeled CSP (condition I). Importantly, comparing cells with QO labeled CSP after incubation with targets A or B (conditions III and IV) to the minimal signal (i.e., cells functionalized with QO labeled CSP, condition II) shows that the addition of each DNA target only affects the corresponding fluorescent signal and does not affect the fluorescent intensity in the other channel. In addition, exposing cells with QO labeled CSP to both targets (condition V) leads to robust fluorescence increases in both fluorescence channels, illustrating both specific and multiplexed sensing of molecular targets.

Figure 2D:
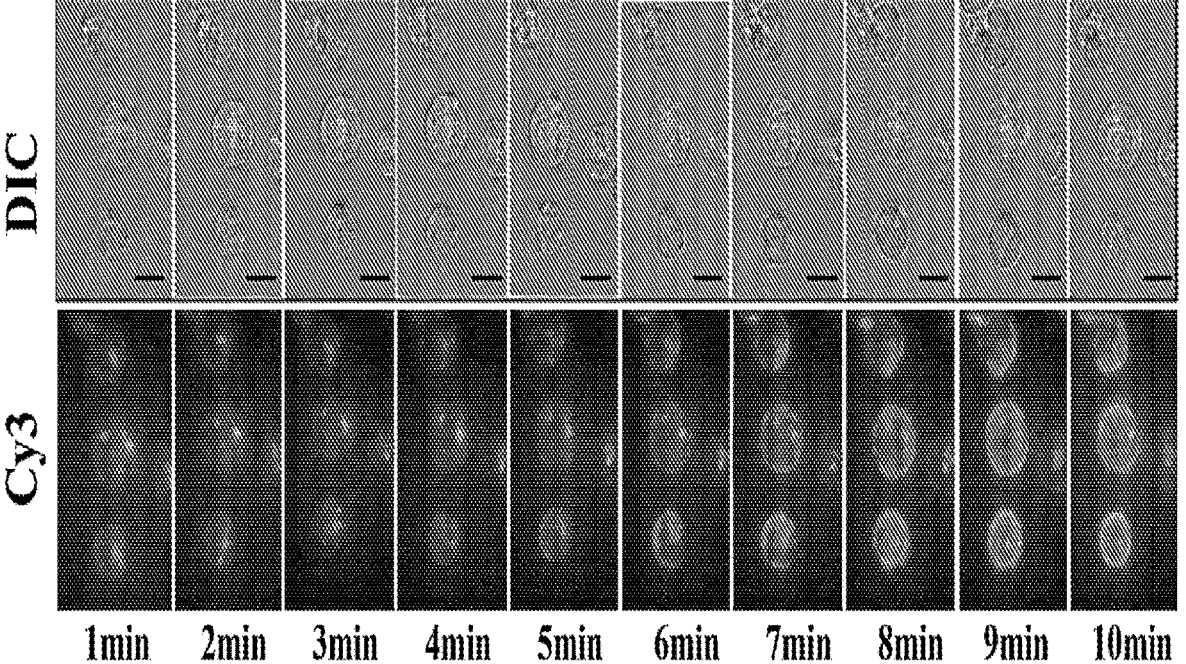
Figure 2E:
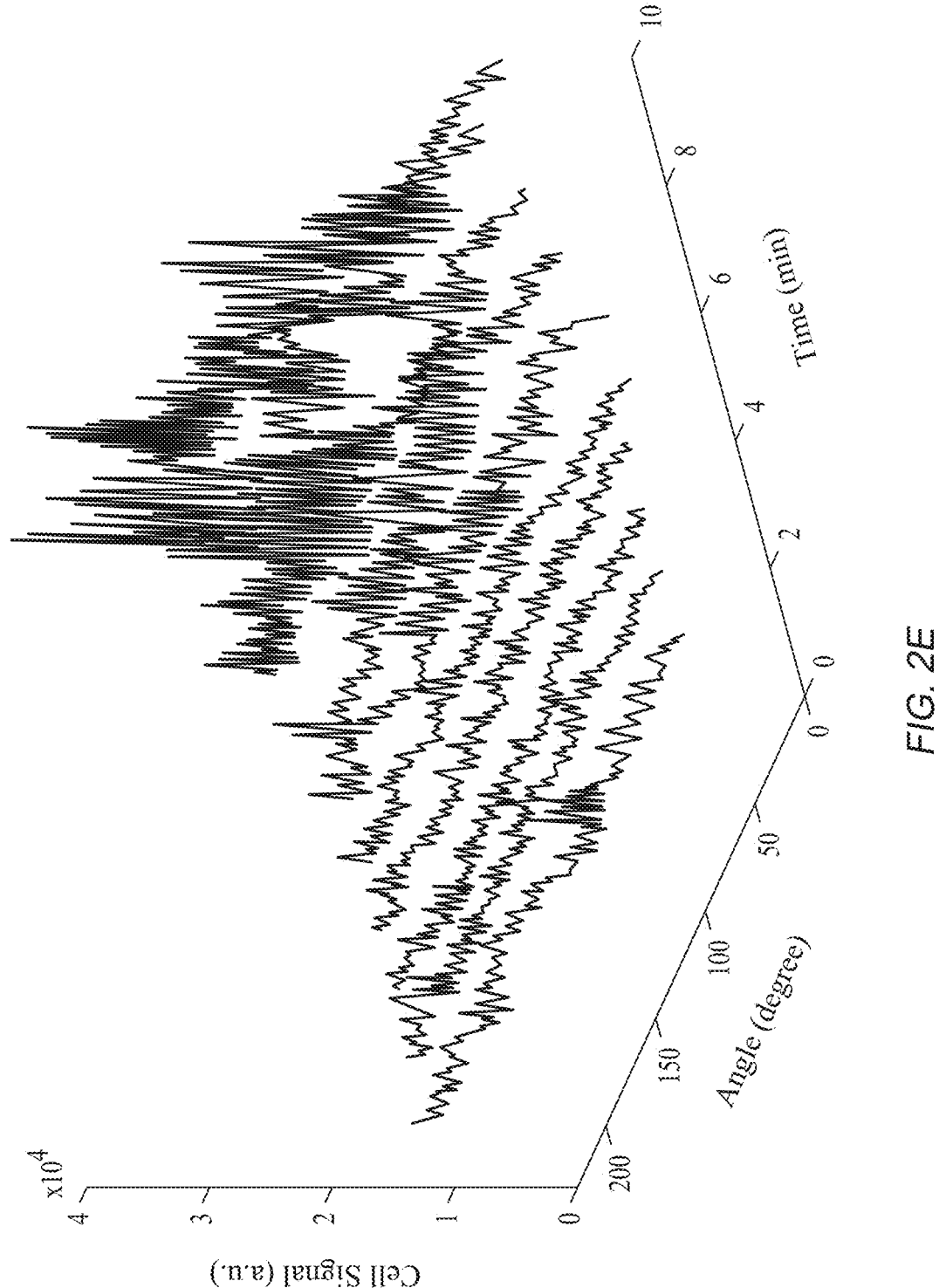

To demonstrate CSP as a tool to monitor cell-biomolecule interactions in real time, the detection of target A on the cell membrane was demonstrated over a time span of 10 min. FIG. 2D shows brightfield and fluorescent images of 3 single cells, which were initially functionalized with QO labeled CSP. At time t=0 min, target A was added to the imaging dish at a final concentration of 1 µM, and images were taken every minute to monitor the temporal increase in CSP fluorescence intensity due to detection of target A. The fluorescent intensity was quantified around the membrane of the middle cell at each time point (FIG. 2E). The result shows up to 4-fold increase of the Cy3 intensity at some angles, which highlights the ability to resolve interactions with sub-cellular resolution around the cell surface. The nonuniform fluorescent intensity increase on the cell periphery could be a result of the inhomogeneous distributions of CSP around the cell membrane. However, the non-QO labeled CSP conditions show a relatively uniform density of structures around the periphery of cells, suggesting the inhomogeneous reporter fluorescence may be due to non-uniform binding of targets.

Figure 12A:
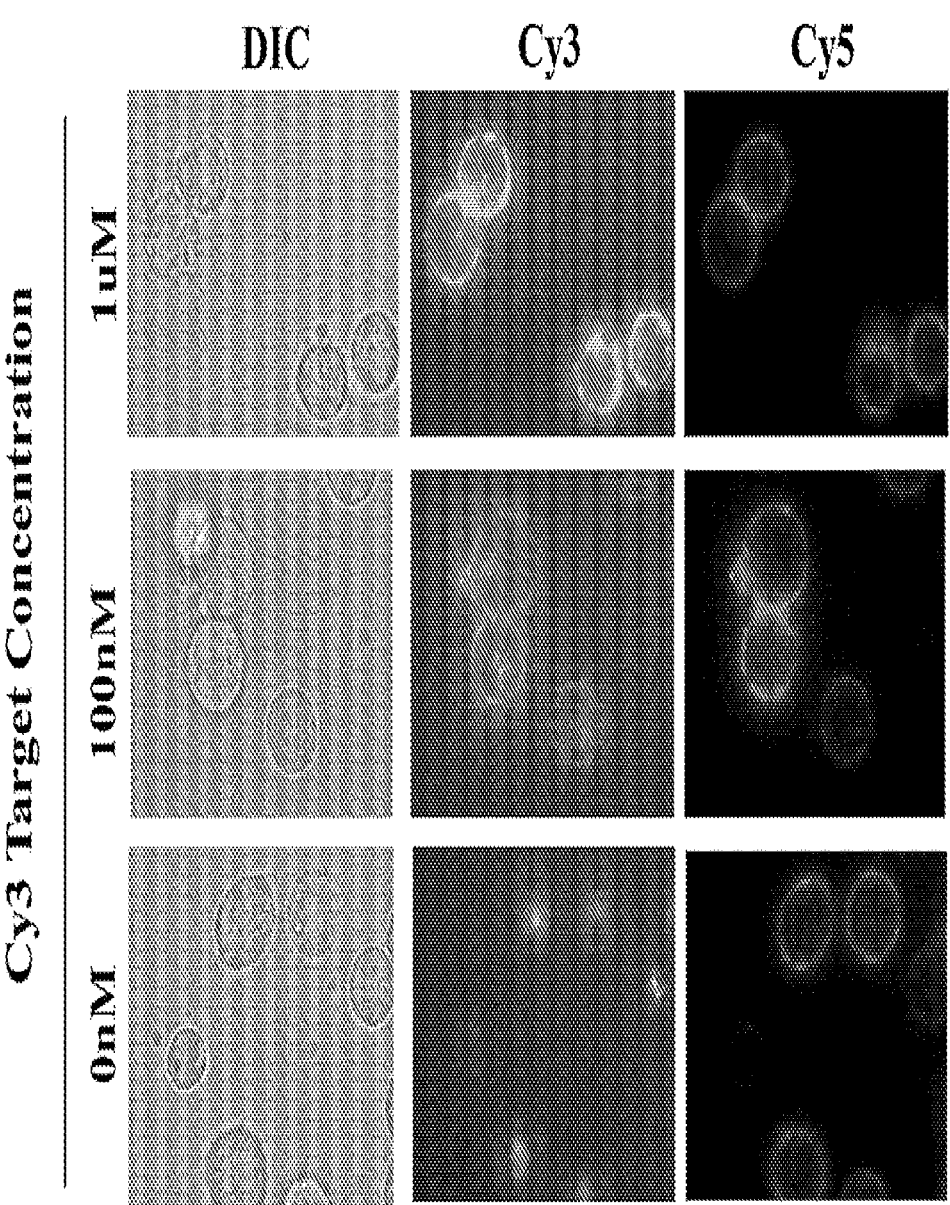
FIGS. 12A and 12B show detection of different concentrations of DNA target in bulk on CH12.LX cells.
Figure 12B:
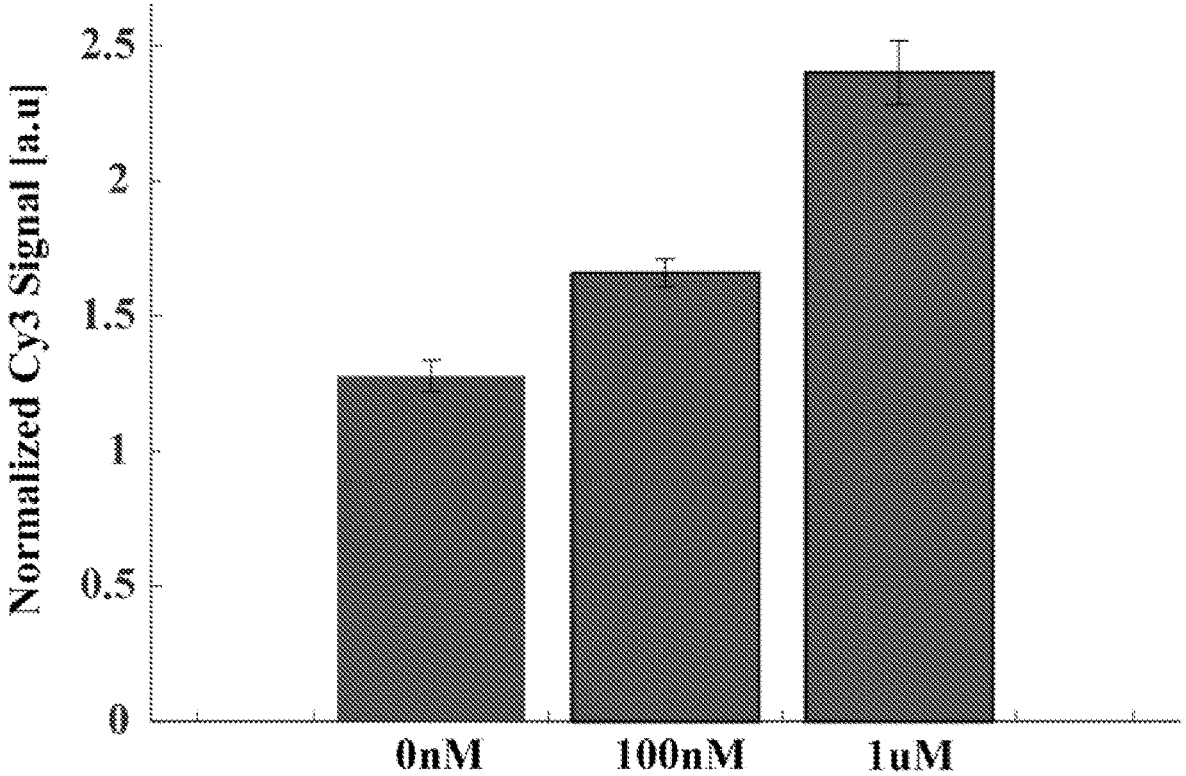

Interestingly, there was a peak in intensity at 7 min. This nonuniform distribution of detection signal may be due to inhomogeneous distribution of targets or binding events at the cell surface due to spatial localization of CSP nanodevices to cholesterol- and sphingolipid-rich regions of the plasma membrane. However, the 10 min time point shows a more even distribution of CSP, suggesting the inhomogeneity at earlier time points is due to the spatiotemporal variation of target binding around the cell possibly due to inhomogeneous distribution of targets in solution. DNA can interact with the membrane itself which might cause some inhomogeneity in the distribution of DNA targets around the cell. These results highlight that it would be beneficial to be able to consistently track the presence of the CSP separately from the detection signal directly on the same cell. To demonstrate this capability, we also folded CSP with the internal Cy5, without the quencher oligo and the overhang, and Cy3 along with its quencher oligo and overhangs. In this modification, Cy5 acts as an internal control signal, and we can use Cy3 channel to detect the corresponding DNA target. A concentration titration experiment was run using this platform, and the results are shown in FIG. 12. The Cy5 signal stayed constant across all samples and the Cy3 channel that responds to the DNA target in a concentration dependent manner, suggesting this normalization approach could be useful for quantifying concentrations of targets.

CSP Detects Cell Membrane Interactions in 3-D ECM Model

Interactions between cells and h their microenvironment are highly affected by ECM biophysical and biochemical properties. Design and fabrication of integrated microfluidic devices with localized 3-D ECM compartments are advancing the study complicated living systems (Avendano, A. et al, Front. Bioeng. Biotechnol. 2019, 7:6; Huang, C. P. et al, Lab Chip 2009, 9:1740), hence, aiding understanding of detailed biological mechanisms. These devices enable controlling biophysical properties of the microenvironment such as collagen density, while enabling measurements with subcellular spatial resolution in real time. Here, a tissue model was used to establish the successful incorporation of functionalized cells into the collagen matrix to investigate the cell-target molecule interaction in a 3D microenvironment that is more representative of native biological conditions.

Figure 3A:
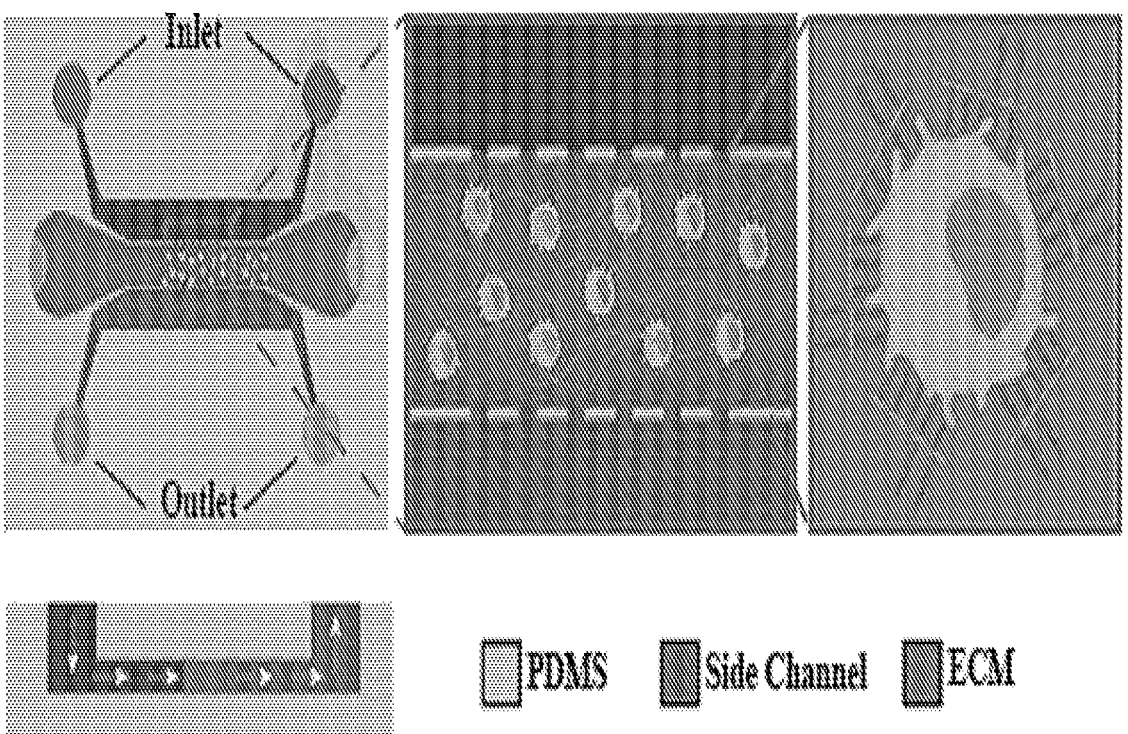
FIGS. 3A to 3D show detection of ssDNA targets on DCs in a 3-D collagen matrix using EPC.

To determine how target biomolecules interact with functionalized cells in the 3-D collagen matrix, a microfluidic platform was developed that features fluid flowing through two adjacent channels (side channels) on either side of a central channel that contains a 3-D collagen extracellular matrix (ECM). This microfluidic system is refer to as an ECM Probing Chip (EPC). The EPC has two side channels (50 µm in height) that are spaced 1 mm apart, each with its own individual inlet and outlet. The individual inlets and outlets in the side channels (FIG. 3A) allow for the control of flow through the side channels and across the middle ECM channel, which contains a collagen matrix that can be seeded with live cells. Along the device, there are six apertures (100 µm in width and 50 µm apart) that allow for components introduced into a side channel (e.g., target strands) to flow through the 3-D collagen matrix (FIG. 3A). In these experiments, dendritic cells were functionalized and mixed with collagen I and were seeded into the middle ECM channel of the EPC and incubated for 30 min at 37° C. to ensure collagen polymerization prior to running detection experiments.

Figure 3B:
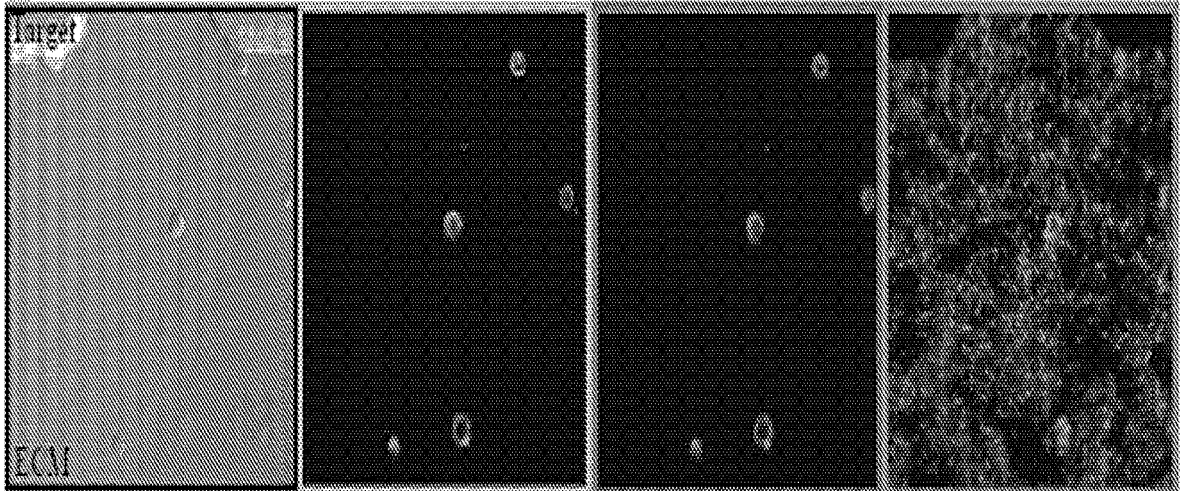

First, fluorescence and confocal microscopy were used to show the successful formation of collagen fibers and the stability of functionalized cells incorporated into collagen matrices. FIG. 3B shows (left to right) brightfield, Cy3, Cy5 and reflectance images of DC cells incorporated into the middle channel, located close to an aperture. Yellow and Red images demonstrate the stability of CSP on the membrane of the DCs at 2 hours after the preparation of the samples and the reflectance image shows the collagen matrix structure.

Figure 3C:
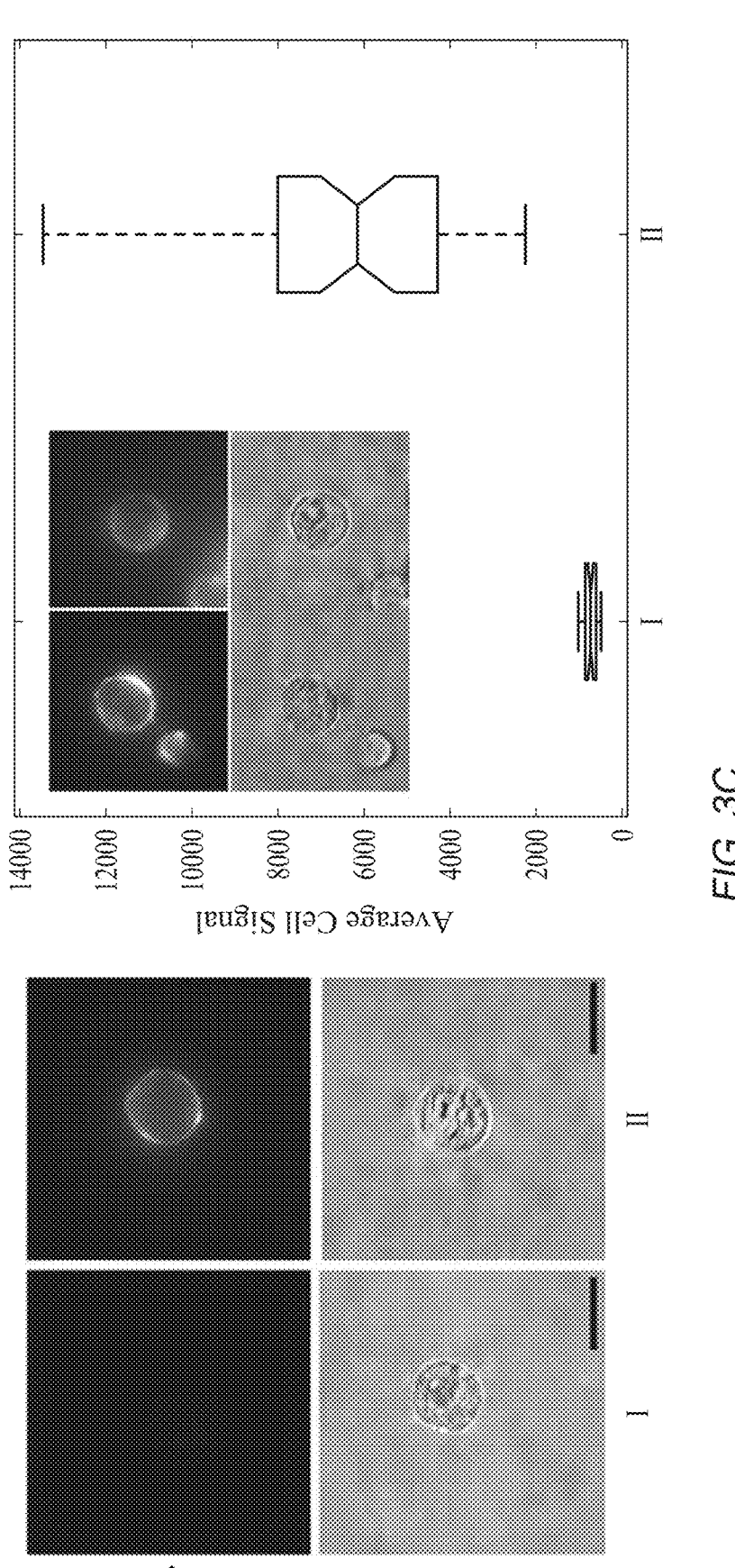

In order to establish the functionality of CSP on the membrane of DC, the two-channel detection experiment was repeated with DCs. Figure S4 shows the successful multiplexed detection of targets A and B on the membrane of DCs deposited in an imaging dish. Next, the detection of target A on the DCs seeded within the ECM was tested in the EPC. DCs functionalized with QO labeled CSP were seeded into the middle channel of the EPC, and DIC and fluorescent images were taken from approximately 40 individual cells (condition I in FIG. 3C). Lastly, 1 µM of target A was introduced into the inlet channel (target channel) and PBS was added to outlet channel. By applying a droplet of DNA target on top of both reservoirs of the inlet channel, a pressure difference was applied across the collagen channel, causing flow of the DNA target through the collagen. Individual cells were again imaged after 15 min (condition II in FIG. 3C) and the mean fluorescence intensity was measured. The box plot in FIG. 3C shows the average of DCs mean fluorescence intensity increased by approximately 6 times after the addition of the target DNA.

Figure 3D:
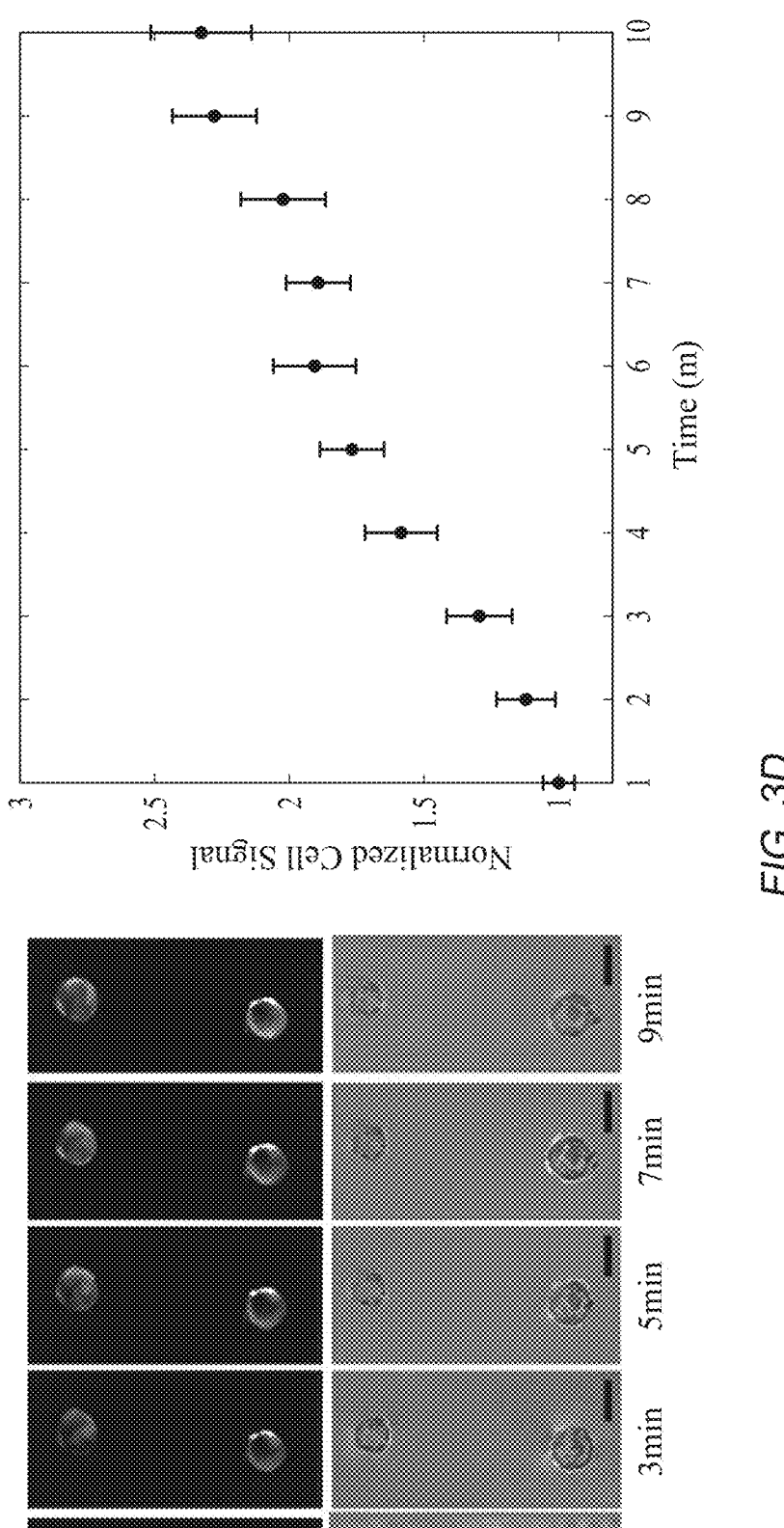
Figure 8:
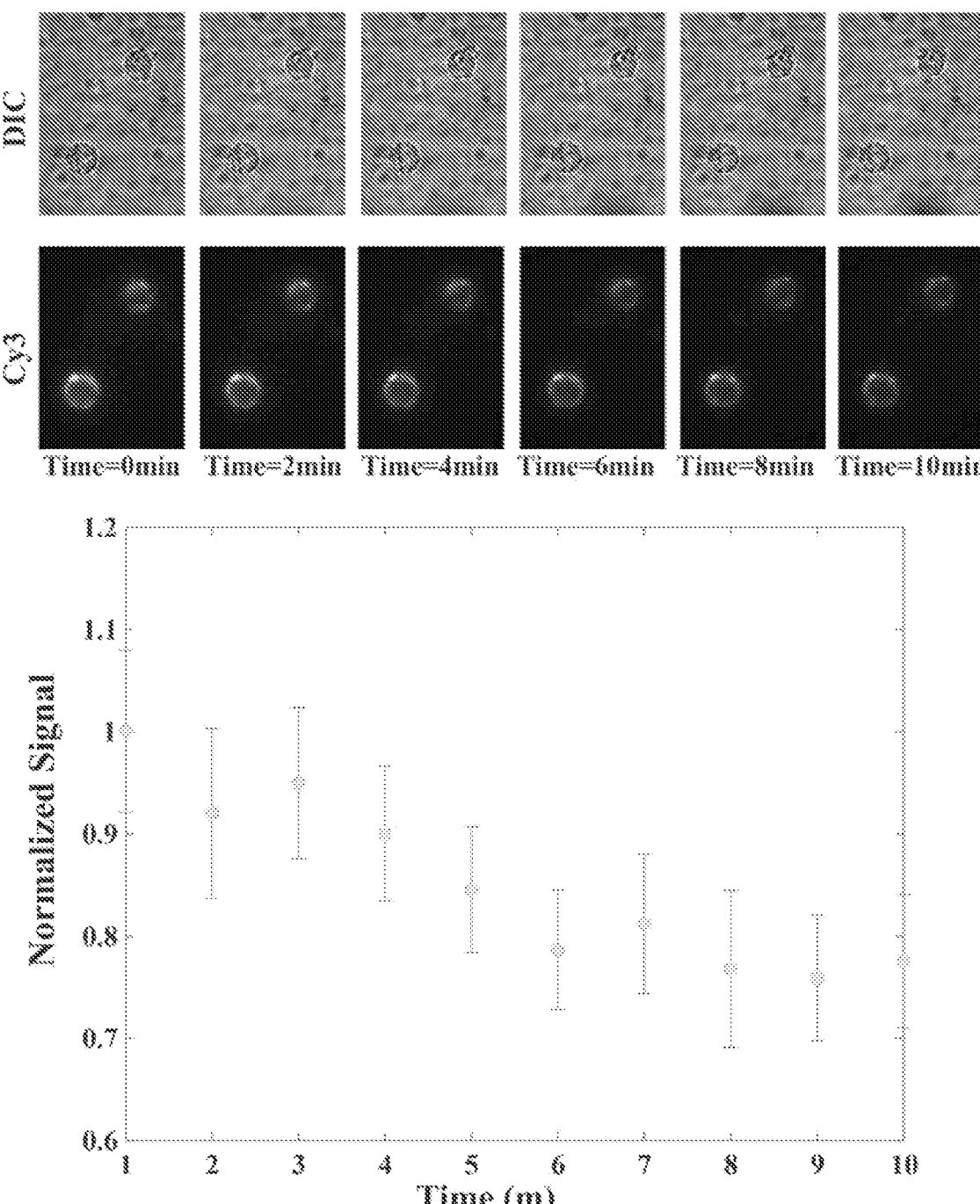
FIG. 8 shows photobleaching of Cy3 channel measured using cells functionalized with non-QO labeled cells. 10 Cells seeded into the collagen matrix were imaged every minute for 10 minutes with the same settings and the cell membrane signal for each cell was measured. The mean fluorescent signal was used to normalize Cy3 cell signals in FIG. 3.
Figure 9:
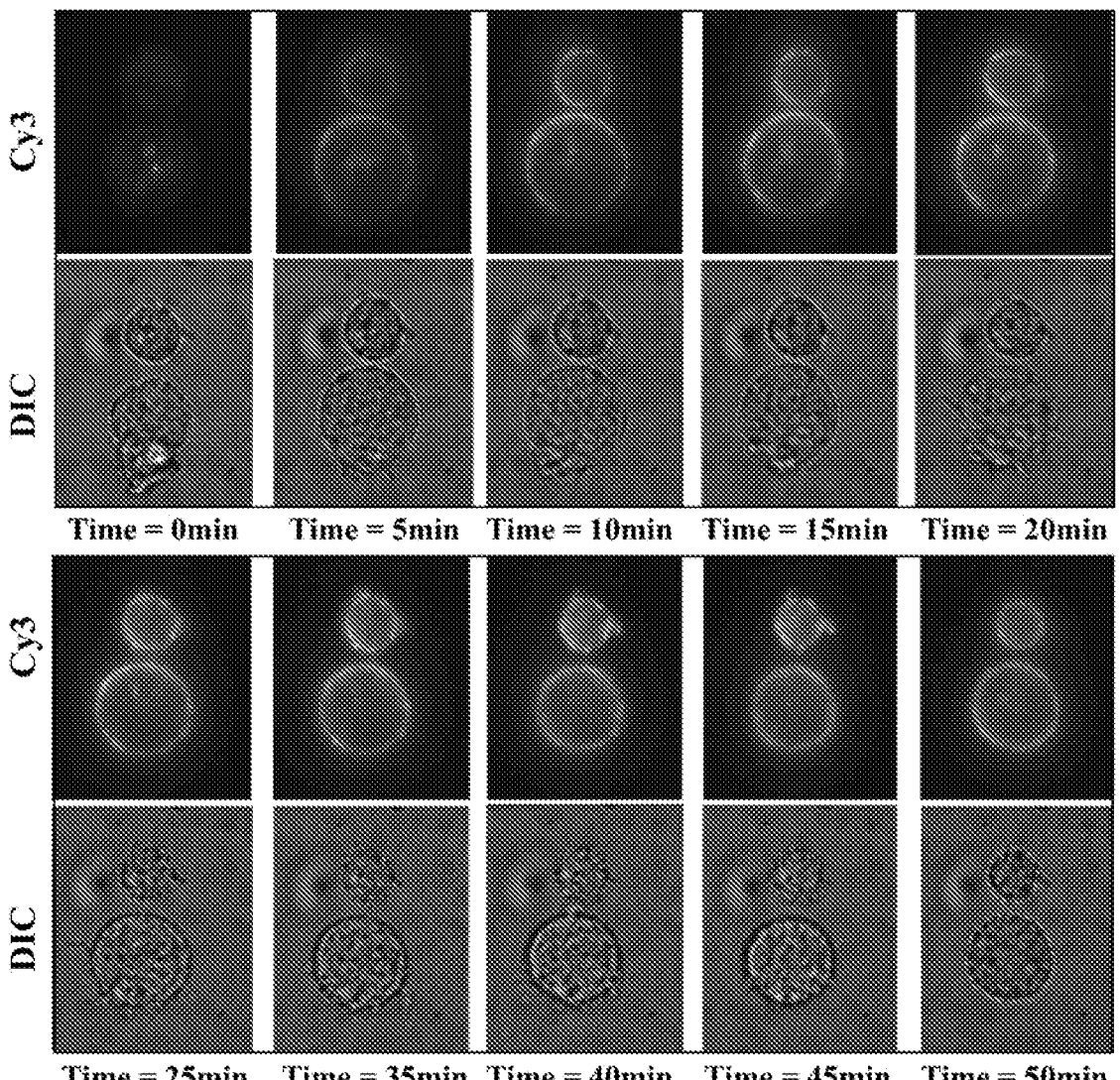
FIG. 9 shows long term detection of ssDNA targets on DCs in a 3-D collagen matrix using EPC. Fluorescent (Cy3) and DIC images representing the detection of target A on the cell membrane of DCs in the collagen matrix over 50 min experiment.

The capability of the platform to study the interaction of biomolecules with the cell membrane in situ in real time was further demonstrated. The EPC was seeded with DCs functionalized with QO labeled CSP and was mounted on the imaging stage. Target DNA and PBS were introduced into the inlet and outlet channels, respectively. Then, two droplets of DNA target were applied on top of the inlet reservoirs to help drive the flow through the middle channel and individual cells were imaged every minute over 10 minutes. FIG. 3D shows DIC and fluorescence images of two CSP functionalized DCs imaged over time. The intensity of the Cy3 signal increased significantly over 10 minutes after introduction of the target DNA. The mean fluorescence intensity of individual cells at each time point was measured and the box plot in FIG. 3D shows its average relative to the average signal at time zero over the timespan of the experiment. To account for photobleaching, the mean fluorescence intensity of each cell was normalized at each timepoint to the average of cell fluorescence intensity for the case where no target was added to cells with non-QO labeled CSP (FIG. 8). The Cy3 signal was also normalized with respect to the average Cy3 signal at time 0. The Cy3 reporter signal increases steadily, more than doubling over 10 minutes. This experiment was repeated, and cells were imaged for 50 minutes, with 5-minute intervals (to prevent significant photobleaching), and results are shown in FIG. 9. These experiments revealed the signal increased mainly over the first 10 min of the experiment and saturated by approximately 20 min. These results demonstrate the ability to study dynamic cell-biomolecule interactions over time, with higher time resolution over short times, or over prolonged periods of time with lower time resolution.

Figure 11A:
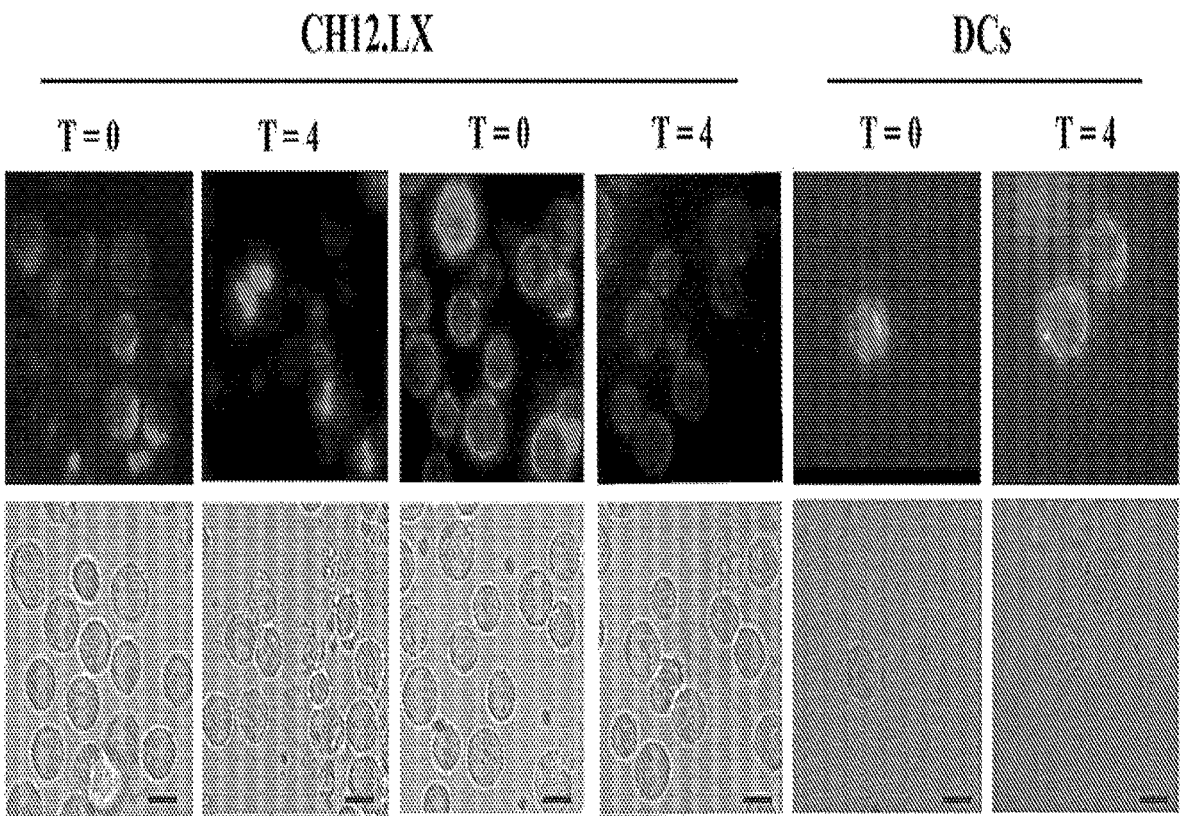
FIGS. 11A and 11B show stability of cell membrane attachment to CSP and cholesterol conjugated oligonucleotide.
Figure 11B:
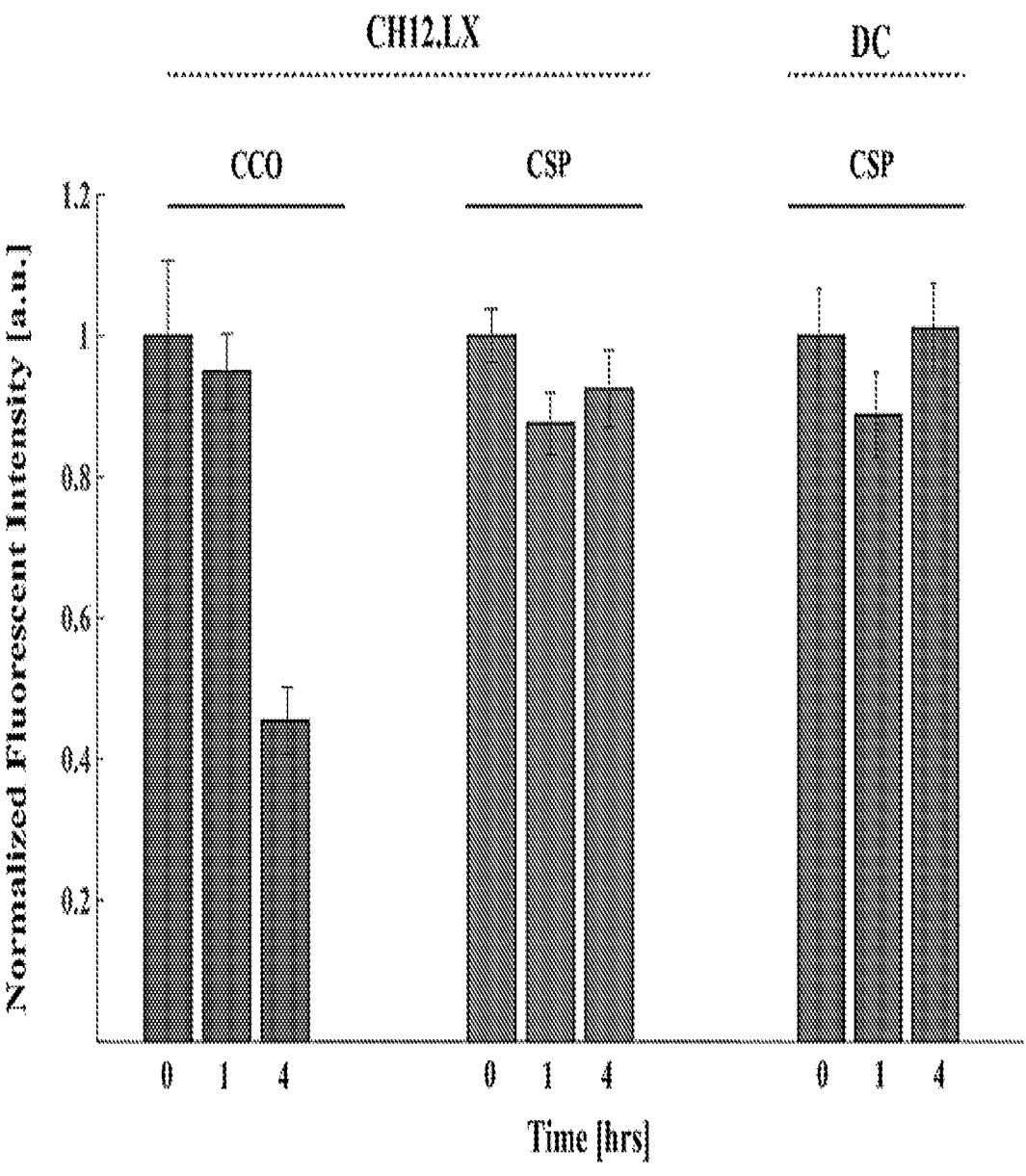

To test whether CSP could be used for longer-term experiments, we tested the stability of membrane anchoring on both DCs in the ECM and CH12.LX cells in suspension (FIG. 11). The level of CSP on the surface of remained similar up to 4 hours for the DCs in ECM and decreased by less than 10% in the CH12.LX cells in suspension. For the CH12.LX cells, we also compared the stability to cholesterol labeled dsDNA strands, where we observed a 55% decrease in presence of DNA strands on the cell surface at 4 hours, and the majority of signal appeared to come from internalized strands that remained near the cell surface (FIG. 11A). Hence, the CSP provides a distinct advantage for cell surface applications at the time scale of several hours. It is worth noting that photobleaching would limit the frequency of imaging especially for longer time points.

Figure 13A:
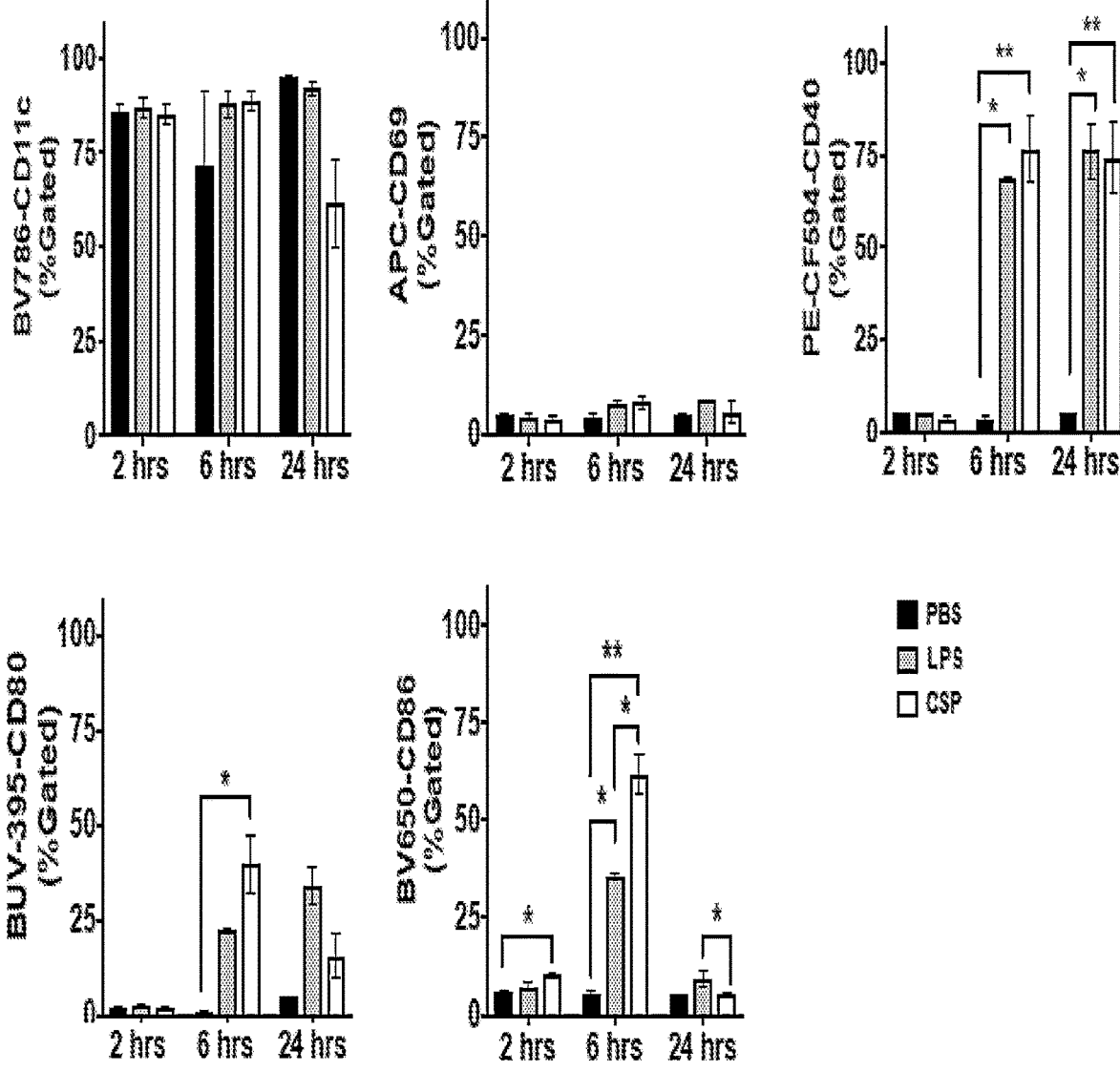
FIGS. 13A and 13B show LPS treated DCs showed comparable levels relative to PBS treated cells of CD11c both percentage of CD11c$^+$ cells and MFI, representative of cell surface density. While the percentage of CD11c$^+$ DCs remained unchanged at 2 and 6 hours post CSP addition, the percentage of CD11c$^+$ cells decreased by 24 hours relative to PBS treated cells, although the decrease was not statistically significant (FIG. 13A, top). In addition, CD11c MFI showed non-significant decreased levels relative to PBS treated cells at 2, 6, and 24 hours after CSP addition (FIG. 13B, top). LPS treated DCs showed increases percentages of CD69+, CD40+, CD80+, and CD86+ relative to PBS treated cells, with statistically significant elevations observed with CD40+ cells at 6 and 24 hours and CD86+ cells at 6 hours post addition (FIG. 13A, second through fourth row). In addition, LPS treated DCs exhibited increased MFI levels of CD69, CD40, CD80, and CD86 relative to PBS treated cells, with an observed significant CD80 elevation 6 hours post addition and CD86 elevation relative to CSP at 24 hours (FIG. 13B, second through fourth row). In a similar manner, CSP induced increases in the percentages of CD69+, CD40+, CD80+, and CD86+ DCs relative to PBS treated cells, with significant elevations exhibited as follows: CD40+ cells at 6 and 24 hours, CD80+ cells at 6 hours, and CD86+ cells at 2 and 6 hours post addition (FIG. 13A, second through fourth row). CSP treated DCs also increased surface MFI levels of CD69, CD40, CD80, and CD86 relative to PBS treated cells, with significant observed elevations of CD80 at 6 hours and CD86 at 2 and 6 hours (FIG. 13B, second through fourth row). Collectively, these findings suggest that CSP induces an immune response either alone, as predicted due to previous studies, or due to the presence of sample endotoxin. Evaluation of endotoxin levels in CSP structures by LAL endotoxin detection assay revealed endotoxin levels at 3.50 EU/ml, suggesting endotoxin removal is an important consideration for future studies. Data are expressed as either mean % Gated (FIG. 13A) or mean MFI (FIG. 13B)±SEM and represent 2 independent experiments. Stats, one-way ANOVA followed by Tukey's multiples comparisons test. *, $p \leq 0.05$; **, $p \leq 0.01$.
Figure 13B:
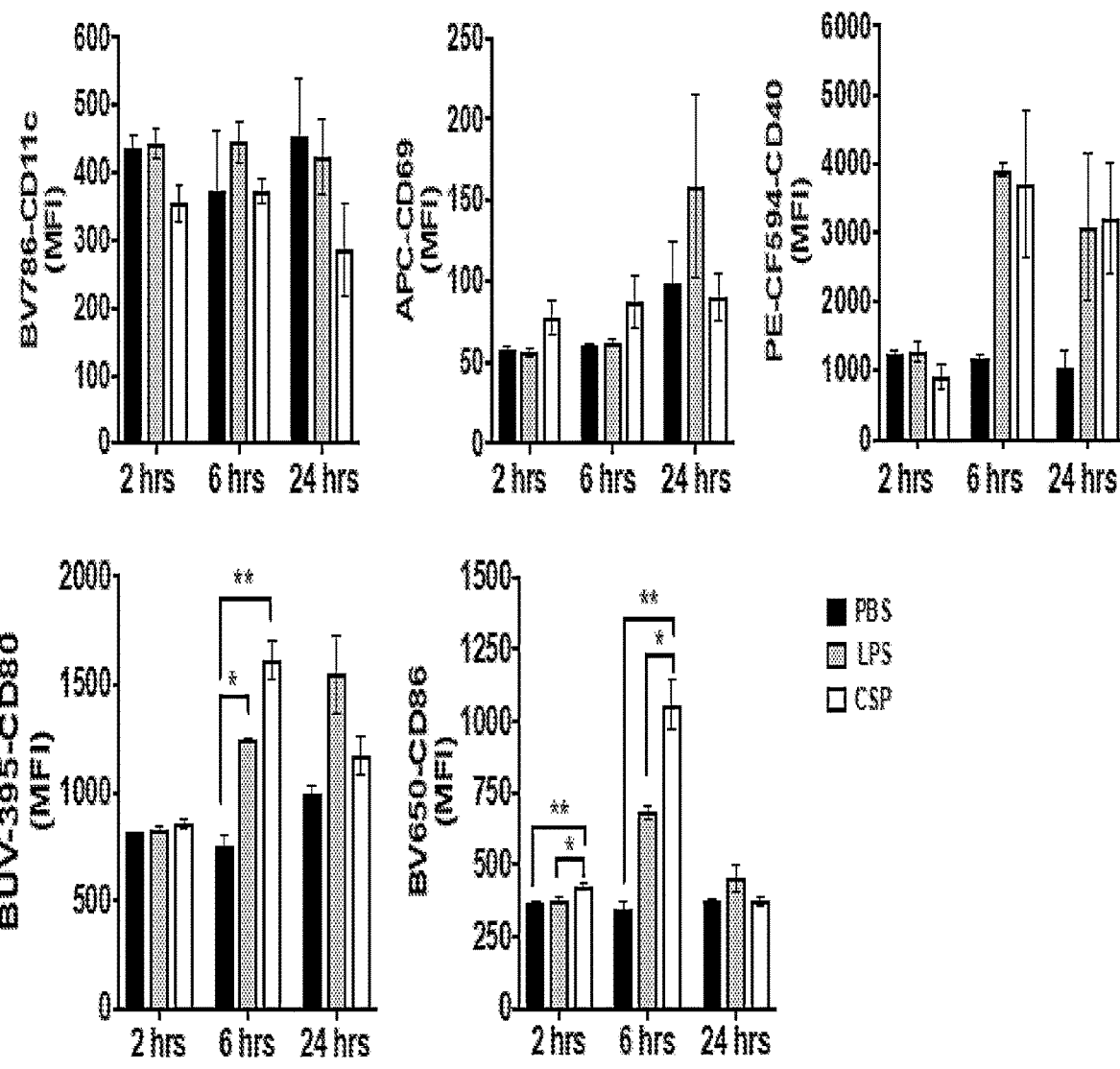

To assess potential effects of the CSP on cell function, especially at these longer timepoints, a live/dead assay was performed on DCs seeded into the collagen model. These results showed that DCs viability was consistently high (~90%) after 4 hours of incubation in the EPC device and drops to 70% (FIG. 10) over 24 hr for both CSP labeled and unlabeled DCs. These results indicate functionalizing cells with CSP does not have an impact on their viability up to 24 hr. Other potential effects of the CSP on cell function could include occluding binding of surface receptors or cell stimulation, especially for immune cells. To assess these potential affects, we evaluated surface markers of DCs labeled with CSP via flow cytometry. These results revealed no difference in binding of an antibody to the DC marker CD11c in cells labeled with CSP versus unlabeled cells up to 6 hours (FIG. 13), suggesting this level of CSP labeling does not impede accessibility to the CD11c surface receptors (although a decrease in antibody binding to CD11c was observed at 24 hr). The level of CD69, CD40, CD80, and CD86 (all surface markers of immune cell activation) was also quantified on DCs labeled with CSP and compared to cells treated with PBS or LPS as negative and positive controls, respectively (FIG. 13). In summary, these results revealed little to no increase in these activation markers up to 2 hr, and significant increases at 6 hr and longer time points. The cellular activation caused by CSP was comparable to LPS, which could be due to residual endotoxin remaining from the bacterial scaffold production. Collectively, these results suggest that CSP does not significantly impact cell viability, surface receptor binding, and expression of surface activation markers over the timescale of 2 hours. However, cellular activation is important to consider for future studies relating molecular detection to cellular function. Moreover, more careful production (e.g. endotoxin removal) or modification methods (e.g. polymer coating) could provide routes to mitigate cellular activation caused by CSP.

Conclusion

A method was established to study cell membrane interactions with multiple biomolecules in the local ECM microenvironment by engineering cell membranes with DNA origami sensor elements. The capability to spatiotemporally monitor those interactions in situ was developed using the microfluidic 3-D tissue model device. The capability of the DNA nanodevices to detect multiple DNA targets was established and the multiplexed sensing on the surface of CH12-LX B cells was demonstrated. MutuDC1949 cells were functionalized and seeded into a collagen ECM. The capability of this method to monitor subcellular interaction in the matrix using microfluidic 3-D tissue model device was demonstrated. These results established the integration of DNA origami nanodevices, cell membrane engineering, and microfluidic tissue model systems as a unique approach to probe biological interactions in physiologically relevant 3-D environments with high spatial and temporal resolution.

Here, there was a focus on nucleic acid targets as a proof-of-concept to enable the detection of relevant targets such as miRNA and ctDNA that are present in extracellular circulation and ECM and can play an important role in activation of immune cells (Raisch, J. et al, World J. Gastroenterol. 2013, 19:2985). This approach could be further expanded to study cell response to a variety of cell stimulating molecules such as cytokines and growth factors. For example, the incorporation of aptamers could enable the detection of targets like proteins, growth factors and the measurement of local environmental factors such as pH (Modi, S. et al, Nat. Nanotechnol. 2009, 4:325). Other DNA constructs have been demonstrated as tools to measure forces (Hudoba, M. W. et al, ACS Nano 2017, 11:6566; Le, J. V. et al, ACS Nano 2016, 10:7073; Glazier, R. et al, Nat. Commun. 2019 101 2019, 10:1; Iwaki, M. et al, Nat. Commun. 2016 71 2016, 7:1) or ion concentrations. The programmability and stability of the platform in a wide range of buffers (with different ion composition) allows for the incorporation and functionality of many DNA aptamers such as PDGF (Zhao, W. et al, Nat. Nanotechnol. 2011, 6:524) aptamer on the origami device. Thus, it is possible to look at the underlying mechanisms of cooperative action between multiple types of biomolecules or biomolecules and other local factors (pH, forces, ions).

In this study, organic fluorophores were used to label the DNA nanostructures. Common fluorescence imaging systems could multiplex 3-4 channels. Further multiplexing could be achieved using novel fluorescent imaging techniques such as metafluorophores (Woehrstein, J. B. et al, Sci. Adv. 2017, 3), frequency multiplexed DNA-PAINT (Gomez-Garcia, P. A. et al, Proc. Natl. Acad. Sci. 2018, 115:12991), or fluorescent nanoparticles with controllable spectral properties. These advanced imaging approaches could advance the distinct number of channels, and minimize color cross-talk and photobleaching. Imaging the samples over longer timespan and investigating long-term cellular interactions, requires advanced imaging techniques and sample preparation method to prevent photobleaching and provide reliable signal. Luminescent quantum dots (QDs) and other fluorescence nanoparticles have been proven as a promising alternative to traditional organic dyes in various fluorescence-based applications such as multi-color live cell imaging over a week (Jaiswal, J. K. et al, Nat. Biotechnol. 2003, 21:47). The analysis of QDs as donor and acceptor for Förster Resonance Energy Transfer (FRET) in studying biomolecular interactions has also been established (Cardoso Dos Santos, M. et al, Trends Anal. Chem. 2020, 125:115819). Hence, they are reliable alternatives for small fluorescent molecules when multiplexing multiple detection probes into the DNA nanodevice.

A reliable method to study subcellular interactions in a 3-D tissue model was successfully established using a microfluidic device. Microfluidic devices are revolutionizing how to approach biological questions. The dimensions of microfluidic channels are in the range of physical scale of biological cells, and the control over biophysical and biochemical parameters of the cell microenvironment is unique (Young, E. W. K. et al, Chem. Soc. Rev. 2010, 39:1036). Microfluidic devices are becoming increasingly high-throughput and integrated, leading to organ-on-chips, which could provide insights into how normal human organ functions and disease progress. They have also attracted more attention recently due to their potential to be informative at multiple stages of the drug discovery and development process (Low, L. A. et al, Nat. Rev. Drug Discov. 2021, 20:345). Moreover, cutting-edge microfluidic models allow for recapitulating native cell-ECM structures in microfluidic such as angiogenesis and vessel branches. Although prior work has utilized microfluidic devices to actuate DNA origami nanodevices inside cell-sized microfluidic compartments (Göpfrich, K. et al, Nano Lett. 2020, 20:1571), no prior study has used DNA nanostructures to study subcellular biological phenomena in ECM model using microfluidic devices. Combining the programmability of DNA origami with versatile designs of microfluidic chips allows for the investigation of the subcellular interactions under controlled biomolecular transport and fluid mechanical stimuli with unprecedented spatial and temporal resolution.

Experimental Section

Design and Fabrication of the CSP

The CSP was designed using the software caDNAno[40] and fabricated using protocols developed by Castro et al (Castro, C. E. et al, Nat. Methods 2011, 8:221). CSP is a 65 nm×40 nm×6 nm platform, with 42 potential overhangs (FIG. 1). Staple sequences were specified in caDNAno and ordered from a commercial vendor (Integrated DNA Technologies, Coralville, IA). The CSP was folded using p7249 from the M13mp18 genome with a total of 186 ssDNA staples. To fold the CSP with 2 DNA detection modules on locations C3 and C4, staple strands with an end directly adjacent to the overhang locations (Green oligos in FIG. 4) oligos on these two locations were replaced with one DNA oligo labeled with Cy5 and one DNA oligo labeled with Cy3 fluorophore (Table 2). Moreover, CSP was folded with 30 overhangs on the cell facing side (Bottom overhangs, purple oligos in FIG. 4) and 2 overhangs on the opposite side (Top overhangs, Table 2) on locations C3 and C4. Briefly, purified scaffold at 20 nM concentration was combined with 5-fold molar excess of staples (each staple at 100 nM), and molar excess of QO (if needed, in 200 nM each) in folding buffer (1×FOB: 5 mM Tris, 5 mM NaCl, 1 mM EDTA, supplemented with 18 mM MgCl$_2$).

Figure 4:
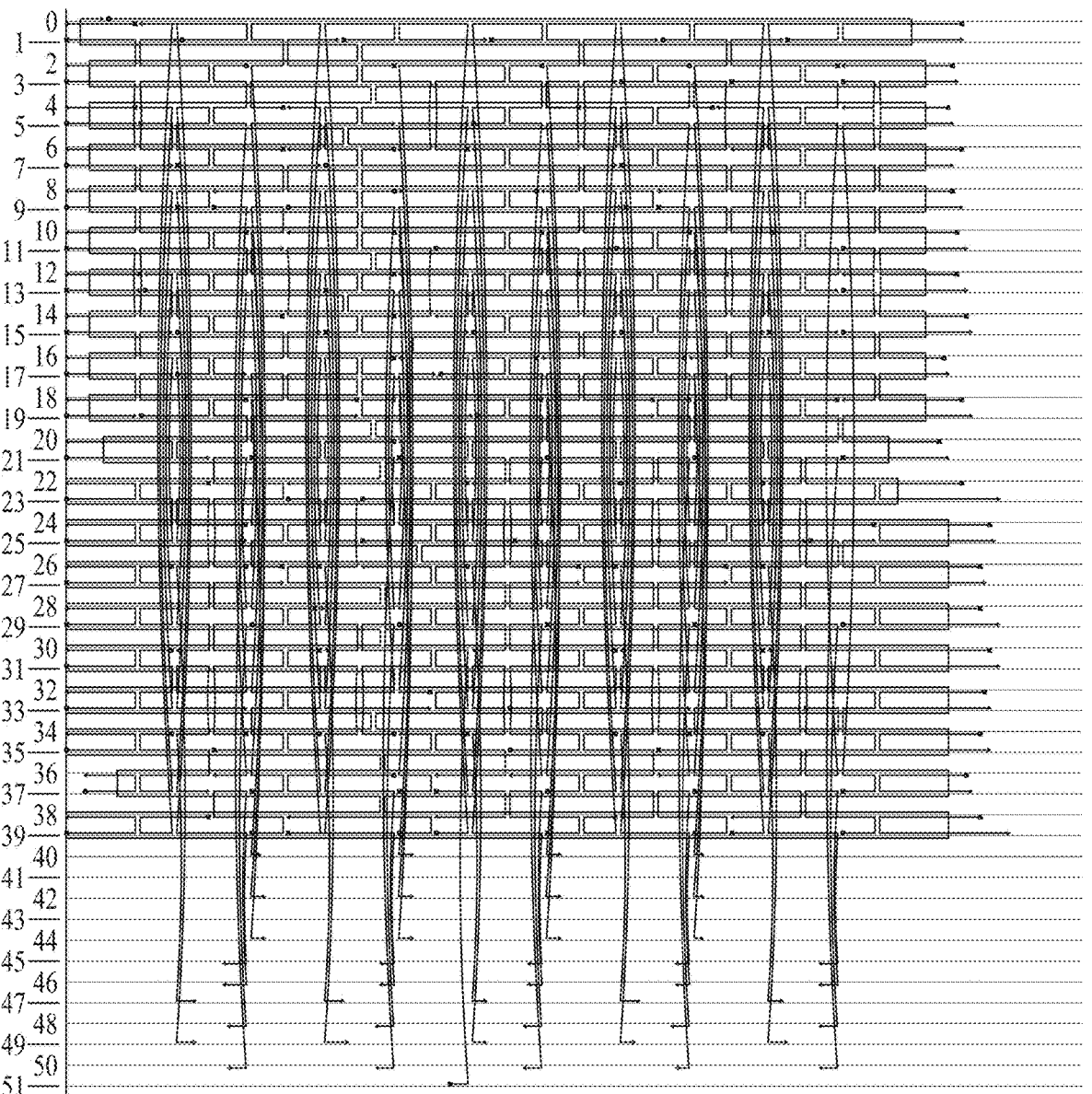
FIG. 4 shows caDNAno design of an example Cell Sensing Platform.
Figure 5:
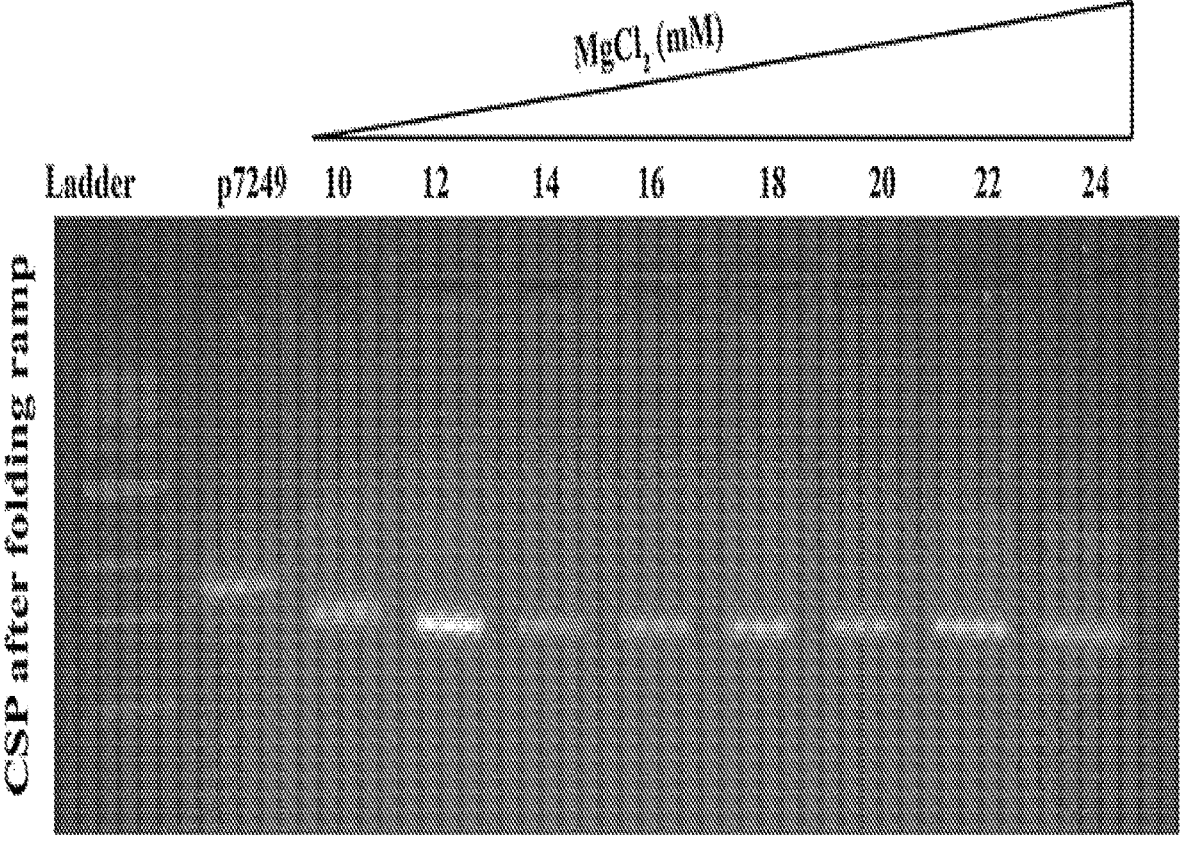
FIG. 5 shows confirmation of folding of the structure using 2.5 fold protocol in different $Mg^2+$ concentrations (left to right, 1 kb DNA ladder (L), the 7249 M13mp18 scaffold starting material, and CSP folded in 10, 12, 14, 16, 18, 20, 22 and 24 mM $Mg^2+$).

In order to find the optimal salt concentration needed for structural folding, initially folding reactions with different salt concentrations (10, 12, 14, 16, 18, 20, 22, 24 mM MgCl$_2$) were prepared. Then the self-assembly reaction was done by rapidly heating the reactions to 65° C. followed by slow cooling to 4° C. over 2.5 days in a thermal cycler (Bio Rad, Hercules, CA). The folding reaction was brought to 65° C. and stepped from 65° C. to 24° C. in 1° C. steps at varying time increments. From 65° C. to 62° C., the temperature was held for 1 hour; from 61° C. to 59° C., the temperature was held for 2 hours; from 58° C. to 46° C., the temperature was held for 3 hours; from 45° C. to 40° C., the temperature was held for 1 hour; from 39° C. to 24° C., the temperature was held for thirty minutes. After being held at 24° C. for 1 hour, the temperature was lowered to 4° C. Folding reaction products were subjected to agarose gel electrophoresis (Castro, C. E. et al, Nat. Methods 2011, 8:221) in a 2% agarose (Life Technologies) gel (0.5× TBE) in the presence of 11 mM MgCl$_2$ and 1 μM ethidium bromide (EtBr) and based on the results, 18Mm $MgCl_2$ was chosen as the optimized concentration for folding the CSP (FIG. 4).

Next, using folding reactions at 18Mm $MgCl_2$, the optimal isothermal annealing temperature was found. The folding mixtures were subjected to thermal annealing by rapid heating to 65° C. followed by isothermal annealing for 4 hours in different temperatures (60, 58.4, 56.0, 52.5, 47.8, 44.4, 41.7, 40) a rapid cooling to 4° C. Folding reaction products were subjected to agarose gel electrophoresis and the results revealed the successful folding of CSP over a wide range of 42 to 59° C. (FIG. 4). 52° C. was chosen for subsequent folding with isothermal annealing. Therefore, to fold CSP, the folding mixtures at 18 mM $MgCl_2$ were subjected to thermal annealing by rapid heating to 65° C. followed by 4 hours in 52 degrees and a rapid cooling to 4° C.

DNA Nanostructure Purification

Folded DNA nanostructures were purified by mixing folding reaction products with equivolume of 15% PEG 8000 (Sigma-Aldrich, St Louis, MO) supplemented with 500 mM NaCl and centrifugation for 30 minutes at 16000 rcg to remove excess staple strands (protocol modified from Stahl, E. et al, Angew. Chemie 2014, 126:12949). After removing the supernatant, purified structures were resuspended in 1×FOB supplemented with 10 mM $MgCl_2$ (storage buffer). To fully remove the to remove excess staple strands, the PEG purification procedure was repeated two times.

Transmission Electron Microscopy (TEM)

TEM grids were prepared as described in Castro et al. (Castro, C. E. et al, Nat. Methods 2011, 8:221). Briefly, 4 μL of approximately 1 nM purified DNA nanostructure was deposited onto a copper TEM grid coated with carbon and formvar (Electron Microscopy Sciences, Hartfield, PA) and incubated for 4 minutes at room temperature. The sample was removed by gently touching filter paper to the edge of the grid and 10 μL of 2% uranyl formate negative stain was applied to the grid and immediately removed with filter paper as a washing step. Then, 20 μL of 2% uranyl formate was immediately added, incubated for 40 seconds, and finally removed with filter paper. The grid was allowed to dry for at least 30 minutes before being visualized on a Tecnai G2 BioTWIN transmission electron microscope (FEI, Hillsboro, OR) in the Ohio State University Campus Microscopy & Imaging Facility (CMIF).

Functionality of CSP in Detection of DNA Targets

To evaluate CSP strand displacement, structures (folded with QO) at 5 nM concentration were incubated with 1 μM final concentration of each DNA target (A or B) at 37° C. for 15 min followed by a fluorescent measurement on fluorometer (FluoroMax-4, Horiba, Japan). The samples were excited with 510 nm and 610 nm lasers for target A and target B respectively and the emission was measured from 530 nm to 700 nm for target A, and 630 nm to 700 nm for target B. The fluorescent intensity of CSP folded with or without QO in the same concentration (5 nM) was also tested on the fluorometer to demonstrate the maximum and minimum fluorescent signal.

Stability of the CSP in Cell Culture Condition

To confirm CSP structural integrity under cell culture conditions, folded structures were purified using PEG centrifugal purification process and resuspended in different cell culture media and were incubated for 4 hours at 37° C. Purified structures were incubated in CH12-LX clear cell culture media (RPMI 1640 without L-glutamine (Corning)) supplemented with 1 mM $MgCl_2$, RPMI supplemented with 2% heat-inactivated Fetal Bovine Serum (FBS) (Atlas Biologicals) and 1 mM $MgCl_2$, RPMI supplemented with 8% FBS and 1 mM $MgCl_2$, 1× Phosphate Buffered Saline (PBS) without $MgCl_2/CaCl_2$ (Corning, Cat #21-031-CV), 1×PBS supplemented with 2% FBS and 1 mM $MgCl_2$, and 1×PBS supplemented with 8% FBS and 1 mM $MgCl_2$ following PEG purification. Agarose gel electrophoresis assay in a 2% agarose gel in the presence of 11 mM $MgCl_2$ and 1 μM ethidium bromide followed by visualization of the excised gel bands on TEM was used to confirm the stability of the structures in the cell culture media (FIGS. 1 and 7).

Cell Culture

CH12-LX is a murine B-cell lymphoma obtained (Haughton, G. et al, Immunol. Rev. 1986, 93:35). In order to culture the CH12-LX B cells, the RPMI 1640 without L-glutamine (Corning) was supplemented with 10% heat-inactivated FBS (Atlas Biologicals), 1% Penicillin-Streptomycin-Glutamine (100×) (Thermo-Fisher), 1% Sodium Pyruvate (100 mM) (Life Technologies), 1% HEPES (1M) (Life-Technologies), 1% MEM Non-Essential Amino Acids (100×) (Life Technologies). For experiments, CH12-LX cells were washed once with 1× PBS, followed by one wash with the experimental medium (clear RPMI 1640 without L-glutamine (Corning) supplemented with 2% heat-inactivated FBS, and 1 mM $MgCl_2$). Finally, CH12-LX cells were resuspended in the experimental medium at 4000 cells/uL for incubation with cholesterol-conjugated oligos.

The wild-type MutuDC1940 dendritic cell (DC) line is derived from mouse spleen tissues and is GFP positive due to the GFP reporter in the CD11c:SV40LgT transgene. This cell line was obtained from abm (Richmond BC, Canada) and were maintained in supplemented IMDM in 37° C. incubator at 5% $CO_2$. To make the complete growth medium, IMDM (1×)+ Glutamax™ (Gibco Ref: 31980-030) was supplemented with 10% heat-inactivated Fetal Bovine Serum (FBS) (Atlas Biologicals), 1% of 7.5% Sodium Bicarbonate Solution (Life Technologies), 50 μM β-mercaptoethanol, 1% HEPES (1M) (Life-Technologies), and 1% Penicillin-Streptomycin-Glutamine (100×) (Thermo-Fisher). For passaging purposes, the cells were washed with 1× PBS without $MgCl_2/CaCl_2$, followed by their detachment from the culture flask using 1:1 ratio of 1× PBS and 0.25% Trypsin-EDTA (1×) (Corning). The cells were incubated with PBS-Trypsin mixture for 3-4 minutes at room temperature. The Trypsin was then neutralized using the culture media. For functionalization experiments, cells were washed once with 1× PBS followed by one wash with the experimental medium (clear RPMI 1640 without L-glutamine (Corning) supplemented with 2% heat-inactivated Fetal Bovine Serum (FBS) (Atlas Biologicals), and 1 mM $MgCl_2$). Finally, DCs were resuspended in the experimental medium at 4000 cells/μL for incubation with cholesterol-conjugated oligos.

Cell Membrane Functionalization

Cells were functionalized with CSP using the protocol explained in Akbari et. al (Akbari, E. et al, Adv. Mater. 2017: 29). Briefly, cells resuspended in the experimental medium (clear RPMI 1640 without L-glutamine (Corning) supplemented with 2% heat-inactivated Fetal Bovine Serum (FBS) (Atlas Biologicals), and 1 mM $MgCl_2$) were incubated with 10 μM cholesterol-conjugated oligonucleotide for 5 minutes at 37° C. The cells were then washed once in the experimental media to remove the excess cholesterol-conjugated oligonucleotide. Cell were then incubated with the 60-base bridge oligo at 1 μM for 5 minutes at 37° C., followed by the addition of the 20-base pair fortifier oligos at 1 μM, incubation for 5 minutes at 37° C. and a wash with experimental media. Finally, the cells were incubated with the nanostructures at 5 nM, for 5 minutes at 37° C. Cells were washed a final time to remove excess nanostructures using the experimental media and were resuspended in either 1× PBS or the experimental media for the experiment.

DNA Target Detection on the Membrane of Suspension Cells

CSP folded with QO and without QO were incorporated into the membrane of two separate subpopulations of cells (CH12-LX or DCs). The subpopulation with QO then were divided into four smaller subpopulations, transferred to an 8-well imaging dish, and incubated with either Cy3-target at 1 uM concentration, Cy5-target at 1 μM concentration, both DNA targets (A and B) at 1 μM final concentration or 2 uL ddH$_2$O (to maintain the same buffer composition) in 37° C. for 15 min. Cells functionalized with CSP devices without QO were divided into two subpopulations and incubated with either 1 μM final concentration of each DNA targets A or B or 2 μL ddH$_2$O on the imaging dish in the same condition. All six conditions were imaged using DIC, Cy3 and Cy5 imaging settings. For real-time experiments, the Cy3-target was added at 1 μM final concentration to the subpopulation of cells functionalized with QO on the microscope stage after capturing the first image at time=0. The DIC and Cy3-fluorescence images were captured every minute. The fluorescent signal on the membrane of each cell was measured and analyzed using a home-built MATLAB code described below.

DNA Target Detection on the Membrane of DCs Seeded into the EPC

DCs were functionalized with CSP as reported (Akbari, E. et al, Adv. Mater. 2017: 29). While preparing the cells, a collagen mixture was prepared according to vendor's instructions. Briefly, the pH of high concentration rat-tail collagen I stored in acidic solution (Corning Life Sciences) was neutralized to a pH of 7.4 using NaOH in 10× PBS without MgCl$_2$/CaCl$_2$ so that the final concentration of the PBS is 1×. The mixture was prepared in a 4° C. ice bath and incubated at the same temperature for 10 min. Finally, functionalized cells were resuspended in 1× PBS without MgCl$_2$/CaCl$_2$ and mixed with collagen so that the concentration of collagen and cells are 2 mg/ml, and 7000 (cells/ μL), respectively. The final mixture was seeded into the middle channel of the EPC and incubated at 37° C. for 30 min to allow for formation of collagen matrix before imaging. Each EPC was mounted onto imaging stage and approximately 20 cells were imaged using DIC and Cy3-fluorescence settings. DNA target A at 1 uM concentration and 1×PBS were added to the EPC inlet and outlet channels respectively, and the EPC was incubated for 15 min at room temperature. Then, 20 cells were imaged using the same settings to study DNA displacement on their membrane. For real-time experiments, the Cy3-target A at 1 uM concentration and 1×PBS were added to the EPC inlet and outlet channels on the microscope stage after capturing the first image at time=0. The DIC and Cy3-fluorescence images were captured either every minute or every 5 minutes. The fluorescent signal on the membrane of each cell was measured and analyzed using a home-built MATLAB code.

Cell Periphery Fluorescent Analysis

A home-built MATLAB code previously developed (Akbari, E. et al, Adv. Mater. 2017: 29) was used to analyze the fluorescent signal on the membrane of the cells. The code measures the intensity of each pixel around the circumference of each cell and reports the mean fluorescent signal along with the angular distribution of the fluorescent signal. Between 100 and 300 cells were analyzed for each suspension experiments and near 40 cells were analyzed for collagen seeded cell experiments.

Total Internal Reflection (TIRF) Microscopy

Live cell fluorescent imaging was performed on a Nikon TiE (Belmont, CA). An ultra-thin 8-well imaging plate (LAB-TEK) was used to image the suspension samples. Fluorescent excitation was provided by 561 nm (100 mW source) or 640 nm (50 mW source) lasers for Cy3 and Cy5 channels respectively. Images were acquired using an ANDOR EMCCD camera at 160 nm/px resolution. The background noises on the DIC images were removed and the contrast and brightness were enhanced using Adobe Photoshop.

Confocal Microscopy

Confocal images were recorded using a laser scanning confocal microscopy (Nikon A1R) in the Ohio State University Campus Microscopy & Imaging Facility (CM IF). Image acquisition was performed using an EMCCD Hamamatsu camera at 1024*1024 resolution.

Fabrication of the Microfluidic Platform

The microfluidic platform was fabricated using polydimethylsiloxane (PDMS) with soft lithography. The platform outline was designed using AutoCad (AutoDesk) and patterned on a silicon wafer (University Wafers) using SU-8 2050 (MicroChem). The coated wafer was then exposed to UV light through the transparency mask, which resulted in crosslinking of the photoresist imprinting the design on the wafer. A 10:1 solution of silicon elastomer base and curing agent (Ellsworth Adhesives) was poured over the wafer, degassed, and cured at 65° C. overnight. The cured PDMS was peeled from the silicon master and cut into individual devices. Inlets and outlets on the side channels of the EPC were created with 1.5 mm biopsy punches (Militex). Individual devices were irreversibly bonded against a glass coverslip using plasma treatment. The microfluidic devices were baked overnight at 65° C. and UV sterilized for 30 min prior to the experiment (Jo, B.-H. et al, J. Microelectromechanical Syst. 2000, 9:76).

TABLE 1

| Custom Design Oligos for CSP | |
|---|---|
| Description | Sequence |
| Core | AACAATATTACCGCCTCACG CAAGTAAAGTAATTATGAAA CCATCG (SEQ ID NO: 1) |
| Core | AGTGAGCACATACGAGTGCT GCATCGGTGCGCGGAATACA CATTCAACCGATTGACATT (SEQ ID NO: 2) |
| Core | TTAGGATTTTAGTACCTAAC AGTTGATTCCCAAAACTCCT GACCCTGTAATACTTATATT (SEQ ID NO: 3) |
| Core | GGCTATTAAAACAGATTTAC ATTGGCAGAATACCTACATT TTGACCTCAAACT (SEQ ID NO: 4) |
| Core | CAACGCTAGTTGTTCCAGTT TGGTTGCGTATTGGGCGCCA GGG (SEQ ID NO: 5) |

TABLE 1-continued

Custom Design Oligos for CSP

| Description | Sequence |
| --- | --- |
| Core | GGGAAGAACCTTATGCACAG ACCAGGCGCATAGAACTGAC GCAAAAGA (SEQ ID NO: 6) |
| Core | ATACACTATTAAACGGCGAT ATATATCAGCTTCGTCCAAT AAAAAGAT (SEQ ID NO: 7) |
| Core | CACAAGAAAACATATAGCCA GCTTTCCGGCAC (SEQ ID NO: 8) |
| Core | ATTTGGGGAAACATTAAACA GGTCAGGATTAGAAAGCGGA TTGCATCACTGCGGAA (SEQ ID NO: 9) |
| Core | TAAATTGTGTCGAAATGTAA CAAAGCTGCTC (SEQ ID NO: 10) |
| Core | GCGGATAACGGAATAGGTGT ATCTCATAGTTAGCGTAACG TAAATGATCTTAAAC (SEQ ID NO: 11) |
| Core | CAAGAAACAAACGTAAACCA GGCAAAGCGCCATCGTAAAT AGCTGT (SEQ ID NO: 12) |
| Core | TTCCTGTGCGCTTTCCAGTC GGGTGAGACGGGCAACAGCT (SEQ ID NO: 13) |
| Core | AAACGGCTGTCTTTCCTTAT CATTTCATTACCCTGCGCGT (SEQ ID NO: 14) |
| Core | CAGGAGGCCGATTAACAGTG AGGCCACCGAGTTGTAGCAA TACTTC (SEQ ID NO: 15) |
| Core | ACGACAATATGTAGAAACCA ATCAATAATGAAACGCAAAG AAACGT (SEQ ID NO: 16) |
| Core | ATCTTACTCAGAGAGATAAA GCAAATCAGATATAGAAGG (SEQ ID NO: 17) |
| Core | AGAAGCCTTTCAAAGCGAAC CAGAAGCCCGAA (SEQ ID NO: 18) |
| Core | GAGTGAGACGTCACCAGTAC AAACTCAGAACCGCCACCCT GCTGAGATGGCATCA (SEQ ID NO: 19) |
| Core | ACCGAAGCGATTAAGATGCG CAACTGTTGGGAATGGGATA (SEQ ID NO: 20) |
| Core | AAATATCTTCAGTTGGGAAA ACAAAATTAATT (SEQ ID NO: 21) |
| Core | TGTTACTTAGCCGGAAACAA GAACCGGATATTGAGTAGTA AATTGGGCTTGAGATG (SEQ ID NO: 22) |

TABLE 1-continued

Custom Design Oligos for CSP

| Description | Sequence |
| --- | --- |
| Core | ATATGTGAAGAGTCAATAGT GAATTTATTAGCAAGCCCAA ATGGAAACAGTACAT (SEQ ID NO: 23) |
| Core | TAAAACGATCATGGTCCCGT GCATCTGCCAGAATAGGAAC GCCATCACAAATATTT (SEQ ID NO: 24) |
| Core | TTATAATAGGGATTTGAGCA CGCGCGCTTACCGTTTTT (SEQ ID NO: 25) |
| Core | TCAACATTGACCGTAAGGGC GAAGGCGATTAGAAAAGTAA AAACAGGGAAGCG (SEQ ID NO: 26) |
| Core | AAGAACGCGAGGCGTTAAGC CTTAAAAAACCG (SEQ ID NO: 27) |
| Core | GGGAGAAAACCAAGTTACAA TTTCTCAAACCCCAGCAAA (SEQ ID NO: 28) |
| Core | TTCGCGTCGATGGGCGCATT CGCCCCCAGTCATAGCAATA TTAACTGA (SEQ ID NO: 29) |
| Core | CAACATTATTACAGGTCTAT CATAACCCTCGTTAAATATT GGAGCCTT (SEQ ID NO: 30) |
| Core | GAGATTTGCGAGGGTACAGC AGCGTTTTTCACCAGAAAAC GAGACCT (SEQ ID NO: 31) |
| Core | TCAGAAGCAGAGTACCAAGT TTCTGAAAAGGCTCCTCAAT TTAACGG (SEQ ID NO: 32) |
| Core | TTTCGGAAATTTTCAGCTGT AGCTCAACATGTTGCGGAT (SEQ ID NO: 33) |
| Core | TAGCCGAAATAATAAGGCCT CTT (SEQ ID NO: 34) |
| Core | TAAGAGGACCGGAAGCATTC TGCGGTTTAGCTTTTTGCTC TTGATGAT (SEQ ID NO: 35) |
| Core | GAAAACTTCTACCTTAACTG ATAGCCCTAAA (SEQ ID NO: 36) |
| Core | TAAATCGGTTAGGTAAAGAT TCAAAGAGAGATCT (SEQ ID NO: 37) |
| Core | TTGAGTTATGCATGCCTGCA GGTCGACTTAGGCACTCCA (SEQ ID NO: 38) |

TABLE 1-continued

Custom Design Oligos for CSP

| Description | Sequence |
|---|---|
| Core | ACAGGAGTCAAATAAGGAAC CGCTTTTCATATAATCAGAG CTTTCA (SEQ ID NO: 39) |
| Core | CAACAGTGCAGAAGATAGTC TTTAAAGCGTAAGACAAAAC CGACCG (SEQ ID NO: 40) |
| Core | TCACAATTCCACACATAACT CACATTAATTGCCTGGCCCT GA (SEQ ID NO: 41) |
| Core | GCTTTGACTAGACAGGAAAG GAAGGGAAGAAATTAGAGCT TGACGGGGAACCATCA (SEQ ID NO: 42) |
| Core | ACATCTGATGGCCAACATAT TTTAATCTTCTG (SEQ ID NO: 43) |
| Core | ACAAAGGAGGAAGATCCTTT AGCGTCAGACT (SEQ ID NO: 44) |
| Core | ATTCTACTTCAGAGCCTCCT TTTGATAAGAGGTCTTTACC CTGACCCCCCTCAA (SEQ ID NO: 45) |
| Core | TTAAATGCAATGAGAGTCTG GAGCACCCGGTTGCGGCATT T (SEQ ID NO: 46) |
| Core | CGATTATAGACTAAAGTTAA AGGCCTCCAAAACATTGAAT TATTATAG (SEQ ID NO: 47) |
| Core | CGCCATTATCCGCGGTCACG TTGGTGTATGGCCTTCCTGT AGCCAAAAGCCCCAAAAAC (SEQ ID NO: 48) |
| Core | ATTAAGAGCAGAACCGAAAG TACGGTGTCTGGTTTAATTG ATAAAGC (SEQ ID NO: 49) |
| Core | TACCTTTTTTAATAATAAAG ACAGTAACGCCAA (SEQ ID NO: 50) |
| Core | CAAGGCCGGACACCACGGAA TAAGATACATAAAGGTGGC (SEQ ID NO: 51) |
| Core | ACCTAAATATATGCGTCTCA ACAGGACAAAAGATTAACCG TAAAAGAG (SEQ ID NO: 52) |
| Core | AAGGAATTACGAGGAAACAG TTGTTGAAAA (SEQ ID NO: 53) |
| Core | GAACGCGCGAAAAATAATAT CCCAAACCAAGTACCGCACC AAGCAAGATGCGCCG (SEQ ID NO: 54) |

TABLE 1-continued

Custom Design Oligos for CSP

| Description | Sequence |
|---|---|
| Core | GCTTAATCTAAAGCATCAAT GACCATAAATC (SEQ ID NO: 55) |
| Core | CCAGAACCCTAGCTGATAAA TTAATGCCGGAGAAACGTTA CCGTAAT (SEQ ID NO: 56) |
| Core | ATCGGCCTTTTGATTAGTAA TAAGAGAATAT (SEQ ID NO: 57) |
| Core | AATCCTTTGCCCGAACGTAT TAGACTTTACAGTTATCTA (SEQ ID NO: 58) |
| Core | CACCGACTAAAGACAAAGG GCGCCAAAAGAACTGGCATC CTTTTTAAAGTTGGGTAA (SEQ ID NO: 59) |
| Core | TGAGAGATTTCAAATAGAGA TAGAACCCTTTCACACGA (SEQ ID NO: 60) |
| Core | TTTTGCTATTCCACAGACAG CCCACCGTACTCAGGAGGTA GCGGGGATATTTTC (SEQ ID NO: 61) |
| Core | AAATCTACGTTAATAAAAAA CCAAAATAGCGCTGGATAGG CTTTCGAG (SEQ ID NO: 62) |
| Core | AATCATAAGGGAACCGGCTG GCTGACCTTCATCAACTTTA ATCATTGTGAATTA (SEQ ID NO: 63) |
| Core | CGTAGGAACCAAGAAGCTTT CCTCGTTAGAAGAGCTAAA (SEQ ID NO: 64) |
| Core | CGCTTCTGGCCAAGCTAGCC CAATAATTGAGCGCTAATA (SEQ ID NO: 65) |
| Core | AGCAAAATCAATAGAAAATT CATTTACGCAGTATGTTAGC AATGAAACGACGTTG (SEQ ID NO: 66) |
| Core | GCCGGAAGGGAACAAACGGC GGATTAAATGTGAGCGAGTA TGTCAATCATATGTAC (SEQ ID NO: 67) |
| Core | TTGTTTGGATTATACAAAGA AACCACCAGAATTTTAAAAG TTTGAGTAACATTA (SEQ ID NO: 68) |
| Core | AACCACCAAGCGGGCGCTAG GGCGCTGGCAAACTAAATCG GAACCCTGAGGTGCCGTA (SEQ ID NO: 69) |
| Core | TCGTCGCTCATAGCGATAGC TTACCGGCTTAGGTTGGGTC AATCGCAAGAATAC (SEQ ID NO: 70) |

TABLE 1-continued

Custom Design Oligos for CSP

| Description | Sequence |
| --- | --- |
| Core | TACAGTTCATATAATGGGAC AAAATCATAGGTC (SEQ ID NO: 71) |
| Core | CGTCAATAGATAATACCTAA TAGATTAGAGCCTCAAATAA TTTGAAT (SEQ ID NO: 72) |
| Core | CCGAACGAACCACCAGCCAC GCTGAGAGCCAGTCAATCAA TATCTGGTTAGGAGC (SEQ ID NO: 73) |
| Core | GGTCAGTGCAGGTCAGGAAC CGCCAAGTTTGTGTATAAGA AAATAA (SEQ ID NO: 74) |
| Core | AACAAGAGAATCGATGATTT TTAGAACCCTCATTTGCGGG AATAACCTAACGAGTA (SEQ ID NO: 75) |
| Core | GGATTCGCCATCGGAATATC ATCGCCAAGGGTTAGAACCT ACCATAT (SEQ ID NO: 76) |
| Core | GTAAAACAGAAATAAAATGA ATAATTCATTTAACATCAAC AAATCAAACCGCCTG (SEQ ID NO: 77) |
| Core | TGAAAAATTGCGCCATTAAA AATACCAGTAATAAAAGGGA GCCATTGCAACAGGA (SEQ ID NO: 78) |
| Core | TGTGATAACATAATTATATT TAACTCGAGCCAGTAATAAC AAGTGTTT (SEQ ID NO: 79) |
| Core | ACCCTCCCTATTATAACATC CAATAAATCA (SEQ ID NO: 80) |
| Core | AGACTTCATAGTAAAATGTT TAGAAGAGGCTTTTGCAAAA AGGACGTT (SEQ ID NO: 81) |
| Core | AAAAATCAGGTCATTTTTTT AAATTAGCATTTCTGAAACC CGTATAA (SEQ ID NO: 82) |
| Core | GCCTCAGGAATTTTTGTTAA ATCAGCTCATTTTTTAACCT TTGAGGG (SEQ ID NO: 83) |
| Core | TGCGAATATAGGAACCCATG TACAGAGCCACC (SEQ ID NO: 84) |
| Internals before TOH | CGTGCCAGTTCGTAACGGCC AGTGTGCCGGAGAAAATAC (SEQ ID NO: 85) |
| Internals before TOH | TCACTGCCTGAAATTGGGGT TTTATTCAGGCCTCCTTA (SEQ ID NO: 86) |

TABLE 1-continued

Custom Design Oligos for CSP

| Description | Sequence |
| --- | --- |
| Internals before TOH | CCCCCGATGCGAAAGGCACC CGCTATAACGTCGGGTATT (SEQ ID NO: 87) |
| Internals before TOH | CGCGGGGAGTGCTAGAGGAT CCCCCAGTATCG (SEQ ID NO: 88) |
| Internals before TOH | AAAGGCCGATAAAGCCAATA GTAGATGCAACTCCACCCTC CGTAACACTGAGTTT (SEQ ID NO: 89) |
| Internals before TOH | GTAATGTGTGTACCAACGCG AGCATTCCATAGCCACCCTA CAACGCCTGTAGCA (SEQ ID NO: 90) |
| Internals before TOH | CATGGAATTCACCAGCTGAC CTGAATGCGCGTTTAACCTG ATTAAGACGCTGAGA (SEQ ID NO: 91) |
| Internals before TOH | ATGATATTACAGCAAGGCAA AGAAGGCTTAGA (SEQ ID NO: 92) |
| Internals before TOH | TCATCAGTCCAGAACCATTA CCCAAATCAACCCGCGACGT ACAACG (SEQ ID NO: 93) |
| Internals before TOH | AACGGAAGTTTAATTTCAAG AGTAATCTTGCGAGGCGCCC CCCAG (SEQ ID NO: 94) |
| Internals before TOH | ATTTAGAAGTTATTAAGGAG CGGAATTATCAATCAATAT (SEQ ID NO: 95) |
| Internals before TOH | AACTAATGTCAGTGAATAAG GCTTGCCCTGACG (SEQ ID NO: 96) |
| Bottom Over Hangs | GATTGCCGCAAAATCCCTTA TATTACAAAATAAACAGCCT CTGGTTAACGTGTCTGGGC (SEQ ID NO: 97) |
| Bottom Over Hangs | GAGAGTTGCAGCAAAATCCT GTTTGATAATCCAAATAAGA AACCTCTGGTTAACGTGTCT GGGC (SEQ ID NO: 98) |
| Bottom Over Hangs | CCCAAATCAAGTTTTCAACG TCAAAGGGCGAATCAAGATT AGTTGCTCTGGTTAACGTGT CTGGGC (SEQ ID NO: 99) |
| Bottom Over Hangs | AAGCGAGGCGGTAACAAGAG TCCACTATTACAATTTTATC CTGACTCTGGTTAACGTGTC TGGGC (SEQ ID NO: 100) |
| Bottom Over Hangs | TGGTTTTTCTTCGAGATAGG GTTGAGTACGAGCGTCTTTC CAGCTCTGGTTAACGTGTCT GGGC (SEQ ID NO: 101) |

TABLE 1-continued

Custom Design Oligos for CSP

| Description | Sequence |
|---|---|
| Bottom Over Hangs | ATGCTTTCATAGTAAGCGGG ATCGTCACCCTGCAACGGCA AAGGAATCTCTGGTTAACGT GTCTGGGC (SEQ ID NO: 102) |
| Bottom Over Hangs | TCGTCATTACCAGATGAGGC TTGCAGGGAGACTTTTTCTT CAGCGCTCTGGTTAACGTGT CTGGGC (SEQ ID NO: 103) |
| Bottom Over Hangs | TGCTGAACCAGATACACTGA TTGCTTTGAATCAATAACAA ATCAATCTCTGGTTAACGTG TCTGGGC (SEQ ID NO: 104) |
| Bottom Over Hangs | ATTCATTTTGCGGAACTTCT GAATAATGGTGACTCTGGTT AACGTGTCTGGGC (SEQ ID NO: 105) |
| Bottom Over Hangs | AACAACCATCGCCCACGCAT AACGTAAAATAGTATGGGAC TCTGGTTAACGTGTCTGGGC (SEQ ID NO: 106) |
| Bottom Over Hangs | GCGCAGAGGCGAATTTACAG TAATCTGTAAACTCTGGTTA ACGTGTCTGGGC (SEQ ID NO: 107) |
| Bottom Over Hangs | TAATTGTATCAACAGTATGA GGAAGTTTCCAAAACACTCA TCTTTGAAGACGGTCCTCTG GTTAACGTGTCTGGGC (SEQ ID NO: 108) |
| Bottom Over Hangs | GTGAATTATTTTCTCGTAAT GCCACTACGCCTAAAACGAA AGAGCAACTTTGCTCTGGTT AACGTGTCTGGGC (SEQ ID NO: 109) |
| Bottom Over Hangs | TCTCCAAGAACAACTTACAG AGGCTTTGAGCCAAGCGCGA AACAAACTGCTCCACTCTGG TTAACGTGTCTGGGC (SEQ ID NO: 110) |
| Bottom Over Hangs | CCTTGCTCAGTACCTTTTAC ATCCAAAATTATTTGCACAA TCCTGACTCTGGTTAACGTG TCTGGGC (SEQ ID NO: 111) |
| Bottom Over Hangs | TCGGTCATGGTGAATTTAAA GCCAGAATGGAACGTCATAC ATGGCTTAGTACCAGCTCTG GTTAACGTGTCTGGGC (SEQ ID NO: 112) |
| Bottom Over Hangs | CAGTAGCGGCACCATTGACA GGAGGTTGAGGCCTTGAGTA ACAGTGCATGAAAGTCTCTG GTTAACGTGTCTGGGC (SEQ ID NO: 113) |
| Bottom Over Hangs | TTGGGAATCCTTGATATTCA CAAAGTACTGGTAATAAGTG AGAAGGACTCTGGTTAACGT GTCTGGGC (SEQ ID NO: 114) |

TABLE 1-continued

Custom Design Oligos for CSP

| Description | Sequence |
|---|---|
| Bottom Over Hangs | AAAAGCCCCCTTCACCGGAA CCAGAGCCACCACCATCCTC ATATCACCGTCTCTGGTTAA CGTGTCTGGGC (SEQ ID NO: 115) |
| Bottom Over Hangs | TGTTCAGAAGCCTGTTTAGT ATCTTAATGGTTTGAAATGA ACGCGACTCTGGTTAACGTG TCTGGGC (SEQ ID NO: 116) |
| Bottom Over Hangs | CACCACTGTTCTTACACCAC CAGATGCCCCCTGCATTTCG TTACTACTCTGGTTAACGTG TCTGGGC (SEQ ID NO: 117) |
| Bottom Over Hangs | AGCCTAATAACAAAGTCAGA GGGTAATAAGAGCTCTGGTT AACGTGTCTGGGC (SEQ ID NO: 118) |
| Bottom Over Hangs | CATATTATCATTAGACGGGA GAAGCTATCTTCTCTGGTTA ACGTGTCTGGGC (SEQ ID NO: 119) |
| Bottom Over Hangs | GATTTTTTACAGAGAGAATA ACATAAGCAGACTCTGGTTA ACGTGTCTGGGC (SEQ ID NO: 120) |
| Bottom Over Hangs | CTATTTTGCTTATCCGGTAT TCTATTTTCATCTCTGGTTA ACGTGTCTGGGC (SEQ ID NO: 121) |
| Bottom Over Hangs | TCTGTCCAAAGAGCGGTCAG ATCCGGTCACGGCGCCCAAT AGCACCCTCTGGTTAACGTG TCTGGGC (SEQ ID NO: 122) |
| Bottom Over Hangs | AAATTGTAGGGTAGCAGCCA CCACCCTCAGACCAGCATTA CCATTAGCTCTGGTTAACGT GTCTGGGC (SEQ ID NO: 123) |
| Bottom Over Hangs | TCGCATTACAACCGTTCAGT ATAAAGCCAACGTATACAAA TCCAGACGCTCTGGTTAACG TGTCTGGGC (SEQ ID NO: 124) |
| Bottom Over Hangs | CTATCAGGGAGCCGCCACCC TCAACGATTGGTAGAGCCCT CTGGTTAACGTGTCTGGGC (SEQ ID NO: 125) |
| Bottom Over Hangs | TGCTGGTATAATTGAGAATC GCCACTAGAAACTAATGCAC TCTGGTTAACGTGTCTGGGC (SEQ ID NO: 126) |
| End Staples | TCTATCAGGGCGATTTTT (SEQ ID NO: 127) |

TABLE 1-continued

Custom Design Oligos for CSP

| Description | Sequence |
|---|---|
| End Staples | TTTTTTTTGCCCCAGCAGGC GAAGCGGTCCACGCTGGTTT TT (SEQ ID NO: 127) |
| End Staples | TTTTTTGGCCCACTACGTGA AAGCCGGCGTTTTT (SEQ ID NO: 128) |
| End Staples | TTTTTAAGCCTGGGGTGCCT AATG (SEQ ID NO: 129) |
| End Staples | TTTTTAACGTGGCGAGAACG GTACGCCTTTTT (SEQ ID NO: 130) |
| End Staples | CTACAGGGCGCTTTTT (SEQ ID NO: 131) |
| End Staples | TTTTTCAGCTGGCGAAAGGG GGAT (SEQ ID NO: 132) |
| End Staples | TTTTTGTACTATGGTT (SEQ ID NO: 133) |
| End Staples | CGCTATTACGCTTTTT (SEQ ID NO: 134) |
| End Staples | TTTTTGATTCTCCGTGCATA AAGTGTATTTTT (SEQ ID NO: 135) |
| End Staples | TTTTTAGAATCCTGAGATCA CTTGCCTTTTT (SEQ ID NO: 136) |
| End Staples | TTTTTTAAAACTAGCAACAA CCCGTCGTTTTT (SEQ ID NO: 137) |
| End Staples | TTTTTGAGTAGAAGAAGCTC AATCGTCTTTTT (SEQ ID NO: 138) |
| End Staples | TTTTTCAAGGATAAAAAACG GTAATCGTTTTT (SEQ ID NO: 139) |
| End Staples | TTTTTTGAAATGGATTAGGT GAGGCGGTTTTT (SEQ ID NO: 140) |
| End Staples | GTGGCACAGACATTTTT (SEQ ID NO: 141) |
| End Staples | TTTTTATACATTTCGCAAAT GGTC (SEQ ID NO: 142) |
| End Staples | TTTTTATATTTTTGAAT (SEQ ID NO: 143) |
| End Staples | GATTTAGTTTGACCATTAGT TTTT (SEQ ID NO: 144) |
| End Staples | TTTTTTTAATTCGAGCTTAT TTCAACGTTTTT (SEQ ID NO: 145) |
| End Staples | TTTTTTCAGTATTAACCAGT TGAAAGGTTTTT (SEQ ID NO: 146) |

TABLE 1-continued

Custom Design Oligos for CSP

| Description | Sequence |
|---|---|
| End Staples | TTTTTAGAGGGGGTAAAATA TCGCGTTTTTTT (SEQ ID NO: 147) |
| End Staples | TTTTTAATTGAGGAAGAACA ATTCGACTTTTT (SEQ ID NO: 148) |
| End Staples | TTTTTTTATACCAGTCGAAG TTTTGCCTTTTT (SEQ ID NO: 149) |
| End Staples | TTTTTAACTCGTATTA (SEQ ID NO: 150) |
| End Staples | TTTTTATGAACGGTGTGATT TTAAGAACTGGCTCATTTTT (SEQ ID NO: 151) |
| End Staples | TTTTTCAGATGATGGCAATT CTCATATTCCTGATTATTTT TT (SEQ ID NO: 152) |
| End Staples | AAAGAGGACAGTTTTT (SEQ ID NO: 153) |
| End Staples | TTTTTACCAAAAGGCTTTTT (SEQ ID NO: 154) |
| End Staples | TTTTTTCAGGTTTAACGTCA GGAAATTGCGTAGATTTTTT TT (SEQ ID NO: 155) |
| End Staples | TTTTTTTGCGCCGACAATGA CAGCTTGATACCGATAGTTT TT (SEQ ID NO: 156) |
| End Staples | TTTTTAGAAGATGATGAAAC ACAATTACCTGAGCAAATTT TT (SEQ ID NO: 157) |
| End Staples | TTTTTGTCTTTCCAGACGTT AGATCTAAAGTTTTGTCTTT TT (SEQ ID NO: 158) |
| End Staples | TTTTTTTAGAATCCTTGAAA AATTAATTAATTTTCCCTTT TT (SEQ ID NO: 159) |
| End Staples | TTTTTTTGATATAAGTATAGC CGTGCCGTCGAGAGGGTTTT TT (SEQ ID NO: 160) |
| End Staples | TTTTTAATGCTGATGCAAAT CTATATAACTATATGTATTT TT (SEQ ID NO: 161) |
| End Staples | TTTTTTTACCGTTCCAGTAA GAGCGCAGTCTCTGAATTTT TT (SEQ ID NO: 162) |
| End Staples | TTTTTGAATAAACACCGGAA TATAAGGCGTTAAATAATTT TT (SEQ ID NO: 163) |

TABLE 1-continued

| Custom Design Oligos for CSP | |
| --- | --- |
| Description | Sequence |
| End Staples | TTTTTCTTTTCATAATCAAA ATATTAGCGTTTGCCATTTT TT (SEQ ID NO: 164) |
| End Staples | TTTTTTTAGGCAGAGGCATT TAACGCCAACATGTAATTTT TT (SEQ ID NO: 165) |
| End Staples | TTTTTATTGACGGAAATTAT TGGGAGGGAAGGTAAATTTT TT (SEQ ID NO: 166) |
| End Staples | TTTTTGATAAGTCCTGAACA ACTGTTTATCAACAATATTT TT (SEQ ID NO: 167) |
| End Staples | TTTTTAAACCGAGGAAACGC ACAAAGTTACCAGAAGGTTT TT (SEQ ID NO: 168) |
| End Staples | TTTTTGAGAATCATCTTTTT (SEQ ID NO: 169) |
| End Staples | TTTTTGAAAATAGCAGCCTT TGTTTAACGTCAAAAATTTT TT (SEQ ID NO: 170) |
| End Staples | TTTTTCTTGCGGGAGGTTTT GTTAGCGAACCTCCCGATTT TT (SEQ ID NO: 171) |
| Top Overhangs Replacement | CACCCAGCTAAAGAACGTGG ACTCTTGGGGTCAAAGGGAG (SEQ ID NO: 172) |
| Top Overhangs Replacement | GACGACGAGGGTACCGAGCT CGAACTGCATTAATGAATCG GCCAACG (SEQ ID NO: 173) |
| Top Overhangs Replacement | ACACCCTGTTGCCAGAATCA AAAGAATAGCCTTCACCAGA AACCTGT (SEQ ID NO: 174) |
| Top Overhangs Replacement | TTATCCCGGTGGTTCCGAAA TCGCTTCACCGCGTTGCGC (SEQ ID NO: 175) |
| Top Overhangs Replacement | ATCCTAATTTACGAGCAAAC AACAAAAGTACCTAGGGCTA TATCCAGAAAACGCT (SEQ ID NO: 176) |
| Top Overhangs Replacement | TTAGCAAAATTAAGCAGAGA CAGTCAAATCACCATCAAT (SEQ ID NO: 177) |
| Top Overhangs Replacement | TTTATTTTGTCACAATCACC AGTAACAGAATCACCCTCAG TATTTTTAGGGTGAG (SEQ ID NO: 178) |
| Top Overhangs Replacement | ATGGTTTACCAGCGCCTGAG CCATGTAGCGCGCTCCCTCA TCATTGCCTGCCTGA (SEQ ID NO: 179) |

TABLE 1-continued

| Custom Design Oligos for CSP | |
| --- | --- |
| Description | Sequence |
| Top Overhangs Replacement | GTGAATAAACATTTAACAAA ATCACTAACAAATTTGAGG (SEQ ID NO: 180) |
| Top Overhangs Replacement | AGAAACATGAGATTTAGGAA TACCACATTC (SEQ ID NO: 181) |
| Top Overhangs Replacement | ATAGAAAGAAAAAAGGCGCT TTTGAGCAACAAGAAAGAT (SEQ ID NO: 182) |
| Top Overhangs Replacement | AACAACTTTCGGTTTTCGGT CGCCGACGATAAACGAACT (SEQ ID NO: 183) |

TABLE 2

| Custom design oligos for detection modules | |
| --- | --- |
| Cy5-labeled Detection Module on Location C3 | |
| Internal Cy5 Oligo_C3 | ATAGAAAGAAAAAAGGCGCTTTTG AGCAACAAGAAAGAT/Cy5 (SEQ ID NO: 184) |
| Top Overhang_C3 | CGGTCATAAGCGCTCACGGATAGG TTTTCATCAGTCCAGAACCATTAC CCAAATCAACCCGCGACGTACAA CG (SEQ ID NO: 185) |
| QO_C3 | Iowa Black® FQ/ACCTATCC GTGAGCGCTTA (SEQ ID NO: 186) |
| C3_Target | ACCTATCCGTGAGCGCTTATGAC CG (SEQ ID NO: 187) |
| Cy3-labeled Detection Module on Location C4 | |
| Internal Cy3 Oligo_C4 | AACAACTTTCGGTTTTCGGTCGC CGACGATAAACGAACT/Cy3 (SEQ ID NO: 188) |
| Top Overhang _C4 | CGAAGTCACTCCCAGGCAGCTCC AATTAACGGAAGTTTAATTTCA AGAGTAATCTTGCGAGGCGC CCCCCAG (SEQ ID NO: 189) |
| QO_C4 | Iowa Black® FQ/TTGGAGC TGCCTGGGAGTG (SEQ ID NO: 190) |
| C4_Target | TTGGAGCTGCCTGGGAGTG ACTTCG (SEQ ID NO: 191) |

TABLE 3

| DNA oligos used for cell functionalization Cell Membrane Incorporation Oligos | |
| --- | --- |
| Cholesterol Conjugated Oligo | GATGAATGGTGGGTGAGAGG/CholTEG/ (SEQ ID NO: 192) |
| Bridge Oligo | CCTCTCACCCACCATTCATCTTTTTT TTTTTTTTTTTTGCCCAGACACGTTA ACCAGAG (SEQ ID NO: 193) |

TABLE 3 -continued

| DNA oligos used for cell functionalization Cell Membrane Incorporation Oligos | | |
| --- | --- | --- |
| Fortifier Oligo | AAAAAAAAAAAAAAAAAA (SEQ ID NO: 194) | |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

The invention claimed is:

1. A microfluidic culture system, comprising i) a 3D culture chamber comprising cells functionalized with cell sensors and incorporated into a 3D culture scaffold, and ii) one or more microfluidic channels fluidly connected to the 3D culture chamber by apertures, wherein the cell sensors comprise a planar nucleic acid nanostructure having a top surface and a bottom surface, a first sensor molecule that binds a first target molecule attached to the top surface, a second sensor molecule that binds a second target molecule attached to the top surface, and one or more membrane anchoring moieties attached to the bottom surface anchoring the cell sensors to the cells, wherein first sensor molecule is a double stranded oligonucleotide comprising a first fluorescent strand attached to the top surface that binds the first target molecule and a first quenching strand bound to the first fluorescent strand, wherein the first quenching strand comprises a first quencher fluorophore and the first fluorescent strand comprises a first donor fluorophore that is quenched by the first quencher fluorophore in the absence of the first target molecule, wherein binding of the first fluorescent strand to the first target molecule displaces the first quenching strand from the first fluorescent strand, wherein second sensor molecule is a double stranded oligonucleotide comprising a second fluorescent strand attached to the top surface that binds the second target molecule and a second quenching strand bound to the second fluorescent strand, wherein the second quenching strand comprises a second quencher fluorophore and the second fluorescent strand comprises a second donor fluorophore that is quenched by the second quencher fluorophore in the absence of the second target molecule, wherein binding of the second fluorescent strand to the second target molecule displaces the second quenching strand from the second fluorescent strand, and wherein the first donor fluorophore and second donor fluorophore emit at different wavelengths.

2. The microfluidic culture system of claim 1, wherein the membrane anchoring moiety comprises a hydrophobic anchor.

3. The microfluidic culture system of claim 2, wherein the membrane anchoring moiety comprises a cholesterol.

4. The microfluidic culture system of claim 1, wherein the first and second sensor molecules are present on the top surface at a ratio of 1:1.

5. The microfluidic culture system of claim 1, further comprising a third sensor molecule that binds a third target molecule, wherein third sensor molecule is a double stranded oligonucleotide comprising a third fluorescent strand attached to the top surface that binds the third target molecule and a third quenching strand bound to the third fluorescent strand, wherein the third quenching strand comprises a third quencher fluorophore and the third fluorescent strand comprises a third donor fluorophore that is quenched by the third quencher fluorophore in the absence of the third target molecule, wherein binding of the third fluorescent strand to the third target molecule displaces the third quenching strand from the third third fluorescent, and wherein the first donor fluorophore, second donor fluorophore, and third donor fluorophore emit at different wavelengths.

6. The microfluidic culture system of claim 5, wherein the first, second, and third sensor molecules are present on the top surface at a ratio of 1:1:1.

7. The microfluidic culture system of claim 1, further comprising a fourth sensor molecule that binds a fourth target molecule, wherein fourth sensor molecule is a double stranded oligonucleotide comprising a fourth fluorescent strand attached to the top surface that binds the fourth target molecule and a fourth quenching strand bound to the fourth fluorescent strand, wherein the fourth quenching strand comprises a fourth quencher fluorophore and the fourth fluorescent strand comprises a fourth donor fluorophore that is quenched by the fourth quencher fluorophore in the absence of the fourth target molecule, wherein binding of the fourth fluorescent strand to the fourth target molecule displaces the fourth quenching strand from the fourth fluorescent strand, and wherein the first donor fluorophore, second donor fluorophore, third donor fluorophore, and fourth donor fluorophore emit at different wavelengths.

8. The microfluidic culture system of claim 7, wherein the first, second, third, and fourth sensor molecules are present on the top surface at a ratio of 1:1:1:1.

9. The microfluidic culture system of claim 1, wherein the planar nucleic acid nanostructure comprises a rationally designed DNA origami nanostructure.

10. The microfluidic culture system of claim 9, wherein the DNA origami nanostructure comprises a top layer, a bottom layer, and optionally at least one middle layer, wherein the top layer and the bottom layer each comprise 10 or more double-stranded DNA (dsDNA) helices linearly aligned into a planar sheet.

11. The microfluidic culture system of claim 10, wherein the middle layer is not contiguous and comprises voids.

12. The microfluidic culture system of claim 1, wherein the cell is a cancer cell.

13. A method for culturing cells, providing the microfluidic culture system of claim 1; seeding cells in the 3D culture matrix; exposing the seeded cells to a flow of culture media for a period of time, and monitoring the cells for sensor binding.

14. The method of claim 13, further comprising adding one or more target molecules to the culture media.

15. The method of claim 14, wherein the cells are monitored for sensor binding by fluorescence microscopy.

* * * * *

```
                         SEQUENCE LISTING

Sequence total quantity: 194
SEQ ID NO: 1              moltype = DNA   length = 46
FEATURE                  Location/Qualifiers
source                   1..46
                         mol_type = other DNA
                         organism = synthetic construct
SEQUENCE: 1
aacaatatta ccgcctcacg caagtaaagt aattatgaaa ccatcg              46

SEQ ID NO: 2              moltype = DNA   length = 59
FEATURE                  Location/Qualifiers
source                   1..59
                         mol_type = other DNA
                         organism = synthetic construct
SEQUENCE: 2
agtgagcaca tacgagtgct gcatcggtgc gcggaataca cattcaaccg attgacatt   59

SEQ ID NO: 3              moltype = DNA   length = 60
FEATURE                  Location/Qualifiers
source                   1..60
                         mol_type = other DNA
                         organism = synthetic construct
SEQUENCE: 3
ttaggatttt agtacctaac agttgattcc caaaactcct gaccctgtaa tacttatatt   60

SEQ ID NO: 4              moltype = DNA   length = 53
FEATURE                  Location/Qualifiers
source                   1..53
                         mol_type = other DNA
                         organism = synthetic construct
SEQUENCE: 4
ggctattaaa acagatttac attggcagaa tacctacatt ttgacctcaa act          53

SEQ ID NO: 5              moltype = DNA   length = 43
FEATURE                  Location/Qualifiers
source                   1..43
                         mol_type = other DNA
                         organism = synthetic construct
SEQUENCE: 5
caacgctagt tgttccagtt tggttgcgta ttgggcgcca ggg                  43

SEQ ID NO: 6              moltype = DNA   length = 48
FEATURE                  Location/Qualifiers
source                   1..48
                         mol_type = other DNA
                         organism = synthetic construct
SEQUENCE: 6
gggaagaacc ttatgcacag accaggcgca tagaactgac gcaaaaga            48

SEQ ID NO: 7              moltype = DNA   length = 48
FEATURE                  Location/Qualifiers
source                   1..48
                         mol_type = other DNA
                         organism = synthetic construct
SEQUENCE: 7
atacactatt aaacggcgat atatatcagc ttcgtccaat aaaaagat            48

SEQ ID NO: 8              moltype = DNA   length = 32
FEATURE                  Location/Qualifiers
source                   1..32
                         mol_type = other DNA
                         organism = synthetic construct
SEQUENCE: 8
cacaagaaaa catatagcca gctttccggc ac                            32
```

-continued

```
SEQ ID NO: 9              moltype = DNA   length = 56
FEATURE                   Location/Qualifiers
source                    1..56
                          mol_type = other DNA
                          organism = synthetic construct
SEQUENCE: 9
atttggggaa acattaaaca ggtcaggatt agaaagcgga ttgcatcact gcggaa        56

SEQ ID NO: 10             moltype = DNA   length = 31
FEATURE                   Location/Qualifiers
source                    1..31
                          mol_type = other DNA
                          organism = synthetic construct
SEQUENCE: 10
taaattgtgt cgaaatgtaa caaagctgct c                                   31

SEQ ID NO: 11             moltype = DNA   length = 55
FEATURE                   Location/Qualifiers
source                    1..55
                          mol_type = other DNA
                          organism = synthetic construct
SEQUENCE: 11
gcggataacg gaataggtgt atctcatagt tagcgtaacg taaatgatct taaac         55

SEQ ID NO: 12             moltype = DNA   length = 46
FEATURE                   Location/Qualifiers
source                    1..46
                          mol_type = other DNA
                          organism = synthetic construct
SEQUENCE: 12
caagaaacaa acgtaaacca ggcaaagcgc catcgtaaat agctgt                   46

SEQ ID NO: 13             moltype = DNA   length = 40
FEATURE                   Location/Qualifiers
source                    1..40
                          mol_type = other DNA
                          organism = synthetic construct
SEQUENCE: 13
ttcctgtgcg ctttccagtc gggtgagacg ggcaacagct                         40

SEQ ID NO: 14             moltype = DNA   length = 40
FEATURE                   Location/Qualifiers
source                    1..40
                          mol_type = other DNA
                          organism = synthetic construct
SEQUENCE: 14
aaacggctgt ctttccttat catttcatta ccctgcgcgt                         40

SEQ ID NO: 15             moltype = DNA   length = 46
FEATURE                   Location/Qualifiers
source                    1..46
                          mol_type = other DNA
                          organism = synthetic construct
SEQUENCE: 15
caggaggccg attaacagtg aggccaccga gttgtagcaa tacttc                   46

SEQ ID NO: 16             moltype = DNA   length = 46
FEATURE                   Location/Qualifiers
source                    1..46
                          mol_type = other DNA
                          organism = synthetic construct
SEQUENCE: 16
acgacaatat gtagaaacca atcaataatg aaacgcaaag aaacgt                   46

SEQ ID NO: 17             moltype = DNA   length = 39
FEATURE                   Location/Qualifiers
source                    1..39
                          mol_type = other DNA
                          organism = synthetic construct
SEQUENCE: 17
atcttactca gagagataaa gcaaatcaga tatagaagg                          39

SEQ ID NO: 18             moltype = DNA   length = 32
FEATURE                   Location/Qualifiers
source                    1..32
                          mol_type = other DNA
                          organism = synthetic construct
SEQUENCE: 18
agaagccttt caaagcgaac cagaagcccg aa                                  32
```

-continued

```
SEQ ID NO: 19            moltype = DNA  length = 55
FEATURE                  Location/Qualifiers
source                   1..55
                         mol_type = other DNA
                         organism = synthetic construct
SEQUENCE: 19
gagtgagacg tcaccagtac aaactcagaa ccgccaccct gctgagatgg catca        55

SEQ ID NO: 20            moltype = DNA  length = 40
FEATURE                  Location/Qualifiers
source                   1..40
                         mol_type = other DNA
                         organism = synthetic construct
SEQUENCE: 20
accgaagcga ttaagatgcg caactgttgg gaatgggata                          40

SEQ ID NO: 21            moltype = DNA  length = 32
FEATURE                  Location/Qualifiers
source                   1..32
                         mol_type = other DNA
                         organism = synthetic construct
SEQUENCE: 21
aaatatcttc agttgggaaa acaaaattaa tt                                  32

SEQ ID NO: 22            moltype = DNA  length = 56
FEATURE                  Location/Qualifiers
source                   1..56
                         mol_type = other DNA
                         organism = synthetic construct
SEQUENCE: 22
tgttacttag ccggaaacaa gaaccggata ttgagtagta aattgggctt gagatg        56

SEQ ID NO: 23            moltype = DNA  length = 55
FEATURE                  Location/Qualifiers
source                   1..55
                         mol_type = other DNA
                         organism = synthetic construct
SEQUENCE: 23
atatgtgaag agtcaatagt gaatttatta gcaagcccaa atggaaacag tacat         55

SEQ ID NO: 24            moltype = DNA  length = 56
FEATURE                  Location/Qualifiers
source                   1..56
                         mol_type = other DNA
                         organism = synthetic construct
SEQUENCE: 24
taaaacgatc atggtcccgt gcatctgcca gaataggaac gccatcacaa atattt        56

SEQ ID NO: 25            moltype = DNA  length = 38
FEATURE                  Location/Qualifiers
source                   1..38
                         mol_type = other DNA
                         organism = synthetic construct
SEQUENCE: 25
ttataatagg gatttgagca cgcgcgctta ccgttttt                            38

SEQ ID NO: 26            moltype = DNA  length = 53
FEATURE                  Location/Qualifiers
source                   1..53
                         mol_type = other DNA
                         organism = synthetic construct
SEQUENCE: 26
tcaacattga ccgtaagggc gaaggcgatt agaaaagtaa aaacagggaa gcg           53

SEQ ID NO: 27            moltype = DNA  length = 32
FEATURE                  Location/Qualifiers
source                   1..32
                         mol_type = other DNA
                         organism = synthetic construct
SEQUENCE: 27
aagaacgcga ggcgttaagc cttaaaaaac cg                                  32

SEQ ID NO: 28            moltype = DNA  length = 39
FEATURE                  Location/Qualifiers
source                   1..39
                         mol_type = other DNA
                         organism = synthetic construct
SEQUENCE: 28
```

```
gggagaaaac caagttacaa tttctcaaac cccagcaaa                              39

SEQ ID NO: 29         moltype = DNA   length = 48
FEATURE               Location/Qualifiers
source                1..48
                      mol_type = other DNA
                      organism = synthetic construct
SEQUENCE: 29
ttcgcgtcga tggcgcatt cgcccccagt catagcaata ttaactga                    48

SEQ ID NO: 30         moltype = DNA   length = 48
FEATURE               Location/Qualifiers
source                1..48
                      mol_type = other DNA
                      organism = synthetic construct
SEQUENCE: 30
caacattatt acaggtctat cataaccctc gttaaatatt ggagcctt                    48

SEQ ID NO: 31         moltype = DNA   length = 47
FEATURE               Location/Qualifiers
source                1..47
                      mol_type = other DNA
                      organism = synthetic construct
SEQUENCE: 31
gagatttgcg agggtacagc agcgtttttc accagaaaac gagacct                     47

SEQ ID NO: 32         moltype = DNA   length = 47
FEATURE               Location/Qualifiers
source                1..47
                      mol_type = other DNA
                      organism = synthetic construct
SEQUENCE: 32
tcagaagcag agtaccaagt ttctgaaaag gctcctcaat ttaacgg                     47

SEQ ID NO: 33         moltype = DNA   length = 39
FEATURE               Location/Qualifiers
source                1..39
                      mol_type = other DNA
                      organism = synthetic construct
SEQUENCE: 33
tttcggaaat tttcagctgt agctcaacat gttgcggat                             39

SEQ ID NO: 34         moltype = DNA   length = 23
FEATURE               Location/Qualifiers
source                1..23
                      mol_type = other DNA
                      organism = synthetic construct
SEQUENCE: 34
tagccgaaat aataaggcct ctt                                              23

SEQ ID NO: 35         moltype = DNA   length = 48
FEATURE               Location/Qualifiers
source                1..48
                      mol_type = other DNA
                      organism = synthetic construct
SEQUENCE: 35
taagaggacc ggaagcattc tgcggtttag ctttttgctc ttgatgat                   48

SEQ ID NO: 36         moltype = DNA   length = 31
FEATURE               Location/Qualifiers
source                1..31
                      mol_type = other DNA
                      organism = synthetic construct
SEQUENCE: 36
gaaaacttct accttaactg atagccctaa a                                     31

SEQ ID NO: 37         moltype = DNA   length = 34
FEATURE               Location/Qualifiers
source                1..34
                      mol_type = other DNA
                      organism = synthetic construct
SEQUENCE: 37
taaatcggtt aggtaaagat tcaaagagag atct                                  34

SEQ ID NO: 38         moltype = DNA   length = 39
FEATURE               Location/Qualifiers
source                1..39
                      mol_type = other DNA
                      organism = synthetic construct
```

```
SEQUENCE: 38
ttgagttatg catgcctgca ggtcgactta ggcactcca                                39

SEQ ID NO: 39          moltype = DNA  length = 46
FEATURE                Location/Qualifiers
source                 1..46
                       mol_type = other DNA
                       organism = synthetic construct
SEQUENCE: 39
acaggagtca aataaggaac cgcttttcat ataatcagag ctttca                        46

SEQ ID NO: 40          moltype = DNA  length = 46
FEATURE                Location/Qualifiers
source                 1..46
                       mol_type = other DNA
                       organism = synthetic construct
SEQUENCE: 40
caacagtgca gaagatagtc tttaaagcgt aagacaaaac cgaccg                        46

SEQ ID NO: 41          moltype = DNA  length = 42
FEATURE                Location/Qualifiers
source                 1..42
                       mol_type = other DNA
                       organism = synthetic construct
SEQUENCE: 41
tcacaattcc acacataact cacattaatt gcctggccct ga                           42

SEQ ID NO: 42          moltype = DNA  length = 56
FEATURE                Location/Qualifiers
source                 1..56
                       mol_type = other DNA
                       organism = synthetic construct
SEQUENCE: 42
gctttgacta gacaggaaag gaagggaaga aattagagct tgacggggaa ccatca            56

SEQ ID NO: 43          moltype = DNA  length = 32
FEATURE                Location/Qualifiers
source                 1..32
                       mol_type = other DNA
                       organism = synthetic construct
SEQUENCE: 43
acatctgatg gccaacatat tttaatcttc tg                                      32

SEQ ID NO: 44          moltype = DNA  length = 31
FEATURE                Location/Qualifiers
source                 1..31
                       mol_type = other DNA
                       organism = synthetic construct
SEQUENCE: 44
acaaaggagg aagatccttt agcgtcagac t                                       31

SEQ ID NO: 45          moltype = DNA  length = 54
FEATURE                Location/Qualifiers
source                 1..54
                       mol_type = other DNA
                       organism = synthetic construct
SEQUENCE: 45
attctacttc agagcctcct tttgataaga ggtctttacc ctgacccccc tcaa              54

SEQ ID NO: 46          moltype = DNA  length = 41
FEATURE                Location/Qualifiers
source                 1..41
                       mol_type = other DNA
                       organism = synthetic construct
SEQUENCE: 46
ttaaatgcaa tgagagtctg gagcacccgg ttgcggcatt t                           41

SEQ ID NO: 47          moltype = DNA  length = 48
FEATURE                Location/Qualifiers
source                 1..48
                       mol_type = other DNA
                       organism = synthetic construct
SEQUENCE: 47
cgattataga ctaaagttaa aggcctccaa aacattgaat tattatag                     48

SEQ ID NO: 48          moltype = DNA  length = 59
FEATURE                Location/Qualifiers
source                 1..59
                       mol_type = other DNA
```

```
                          organism = synthetic construct
SEQUENCE: 48
cgccattatc cgcggtcacg ttggtgtatg gccttcctgt agccaaaagc cccaaaaac    59

SEQ ID NO: 49           moltype = DNA  length = 47
FEATURE                 Location/Qualifiers
source                  1..47
                        mol_type = other DNA
                        organism = synthetic construct
SEQUENCE: 49
attaagagca gaaccgaaag tacggtgtct ggtttaattg ataaagc               47

SEQ ID NO: 50           moltype = DNA  length = 33
FEATURE                 Location/Qualifiers
source                  1..33
                        mol_type = other DNA
                        organism = synthetic construct
SEQUENCE: 50
tacctttttt aataataaag acagtaacgc caa                              33

SEQ ID NO: 51           moltype = DNA  length = 39
FEATURE                 Location/Qualifiers
source                  1..39
                        mol_type = other DNA
                        organism = synthetic construct
SEQUENCE: 51
caaggccgga caccacggaa taagatacat aaaggtggc                        39

SEQ ID NO: 52           moltype = DNA  length = 48
FEATURE                 Location/Qualifiers
source                  1..48
                        mol_type = other DNA
                        organism = synthetic construct
SEQUENCE: 52
acctaaatat atgcgtctca acaggacaaa agattaaccg taaaagag             48

SEQ ID NO: 53           moltype = DNA  length = 30
FEATURE                 Location/Qualifiers
source                  1..30
                        mol_type = other DNA
                        organism = synthetic construct
SEQUENCE: 53
aaggaattac gaggaaacag ttgttgaaaa                                  30

SEQ ID NO: 54           moltype = DNA  length = 55
FEATURE                 Location/Qualifiers
source                  1..55
                        mol_type = other DNA
                        organism = synthetic construct
SEQUENCE: 54
gaacgcgcga aaataatat cccaaaccaa gtaccgcacc aagcaagatg cgccg       55

SEQ ID NO: 55           moltype = DNA  length = 31
FEATURE                 Location/Qualifiers
source                  1..31
                        mol_type = other DNA
                        organism = synthetic construct
SEQUENCE: 55
gcttaatcta aagcatcaat gaccataaat c                                31

SEQ ID NO: 56           moltype = DNA  length = 47
FEATURE                 Location/Qualifiers
source                  1..47
                        mol_type = other DNA
                        organism = synthetic construct
SEQUENCE: 56
ccagaaccct agctgataaa ttaatgccgg agaaacgtta ccgtaat              47

SEQ ID NO: 57           moltype = DNA  length = 31
FEATURE                 Location/Qualifiers
source                  1..31
                        mol_type = other DNA
                        organism = synthetic construct
SEQUENCE: 57
atcggccttt tgattagtaa taagagaata t                                31

SEQ ID NO: 58           moltype = DNA  length = 39
FEATURE                 Location/Qualifiers
source                  1..39
```

-continued

```
                             mol_type = other DNA
                             organism = synthetic construct
SEQUENCE: 58
aatcctttgc ccgaacgtat tagactttac agttatcta                               39

SEQ ID NO: 59            moltype = DNA   length = 58
FEATURE                  Location/Qualifiers
source                   1..58
                         mol_type = other DNA
                         organism = synthetic construct
SEQUENCE: 59
caccgactaa agacaaaagg gcgccaaaag aactggcatc cttttaaag ttgggtaa      58

SEQ ID NO: 60            moltype = DNA   length = 38
FEATURE                  Location/Qualifiers
source                   1..38
                         mol_type = other DNA
                         organism = synthetic construct
SEQUENCE: 60
tgagagattt caaatagaga tagaaccctt tcacacga                                38

SEQ ID NO: 61            moltype = DNA   length = 54
FEATURE                  Location/Qualifiers
source                   1..54
                         mol_type = other DNA
                         organism = synthetic construct
SEQUENCE: 61
ttttgctatt ccacagacag cccaccgtac tcaggaggta gcggggatat tttc          54

SEQ ID NO: 62            moltype = DNA   length = 48
FEATURE                  Location/Qualifiers
source                   1..48
                         mol_type = other DNA
                         organism = synthetic construct
SEQUENCE: 62
aaatctacgt taataaaaaa ccaaaatagc gctggatagg ctttcgag                    48

SEQ ID NO: 63            moltype = DNA   length = 54
FEATURE                  Location/Qualifiers
source                   1..54
                         mol_type = other DNA
                         organism = synthetic construct
SEQUENCE: 63
aatcataagg gaaccggctg gctgaccttc atcaacttta atcattgtga atta          54

SEQ ID NO: 64            moltype = DNA   length = 39
FEATURE                  Location/Qualifiers
source                   1..39
                         mol_type = other DNA
                         organism = synthetic construct
SEQUENCE: 64
cgtaggaacc aagaagcttt cctcgttaga agagctaaa                               39

SEQ ID NO: 65            moltype = DNA   length = 39
FEATURE                  Location/Qualifiers
source                   1..39
                         mol_type = other DNA
                         organism = synthetic construct
SEQUENCE: 65
cgcttctggc caagctagcc caataattga gcgctaata                               39

SEQ ID NO: 66            moltype = DNA   length = 55
FEATURE                  Location/Qualifiers
source                   1..55
                         mol_type = other DNA
                         organism = synthetic construct
SEQUENCE: 66
agcaaaatca atagaaaatt catttacgca gtatgttagc aatgaaacga cgttg           55

SEQ ID NO: 67            moltype = DNA   length = 56
FEATURE                  Location/Qualifiers
source                   1..56
                         mol_type = other DNA
                         organism = synthetic construct
SEQUENCE: 67
gccggaaggg aacaaacggc ggattaaatg tgagcgagta tgtcaatcat atgtac         56

SEQ ID NO: 68            moltype = DNA   length = 54
FEATURE                  Location/Qualifiers
```

-continued

```
source                    1..54
                          mol_type = other DNA
                          organism = synthetic construct
SEQUENCE: 68
ttgtttggat tatacaaaga aaccaccaga attttaaaag tttgagtaac atta        54

SEQ ID NO: 69             moltype = DNA   length = 58
FEATURE                   Location/Qualifiers
source                    1..58
                          mol_type = other DNA
                          organism = synthetic construct
SEQUENCE: 69
aaccaccaag cgggcgctag ggcgctggca aactaaatcg gaaccctgag gtgccgta     58

SEQ ID NO: 70             moltype = DNA   length = 54
FEATURE                   Location/Qualifiers
source                    1..54
                          mol_type = other DNA
                          organism = synthetic construct
SEQUENCE: 70
tcgtcgctca tagcgatagc ttaccggctt aggttgggtc aatcgcaaga atac         54

SEQ ID NO: 71             moltype = DNA   length = 33
FEATURE                   Location/Qualifiers
source                    1..33
                          mol_type = other DNA
                          organism = synthetic construct
SEQUENCE: 71
tacagttcat ataatgggac aaaatcatag gtc                               33

SEQ ID NO: 72             moltype = DNA   length = 47
FEATURE                   Location/Qualifiers
source                    1..47
                          mol_type = other DNA
                          organism = synthetic construct
SEQUENCE: 72
cgtcaataga taatacctaa tagattagag cctcaaataa tttgaat               47

SEQ ID NO: 73             moltype = DNA   length = 55
FEATURE                   Location/Qualifiers
source                    1..55
                          mol_type = other DNA
                          organism = synthetic construct
SEQUENCE: 73
ccgaacgaac caccagccac gctgagagcc agtcaatcaa tatctggtta ggagc        55

SEQ ID NO: 74             moltype = DNA   length = 46
FEATURE                   Location/Qualifiers
source                    1..46
                          mol_type = other DNA
                          organism = synthetic construct
SEQUENCE: 74
ggtcagtgca ggtcaggaac cgccaagttt gtgtataaga aaataa                 46

SEQ ID NO: 75             moltype = DNA   length = 56
FEATURE                   Location/Qualifiers
source                    1..56
                          mol_type = other DNA
                          organism = synthetic construct
SEQUENCE: 75
aacaagagaa tcgatgattt ttagaaccct catttgcggg aataacctaa cgagta       56

SEQ ID NO: 76             moltype = DNA   length = 47
FEATURE                   Location/Qualifiers
source                    1..47
                          mol_type = other DNA
                          organism = synthetic construct
SEQUENCE: 76
ggattcgcca tcggaatatc atcgccaagg gttagaacct accatat               47

SEQ ID NO: 77             moltype = DNA   length = 55
FEATURE                   Location/Qualifiers
source                    1..55
                          mol_type = other DNA
                          organism = synthetic construct
SEQUENCE: 77
gtaaaacaga aataaaatga ataattcatt taacatcaac aaatcaaacc gcctg        55

SEQ ID NO: 78             moltype = DNA   length = 55
```

-continued

```
FEATURE            Location/Qualifiers
source             1..55
                   mol_type = other DNA
                   organism = synthetic construct
SEQUENCE: 78
tgaaaaattg cgccattaaa ataccagta ataaaaggga gccattgcaa cagga          55

SEQ ID NO: 79        moltype = DNA   length = 48
FEATURE            Location/Qualifiers
source             1..48
                   mol_type = other DNA
                   organism = synthetic construct
SEQUENCE: 79
tgtgataaca taattatatt taactcgagc cagtaataac aagtgttt               48

SEQ ID NO: 80        moltype = DNA   length = 30
FEATURE            Location/Qualifiers
source             1..30
                   mol_type = other DNA
                   organism = synthetic construct
SEQUENCE: 80
accctcccta ttataacatc caataaatca                                   30

SEQ ID NO: 81        moltype = DNA   length = 48
FEATURE            Location/Qualifiers
source             1..48
                   mol_type = other DNA
                   organism = synthetic construct
SEQUENCE: 81
agacttcata gtaaatgtt tagaagaggc ttttgcaaaa aggacgtt               48

SEQ ID NO: 82        moltype = DNA   length = 47
FEATURE            Location/Qualifiers
source             1..47
                   mol_type = other DNA
                   organism = synthetic construct
SEQUENCE: 82
aaaaatcagg tcatttttt aaattagcat ttctgaaacc cgtataa                47

SEQ ID NO: 83        moltype = DNA   length = 47
FEATURE            Location/Qualifiers
source             1..47
                   mol_type = other DNA
                   organism = synthetic construct
SEQUENCE: 83
gcctcaggaa ttttttgttaa atcagctcat tttttaacct ttgaggg             47

SEQ ID NO: 84        moltype = DNA   length = 32
FEATURE            Location/Qualifiers
source             1..32
                   mol_type = other DNA
                   organism = synthetic construct
SEQUENCE: 84
tgcgaatata ggaacccatg tacagagcca cc                               32

SEQ ID NO: 85        moltype = DNA   length = 39
FEATURE            Location/Qualifiers
source             1..39
                   mol_type = other DNA
                   organism = synthetic construct
SEQUENCE: 85
cgtgccagtt cgtaacggcc agtgtgccgg agaaaatac                         39

SEQ ID NO: 86        moltype = DNA   length = 38
FEATURE            Location/Qualifiers
source             1..38
                   mol_type = other DNA
                   organism = synthetic construct
SEQUENCE: 86
tcactgcctg aaattggggt tttattcagg cctcctta                         38

SEQ ID NO: 87        moltype = DNA   length = 39
FEATURE            Location/Qualifiers
source             1..39
                   mol_type = other DNA
                   organism = synthetic construct
SEQUENCE: 87
cccccgatgc gaaaggcacc cgctataacg tcgggtatt                         39
```

-continued

```
SEQ ID NO: 88          moltype = DNA   length = 32
FEATURE                Location/Qualifiers
source                 1..32
                       mol_type = other DNA
                       organism = synthetic construct
SEQUENCE: 88
cgcggggagt gctagaggat cccccagtat cg                              32

SEQ ID NO: 89          moltype = DNA   length = 55
FEATURE                Location/Qualifiers
source                 1..55
                       mol_type = other DNA
                       organism = synthetic construct
SEQUENCE: 89
aaaggccgat aaagccaata gtagatgcaa ctccaccctc cgtaacactg agttt      55

SEQ ID NO: 90          moltype = DNA   length = 54
FEATURE                Location/Qualifiers
source                 1..54
                       mol_type = other DNA
                       organism = synthetic construct
SEQUENCE: 90
gtaatgtgtg taccaacgcg agcattccat agccaccct8 caacgcctgt agca       54

SEQ ID NO: 91          moltype = DNA   length = 55
FEATURE                Location/Qualifiers
source                 1..55
                       mol_type = other DNA
                       organism = synthetic construct
SEQUENCE: 91
catggaattc accagctgac ctgaatgcgc gtttaacctg attaagacgc tgaga      55

SEQ ID NO: 92          moltype = DNA   length = 32
FEATURE                Location/Qualifiers
source                 1..32
                       mol_type = other DNA
                       organism = synthetic construct
SEQUENCE: 92
atgatattac agcaaggcaa agaaggctta ga                              32

SEQ ID NO: 93          moltype = DNA   length = 46
FEATURE                Location/Qualifiers
source                 1..46
                       mol_type = other DNA
                       organism = synthetic construct
SEQUENCE: 93
tcatcagtcc agaaccatta cccaaatcaa cccgcgacgt acaacg                46

SEQ ID NO: 94          moltype = DNA   length = 45
FEATURE                Location/Qualifiers
source                 1..45
                       mol_type = other DNA
                       organism = synthetic construct
SEQUENCE: 94
aacggaagtt taatttcaag agtaatcttg cgaggcgccc cccag                45

SEQ ID NO: 95          moltype = DNA   length = 39
FEATURE                Location/Qualifiers
source                 1..39
                       mol_type = other DNA
                       organism = synthetic construct
SEQUENCE: 95
atttagaagt tattaaggag cggaattatc aatcaatat                       39

SEQ ID NO: 96          moltype = DNA   length = 33
FEATURE                Location/Qualifiers
source                 1..33
                       mol_type = other DNA
                       organism = synthetic construct
SEQUENCE: 96
aactaatgtc agtgaataag gcttgccctg acg                             33

SEQ ID NO: 97          moltype = DNA   length = 59
FEATURE                Location/Qualifiers
source                 1..59
                       mol_type = other DNA
                       organism = synthetic construct
SEQUENCE: 97
gattgccgca aaatccctta tattacaaaa taaacagcct ctggttaacg tgtctgggc  59
```

-continued

```
SEQ ID NO: 98            moltype = DNA   length = 64
FEATURE                  Location/Qualifiers
source                   1..64
                         mol_type = other DNA
                         organism = synthetic construct
SEQUENCE: 98
gagagttgca gcaaatcct gtttgataat ccaaataaga aacctctggt taacgtgtct   60
gggc                                                               64

SEQ ID NO: 99            moltype = DNA   length = 66
FEATURE                  Location/Qualifiers
source                   1..66
                         mol_type = other DNA
                         organism = synthetic construct
SEQUENCE: 99
cccaaatcaa gttttcaacg tcaaagggcg aatcaagatt agttgctctg gttaacgtgt   60
ctgggc                                                             66

SEQ ID NO: 100           moltype = DNA   length = 65
FEATURE                  Location/Qualifiers
source                   1..65
                         mol_type = other DNA
                         organism = synthetic construct
SEQUENCE: 100
aagcgaggcg gtaacaagag tccactatta caattttatc ctgactctgg ttaacgtgtc   60
tgggc                                                              65

SEQ ID NO: 101           moltype = DNA   length = 64
FEATURE                  Location/Qualifiers
source                   1..64
                         mol_type = other DNA
                         organism = synthetic construct
SEQUENCE: 101
tggttttttct tcgagatagg gttgagtacg agcgtctttc cagctctggt taacgtgtct   60
gggc                                                               64

SEQ ID NO: 102           moltype = DNA   length = 68
FEATURE                  Location/Qualifiers
source                   1..68
                         mol_type = other DNA
                         organism = synthetic construct
SEQUENCE: 102
atgctttcat agtaagcggg atcgtcaccc tgcaacggca aaggaatctc tggttaacgt   60
gtctgggc                                                           68

SEQ ID NO: 103           moltype = DNA   length = 66
FEATURE                  Location/Qualifiers
source                   1..66
                         mol_type = other DNA
                         organism = synthetic construct
SEQUENCE: 103
tcgtcattac cagatgaggc ttgcagggag acttttttctt cagcgctctg gttaacgtgt   60
ctgggc                                                             66

SEQ ID NO: 104           moltype = DNA   length = 67
FEATURE                  Location/Qualifiers
source                   1..67
                         mol_type = other DNA
                         organism = synthetic construct
SEQUENCE: 104
tgctgaacca gatacactga ttgctttgaa tcaataacaa atcaatctct ggttaacgtg   60
tctgggc                                                            67

SEQ ID NO: 105           moltype = DNA   length = 53
FEATURE                  Location/Qualifiers
source                   1..53
                         mol_type = other DNA
                         organism = synthetic construct
SEQUENCE: 105
attcattttg cggaacttct gaataatggt gactctggtt aacgtgtctg ggc         53

SEQ ID NO: 106           moltype = DNA   length = 60
FEATURE                  Location/Qualifiers
source                   1..60
                         mol_type = other DNA
                         organism = synthetic construct
SEQUENCE: 106
aacaaccatc gcccacgcat aacgtaaaat agtatgggac tctggttaac gtgtctgggc   60
```

```
SEQ ID NO: 107            moltype = DNA   length = 52
FEATURE                   Location/Qualifiers
source                    1..52
                          mol_type = other DNA
                          organism = synthetic construct
SEQUENCE: 107
gcgcagaggc gaatttacag taatctgtaa actctggtta acgtgtctgg gc          52

SEQ ID NO: 108            moltype = DNA   length = 76
FEATURE                   Location/Qualifiers
source                    1..76
                          mol_type = other DNA
                          organism = synthetic construct
SEQUENCE: 108
taattgtatc aacagtatga ggaagtttcc aaaacactca tctttgaaga cggtcctctg  60
gttaacgtgt ctggc                                                   76

SEQ ID NO: 109            moltype = DNA   length = 73
FEATURE                   Location/Qualifiers
source                    1..73
                          mol_type = other DNA
                          organism = synthetic construct
SEQUENCE: 109
gtgaattatt ttctcgtaat gccactacgc ctaaaacgaa agagcaactt tgctctggtt  60
aacgtgtctg ggc                                                     73

SEQ ID NO: 110            moltype = DNA   length = 75
FEATURE                   Location/Qualifiers
source                    1..75
                          mol_type = other DNA
                          organism = synthetic construct
SEQUENCE: 110
tctccaagaa caacttacag aggctttgag ccaagcgcga aacaaactgc tccactctgg  60
ttaacgtgtc tgggc                                                   75

SEQ ID NO: 111            moltype = DNA   length = 67
FEATURE                   Location/Qualifiers
source                    1..67
                          mol_type = other DNA
                          organism = synthetic construct
SEQUENCE: 111
ccttgctcag tacctttttac atccaaaatt atttgcacaa tcctgactct ggttaacgtg  60
tctgggc                                                            67

SEQ ID NO: 112            moltype = DNA   length = 76
FEATURE                   Location/Qualifiers
source                    1..76
                          mol_type = other DNA
                          organism = synthetic construct
SEQUENCE: 112
tcggtcatgg tgaatttaaa gccagaatgg aacgtcatac atggcttagt accagctctg  60
gttaacgtgt ctgggc                                                  76

SEQ ID NO: 113            moltype = DNA   length = 76
FEATURE                   Location/Qualifiers
source                    1..76
                          mol_type = other DNA
                          organism = synthetic construct
SEQUENCE: 113
cagtagcggc accattgaca ggaggttgag gccttgagta acagtgcatg aaagtctctg  60
gttaacgtgt ctgggc                                                  76

SEQ ID NO: 114            moltype = DNA   length = 68
FEATURE                   Location/Qualifiers
source                    1..68
                          mol_type = other DNA
                          organism = synthetic construct
SEQUENCE: 114
ttgggaatcc ttgatattca caaagtactg gtaataagtg agaaggactc tggttaacgt  60
gtctgggc                                                           68

SEQ ID NO: 115            moltype = DNA   length = 71
FEATURE                   Location/Qualifiers
source                    1..71
                          mol_type = other DNA
                          organism = synthetic construct
SEQUENCE: 115
aaaagccccc ttcaccggaa ccagagccac caccatcctc atatcaccgt ctctggttaa  60
```

-continued

```
cgtgtctggg c                                                           71

SEQ ID NO: 116          moltype = DNA   length = 67
FEATURE                 Location/Qualifiers
source                  1..67
                        mol_type = other DNA
                        organism = synthetic construct
SEQUENCE: 116
tgttcagaag cctgtttagt atcttaatgg tttgaaatga acgcgactct ggttaacgtg   60
tctgggc                                                                67

SEQ ID NO: 117          moltype = DNA   length = 67
FEATURE                 Location/Qualifiers
source                  1..67
                        mol_type = other DNA
                        organism = synthetic construct
SEQUENCE: 117
caccactgtt cttacaccac cagatgcccc ctgcatttcg ttactactct ggttaacgtg   60
tctgggc                                                                67

SEQ ID NO: 118          moltype = DNA   length = 53
FEATURE                 Location/Qualifiers
source                  1..53
                        mol_type = other DNA
                        organism = synthetic construct
SEQUENCE: 118
agcctaataa caaagtcaga gggtaataag agctctggtt aacgtgtctg ggc            53

SEQ ID NO: 119          moltype = DNA   length = 52
FEATURE                 Location/Qualifiers
source                  1..52
                        mol_type = other DNA
                        organism = synthetic construct
SEQUENCE: 119
catattatca ttagacggga gaagctatct tctctggtta acgtgtctgg gc             52

SEQ ID NO: 120          moltype = DNA   length = 52
FEATURE                 Location/Qualifiers
source                  1..52
                        mol_type = other DNA
                        organism = synthetic construct
SEQUENCE: 120
gatttttac agagagaata acataagcag actctggtta acgtgtctgg gc              52

SEQ ID NO: 121          moltype = DNA   length = 52
FEATURE                 Location/Qualifiers
source                  1..52
                        mol_type = other DNA
                        organism = synthetic construct
SEQUENCE: 121
ctattttgct tatccggtat tctattttca tctctggtta acgtgtctgg gc             52

SEQ ID NO: 122          moltype = DNA   length = 67
FEATURE                 Location/Qualifiers
source                  1..67
                        mol_type = other DNA
                        organism = synthetic construct
SEQUENCE: 122
tctgtccaaa gagcggtcag atccggtcac ggcgcccaat agcaccctct ggttaacgtg   60
tctgggc                                                                67

SEQ ID NO: 123          moltype = DNA   length = 68
FEATURE                 Location/Qualifiers
source                  1..68
                        mol_type = other DNA
                        organism = synthetic construct
SEQUENCE: 123
aaaattgtagg gtagcagcca ccaccctcag accagcatta ccattagctc tggttaacgt   60
gtctgggc                                                               68

SEQ ID NO: 124          moltype = DNA   length = 69
FEATURE                 Location/Qualifiers
source                  1..69
                        mol_type = other DNA
                        organism = synthetic construct
SEQUENCE: 124
tcgcattaca accgttcagt ataaagccaa cgtatacaaa tccagacgct ctggttaacg   60
tgtctgggc                                                              69
```

-continued

```
SEQ ID NO: 125          moltype = DNA   length = 59
FEATURE                 Location/Qualifiers
source                  1..59
                        mol_type = other DNA
                        organism = synthetic construct
SEQUENCE: 125
ctatcaggga gccgccaccc tcaacgattg gtagagccct ctggttaacg tgtctgggc    59

SEQ ID NO: 126          moltype = DNA   length = 60
FEATURE                 Location/Qualifiers
source                  1..60
                        mol_type = other DNA
                        organism = synthetic construct
SEQUENCE: 126
tgctggtata attgagaatc gccactagaa actaatgcac tctggttaac gtgtctgggc   60

SEQ ID NO: 127          moltype = DNA   length = 18
FEATURE                 Location/Qualifiers
source                  1..18
                        mol_type = other DNA
                        organism = synthetic construct
SEQUENCE: 127
tctatcaggg cgattttt                                                 18

SEQ ID NO: 128          moltype = DNA   length = 34
FEATURE                 Location/Qualifiers
source                  1..34
                        mol_type = other DNA
                        organism = synthetic construct
SEQUENCE: 128
ttttttggcc cactacgtga aagccggcgt tttt                               34

SEQ ID NO: 129          moltype = DNA   length = 24
FEATURE                 Location/Qualifiers
source                  1..24
                        mol_type = other DNA
                        organism = synthetic construct
SEQUENCE: 129
tttttaagcc tggggtgcct aatg                                          24

SEQ ID NO: 130          moltype = DNA   length = 32
FEATURE                 Location/Qualifiers
source                  1..32
                        mol_type = other DNA
                        organism = synthetic construct
SEQUENCE: 130
tttttaacgt ggcgagaacg gtacgccttt tt                                 32

SEQ ID NO: 131          moltype = DNA   length = 16
FEATURE                 Location/Qualifiers
source                  1..16
                        mol_type = other DNA
                        organism = synthetic construct
SEQUENCE: 131
ctacagggcg cttttt                                                   16

SEQ ID NO: 132          moltype = DNA   length = 24
FEATURE                 Location/Qualifiers
source                  1..24
                        mol_type = other DNA
                        organism = synthetic construct
SEQUENCE: 132
tttttcagct ggcgaaaggg ggat                                          24

SEQ ID NO: 133          moltype = DNA   length = 16
FEATURE                 Location/Qualifiers
source                  1..16
                        mol_type = other DNA
                        organism = synthetic construct
SEQUENCE: 133
tttttgtact atggtt                                                   16

SEQ ID NO: 134          moltype = DNA   length = 16
FEATURE                 Location/Qualifiers
source                  1..16
                        mol_type = other DNA
                        organism = synthetic construct
SEQUENCE: 134
cgctattacg cttttt                                                   16
```

-continued

```
SEQ ID NO: 135          moltype = DNA  length = 32
FEATURE                 Location/Qualifiers
source                  1..32
                        mol_type = other DNA
                        organism = synthetic construct
SEQUENCE: 135
tttttgattc tccgtgcata aagtgtattt tt                               32

SEQ ID NO: 136          moltype = DNA  length = 32
FEATURE                 Location/Qualifiers
source                  1..32
                        mol_type = other DNA
                        organism = synthetic construct
SEQUENCE: 136
tttttagaat cctgagatca cttgcctttt tt                               32

SEQ ID NO: 137          moltype = DNA  length = 32
FEATURE                 Location/Qualifiers
source                  1..32
                        mol_type = other DNA
                        organism = synthetic construct
SEQUENCE: 137
tttttttaaaa ctagcaacaa cccgtcgttt tt                              32

SEQ ID NO: 138          moltype = DNA  length = 32
FEATURE                 Location/Qualifiers
source                  1..32
                        mol_type = other DNA
                        organism = synthetic construct
SEQUENCE: 138
tttttgagta gaagaagctc aatcgtcttt tt                               32

SEQ ID NO: 139          moltype = DNA  length = 32
FEATURE                 Location/Qualifiers
source                  1..32
                        mol_type = other DNA
                        organism = synthetic construct
SEQUENCE: 139
tttttcaagg ataaaaaacg gtaatcgttt tt                               32

SEQ ID NO: 140          moltype = DNA  length = 32
FEATURE                 Location/Qualifiers
source                  1..32
                        mol_type = other DNA
                        organism = synthetic construct
SEQUENCE: 140
tttttttgaaa tggattaggt gaggcggttt tt                              32

SEQ ID NO: 141          moltype = DNA  length = 17
FEATURE                 Location/Qualifiers
source                  1..17
                        mol_type = other DNA
                        organism = synthetic construct
SEQUENCE: 141
gtggcacaga cattttt                                                17

SEQ ID NO: 142          moltype = DNA  length = 24
FEATURE                 Location/Qualifiers
source                  1..24
                        mol_type = other DNA
                        organism = synthetic construct
SEQUENCE: 142
tttttataca tttcgcaaat ggtc                                        24

SEQ ID NO: 143          moltype = DNA  length = 17
FEATURE                 Location/Qualifiers
source                  1..17
                        mol_type = other DNA
                        organism = synthetic construct
SEQUENCE: 143
tttttatatt tttgaat                                                17

SEQ ID NO: 144          moltype = DNA  length = 24
FEATURE                 Location/Qualifiers
source                  1..24
                        mol_type = other DNA
                        organism = synthetic construct
SEQUENCE: 144
```

-continued

```
gatttagttt gaccattagt tttt                                                24

SEQ ID NO: 145            moltype = DNA   length = 32
FEATURE                   Location/Qualifiers
source                    1..32
                          mol_type = other DNA
                          organism = synthetic construct
SEQUENCE: 145
tttttttaat tcgagcttat ttcaacgttt tt                                       32

SEQ ID NO: 146            moltype = DNA   length = 32
FEATURE                   Location/Qualifiers
source                    1..32
                          mol_type = other DNA
                          organism = synthetic construct
SEQUENCE: 146
tttttttcagt attaaccagt tgaaaggttt tt                                      32

SEQ ID NO: 147            moltype = DNA   length = 32
FEATURE                   Location/Qualifiers
source                    1..32
                          mol_type = other DNA
                          organism = synthetic construct
SEQUENCE: 147
tttttagagg gggtaaaata tcgcgttttt tt                                       32

SEQ ID NO: 148            moltype = DNA   length = 32
FEATURE                   Location/Qualifiers
source                    1..32
                          mol_type = other DNA
                          organism = synthetic construct
SEQUENCE: 148
tttttaattg aggaagaaca attcgacttt tt                                       32

SEQ ID NO: 149            moltype = DNA   length = 32
FEATURE                   Location/Qualifiers
source                    1..32
                          mol_type = other DNA
                          organism = synthetic construct
SEQUENCE: 149
ttttttttata ccagtcgaag ttttgccttt tt                                      32

SEQ ID NO: 150            moltype = DNA   length = 16
FEATURE                   Location/Qualifiers
source                    1..16
                          mol_type = other DNA
                          organism = synthetic construct
SEQUENCE: 150
tttttaactc gtatta                                                         16

SEQ ID NO: 151            moltype = DNA   length = 40
FEATURE                   Location/Qualifiers
source                    1..40
                          mol_type = other DNA
                          organism = synthetic construct
SEQUENCE: 151
tttttatgaa cggtgtgatt ttaagaactg gctcattttt                               40

SEQ ID NO: 152            moltype = DNA   length = 42
FEATURE                   Location/Qualifiers
source                    1..42
                          mol_type = other DNA
                          organism = synthetic construct
SEQUENCE: 152
tttttcagat gatggcaatt ctcatattcc tgattatttt tt                            42

SEQ ID NO: 153            moltype = DNA   length = 16
FEATURE                   Location/Qualifiers
source                    1..16
                          mol_type = other DNA
                          organism = synthetic construct
SEQUENCE: 153
aaagaggaca gtttttt                                                        16

SEQ ID NO: 154            moltype = DNA   length = 20
FEATURE                   Location/Qualifiers
source                    1..20
                          mol_type = other DNA
                          organism = synthetic construct
```

-continued

```
SEQUENCE: 154
tttttaccaa aaggcttttt                                                   20

SEQ ID NO: 155          moltype = DNA   length = 42
FEATURE                 Location/Qualifiers
source                  1..42
                        mol_type = other DNA
                        organism = synthetic construct
SEQUENCE: 155
tttttttcagg tttaacgtca ggaaattgcg tagatttttt tt                         42

SEQ ID NO: 156          moltype = DNA   length = 42
FEATURE                 Location/Qualifiers
source                  1..42
                        mol_type = other DNA
                        organism = synthetic construct
SEQUENCE: 156
ttttttttgcg ccgacaatga cagcttgata ccgatagttt tt                         42

SEQ ID NO: 157          moltype = DNA   length = 42
FEATURE                 Location/Qualifiers
source                  1..42
                        mol_type = other DNA
                        organism = synthetic construct
SEQUENCE: 157
tttttagaag atgatgaaac acaattacct gagcaaattt tt                          42

SEQ ID NO: 158          moltype = DNA   length = 42
FEATURE                 Location/Qualifiers
source                  1..42
                        mol_type = other DNA
                        organism = synthetic construct
SEQUENCE: 158
tttttgtctt tccagacgtt agatctaaag ttttgtcttt tt                          42

SEQ ID NO: 159          moltype = DNA   length = 42
FEATURE                 Location/Qualifiers
source                  1..42
                        mol_type = other DNA
                        organism = synthetic construct
SEQUENCE: 159
ttttttaga atccttgaaa aattaattaa ttttcccttt tt                           42

SEQ ID NO: 160          moltype = DNA   length = 42
FEATURE                 Location/Qualifiers
source                  1..42
                        mol_type = other DNA
                        organism = synthetic construct
SEQUENCE: 160
ttttttgata taagtatagc cgtgccgtcg agagggtttt tt                          42

SEQ ID NO: 161          moltype = DNA   length = 42
FEATURE                 Location/Qualifiers
source                  1..42
                        mol_type = other DNA
                        organism = synthetic construct
SEQUENCE: 161
tttttaatgc tgatgcaaat ctatataact atatgtattt tt                          42

SEQ ID NO: 162          moltype = DNA   length = 42
FEATURE                 Location/Qualifiers
source                  1..42
                        mol_type = other DNA
                        organism = synthetic construct
SEQUENCE: 162
ttttttttacc gttccagtaa gagcgcagtc tctgaatttt tt                         42

SEQ ID NO: 163          moltype = DNA   length = 42
FEATURE                 Location/Qualifiers
source                  1..42
                        mol_type = other DNA
                        organism = synthetic construct
SEQUENCE: 163
tttttgaata aacaccggaa tataaggcgt taaataattt tt                          42

SEQ ID NO: 164          moltype = DNA   length = 42
FEATURE                 Location/Qualifiers
source                  1..42
                        mol_type = other DNA
```

```
                        organism = synthetic construct
SEQUENCE: 164
ttttttctttt cataatcaaa atattagcgt ttgccatttt tt                          42

SEQ ID NO: 165          moltype = DNA   length = 42
FEATURE                 Location/Qualifiers
source                  1..42
                        mol_type = other DNA
                        organism = synthetic construct
SEQUENCE: 165
ttttttttagg cagaggcatt taacgccaac atgtaatttt tt                          42

SEQ ID NO: 166          moltype = DNA   length = 42
FEATURE                 Location/Qualifiers
source                  1..42
                        mol_type = other DNA
                        organism = synthetic construct
SEQUENCE: 166
tttttattga cggaaattat tgggagggaa ggtaaatttt tt                           42

SEQ ID NO: 167          moltype = DNA   length = 42
FEATURE                 Location/Qualifiers
source                  1..42
                        mol_type = other DNA
                        organism = synthetic construct
SEQUENCE: 167
tttttgataa gtcctgaaca actgtttatc aacaatattt tt                           42

SEQ ID NO: 168          moltype = DNA   length = 42
FEATURE                 Location/Qualifiers
source                  1..42
                        mol_type = other DNA
                        organism = synthetic construct
SEQUENCE: 168
tttttaaacc gaggaaacgc acaaagttac cagaaggttt tt                           42

SEQ ID NO: 169          moltype = DNA   length = 20
FEATURE                 Location/Qualifiers
source                  1..20
                        mol_type = other DNA
                        organism = synthetic construct
SEQUENCE: 169
tttttgagaa tcatcttttt                                                     20

SEQ ID NO: 170          moltype = DNA   length = 42
FEATURE                 Location/Qualifiers
source                  1..42
                        mol_type = other DNA
                        organism = synthetic construct
SEQUENCE: 170
tttttgaaaa tagcagcctt tgtttaacgt caaaaatttt tt                           42

SEQ ID NO: 171          moltype = DNA   length = 42
FEATURE                 Location/Qualifiers
source                  1..42
                        mol_type = other DNA
                        organism = synthetic construct
SEQUENCE: 171
tttttcttgc gggaggtttt gttagcgaac ctcccgattt tt                           42

SEQ ID NO: 172          moltype = DNA   length = 40
FEATURE                 Location/Qualifiers
source                  1..40
                        mol_type = other DNA
                        organism = synthetic construct
SEQUENCE: 172
cacccagcta aagaacgtgg actcttgggg tcaaagggag                              40

SEQ ID NO: 173          moltype = DNA   length = 47
FEATURE                 Location/Qualifiers
source                  1..47
                        mol_type = other DNA
                        organism = synthetic construct
SEQUENCE: 173
gacgacgagg gtaccgagct cgaactgcat taatgaatcg gccaacg                      47

SEQ ID NO: 174          moltype = DNA   length = 47
FEATURE                 Location/Qualifiers
source                  1..47
```

```
                              mol_type = other DNA
                              organism = synthetic construct
SEQUENCE: 174
acaccctgtt gccagaatca aaagaatagc cttcaccaga aacctgt           47

SEQ ID NO: 175          moltype = DNA   length = 39
FEATURE                 Location/Qualifiers
source                  1..39
                        mol_type = other DNA
                        organism = synthetic construct
SEQUENCE: 175
ttatcccggt ggttccgaaa tcgcttcacc gcgttgcgc                    39

SEQ ID NO: 176          moltype = DNA   length = 55
FEATURE                 Location/Qualifiers
source                  1..55
                        mol_type = other DNA
                        organism = synthetic construct
SEQUENCE: 176
atcctaattt acgagcaaac aacaaaagta cctagggcta tatccagaaa acgct   55

SEQ ID NO: 177          moltype = DNA   length = 39
FEATURE                 Location/Qualifiers
source                  1..39
                        mol_type = other DNA
                        organism = synthetic construct
SEQUENCE: 177
ttagcaaaat taagcagaga cagtcaaatc accatcaat                    39

SEQ ID NO: 178          moltype = DNA   length = 55
FEATURE                 Location/Qualifiers
source                  1..55
                        mol_type = other DNA
                        organism = synthetic construct
SEQUENCE: 178
tttattttgt cacaatcacc agtaacagaa tcaccctcag tattttttagg gtgag  55

SEQ ID NO: 179          moltype = DNA   length = 55
FEATURE                 Location/Qualifiers
source                  1..55
                        mol_type = other DNA
                        organism = synthetic construct
SEQUENCE: 179
atggtttacc agcgcctgag ccatgtagcg cgctccctca tcattgcctg cctga   55

SEQ ID NO: 180          moltype = DNA   length = 39
FEATURE                 Location/Qualifiers
source                  1..39
                        mol_type = other DNA
                        organism = synthetic construct
SEQUENCE: 180
gtgaataaac atttaacaaa atcactaaca aatttgagg                    39

SEQ ID NO: 181          moltype = DNA   length = 30
FEATURE                 Location/Qualifiers
source                  1..30
                        mol_type = other DNA
                        organism = synthetic construct
SEQUENCE: 181
agaaacatga gatttaggaa taccacattc                              30

SEQ ID NO: 182          moltype = DNA   length = 39
FEATURE                 Location/Qualifiers
source                  1..39
                        mol_type = other DNA
                        organism = synthetic construct
SEQUENCE: 182
atagaaagaa aaaaggcgct tttgagcaac aagaaagat                    39

SEQ ID NO: 183          moltype = DNA   length = 39
FEATURE                 Location/Qualifiers
source                  1..39
                        mol_type = other DNA
                        organism = synthetic construct
SEQUENCE: 183
aacaactttc ggttttcggt cgccgacgat aaacgaact                    39

SEQ ID NO: 184          moltype = DNA   length = 39
FEATURE                 Location/Qualifiers
```

```
source                 1..39
                       mol_type = other DNA
                       organism = synthetic construct
SEQUENCE: 184
atagaaagaa aaaaggcgct tttgagcaac aagaaagat                        39

SEQ ID NO: 185         moltype = DNA   length = 73
FEATURE                Location/Qualifiers
source                 1..73
                       mol_type = other DNA
                       organism = synthetic construct
SEQUENCE: 185
cggtcataag cgctcacgga taggttttca tcagtccaga accattaccc aaatcaaccc   60
gcgacgtaca acg                                                     73

SEQ ID NO: 186         moltype = DNA   length = 19
FEATURE                Location/Qualifiers
source                 1..19
                       mol_type = other DNA
                       organism = synthetic construct
SEQUENCE: 186
acctatccgt gagcgctta                                              19

SEQ ID NO: 187         moltype = DNA   length = 25
FEATURE                Location/Qualifiers
source                 1..25
                       mol_type = other DNA
                       organism = synthetic construct
SEQUENCE: 187
acctatccgt gagcgcttat gaccg                                       25

SEQ ID NO: 188         moltype = DNA   length = 39
FEATURE                Location/Qualifiers
source                 1..39
                       mol_type = other DNA
                       organism = synthetic construct
SEQUENCE: 188
aacaactttc ggttttcggt cgccgacgat aaacgaact                        39

SEQ ID NO: 189         moltype = DNA   length = 72
FEATURE                Location/Qualifiers
source                 1..72
                       mol_type = other DNA
                       organism = synthetic construct
SEQUENCE: 189
cgaagtcact cccaggcagc tccaattaac ggaagtttaa tttcaagagt aatcttgcga   60
ggcgcccccc ag                                                     72

SEQ ID NO: 190         moltype = DNA   length = 19
FEATURE                Location/Qualifiers
source                 1..19
                       mol_type = other DNA
                       organism = synthetic construct
SEQUENCE: 190
ttggagctgc ctgggagtg                                              19

SEQ ID NO: 191         moltype = DNA   length = 25
FEATURE                Location/Qualifiers
source                 1..25
                       mol_type = other DNA
                       organism = synthetic construct
SEQUENCE: 191
ttggagctgc ctgggagtga cttcg                                       25

SEQ ID NO: 192         moltype = DNA   length = 20
FEATURE                Location/Qualifiers
source                 1..20
                       mol_type = other DNA
                       organism = synthetic construct
SEQUENCE: 192
gatgaatggt gggtgagagg                                             20

SEQ ID NO: 193         moltype = DNA   length = 59
FEATURE                Location/Qualifiers
source                 1..59
                       mol_type = other DNA
                       organism = synthetic construct
SEQUENCE: 193
cctctcaccc accattcatc tttttttttt ttttttttgc ccagacacgt taaccagag    59
```

-continued

```
SEQ ID NO: 194      moltype = DNA  length = 18
FEATURE             Location/Qualifiers
source              1..18
                    mol_type = other DNA
                    organism = synthetic construct
SEQUENCE: 194
aaaaaaaaaa aaaaaaaa                                              18
```